US006159707A

United States Patent [19]
Ronnett et al.

[11] Patent Number: 6,159,707
[45] Date of Patent: Dec. 12, 2000

[54] SPERM RECEPTORS

[75] Inventors: Gabriele V. Ronnett, Lutherville; Loren Walensky, Baltimore, both of Md.; Martial Ruat, Bourg la Reine, France; Solomon H. Snyder, Baltimore, Md.

[73] Assignee: Johns Hopkins University School of Medicine, Baltimore, Md.

[21] Appl. No.: 08/748,506

[22] Filed: Nov. 8, 1996

Related U.S. Application Data

[60] Provisional application No. 60/033,751, Sep. 16, 1996.

[51] Int. Cl.$^7$ .................................................... C12N 15/00
[52] U.S. Cl. ...................... 435/69.1; 435/7.1; 435/320.1; 435/325; 435/252.3; 435/254.11; 536/23.5; 536/23.1; 536/24.3; 536/24.31; 530/350
[58] Field of Search ............................... 435/69.1, 320.1, 435/252.3, 254.11, 325, 7.1; 536/23.5, 23.1, 24.3, 24.31; 530/350; 514/2

[56] References Cited

U.S. PATENT DOCUMENTS

| | | | |
|---|---|---|---|
| 5,030,722 | 7/1991 | Snyder et al. | 536/27 |
| 5,128,246 | 7/1992 | Snyder et al. | 435/69.1 |
| 5,260,270 | 11/1993 | Snyder et al. | 514/2 |

FOREIGN PATENT DOCUMENTS

| | | |
|---|---|---|
| WO 94/15630 | 7/1994 | WIPO . |
| WO 94/16684 | 8/1994 | WIPO . |
| WO 95/15764 | 6/1995 | WIPO . |

OTHER PUBLICATIONS

Marra et al., the WasU–HHMI Mouse EST project, EST accession Number W12826, Sep. 5, 1996.
Alexander, "Future Contraceptives," *Scientific American*, 136–141 (Sep. 1995).
Buck et al., "A novel multigene family may encode odorant receptors: a molecular basis for odor recognition," *Cell*, 65, 175–187 (1991).
Cohen–Dayag et al., "Sequential Acquisition of Chemotactic Responsiveness by Human Spermatozoa," *Biol. Reprod.*, 50(4), 786–790.
Dawson et al., "β–Adrenergic Receptor Kinase–2 and β–Arrestin–2 as Mediators of Odorant–Induced Desensitization." *Science*, 259, 825–829 (1993).
Gnessi et al., "Evidence for the Presence of Specific Receptors for N–Formyl Chemotactic Peptides on Human Spermatazoa," *J. Clin. Endocrinol. Metab.*, 637(4), 841–846 (1986).
Isahakia et al., "Anti–Sperm and Anti–Ovum Vaccines: the Selection of Candidate Antigens and the Outcome of Preclinical Studies," *Scand. J. Immunol.*, 36 (Suppl. 11), 118–122 (1992).
"Proteins May Help Sperm 'Sniff Out'the Egg," *Focus on Hopkins* (photo and video tipsheet from the Office of Communications and Public Affairs at the John Hopkins Medical Institutions) (Summer, 1995).
"Proteins May Help Sperm 'Sniff Out'Eggs," *Johns Hopkins News Release* (Jan. 26, 1995).
"Proteins may help sperm 'sniff 'their way to eggs," *The John Hopkins Gazette*, p. 4 (Feb. 6, 1995).
"Sperm sniff out eggs," *Hopkins Physician Update*, page 4 (Jun. 1995).

Makler et al., "A new model for investigating in real–time the existense of chemotaxis in human spermatazoa," *Fer. Ster.*, 57(5), 1066–1074 (1992).
Parmentier et al., "Expression of members of the putative olfactory receptor gene family in mammalian germ cells," *Nature*, 355, 453–455 (1992).
Purdy, "Sperm Sniff Out Eggs," *Hopkins Medical News*, 13(Spring, 1995).
Ralt et al., "Chemotaxis and Chemokinesis of Human Spermatazoa to Follicular Factors," *Biol. Reprod.*, 50, 774–785 (1994).
Ralt et al., "Sperm attraction to a follicular factor(s) correlates with human egg fertilizability," *Proc. Natl. Acad. Sci.*, 88(7), 2840–2844 (1991).
Ronnett et al., "A Tale of Two Senses," *Neuron*, 15, 11–16 (1995).
Vanderhaeghen et al., "Olefactory Receptors are Displayed on Dog Mature Sperm Cells," *J. Cell Biology*, 123 (6), 1441–1452 (1993).
Walensky et al., "Odorant Receptors and Desensitization Proteins Colocalize in Mammalian Sperm," *Molecular Medicine,*, 1 (2), 130–134 (1995).
Walensky et al., "Identification of novel members of the odorant receptor family in rat spermatids," poster presentation at the Society for Neuroscience meeting, San Diego, CA Nov 11–16, 1995 (*Society for Neuroscience*, 21, 57.12 (1995)).
Walensky et al., "Molecular cloning of novel sperm chemoreceptors," poster presentation at the American Society for Cell Biology, Washington, D.C., Dec. 9–13, 1995.
Zhu et al., "Sequence homology among sperm antigens involved in mammlian fertizlization: search for a common epitope for immunocontraception," *Archives of Andrology*, 33, 141–144 (1994).
Walensky et al., "Roles for novel memebers of the odorant receptor family and sperm inositol 1,4,5–tripjosphate receptors in mammalian fertilization," Thirty–fifth Annual Meeting of the American Society for Cell Biology, Washington, D.C. Dec. 9–13, 1995, *Molecular Biology of the Cell*, 6, (Suppl.), 8a, Abstract No. 41 (1995).
Raming et al., "Cloninig and expression of odorant receptors," *Nature*, 361, 353–356 (1993).
Nef et al., "Spatial pattern of receptor expression in the olfactory epithelium," *Proc. National Academy of Sci. USA*, 89, 8948–8952 (1992).
Walensky et al., "Two novel families of odorant receptors are expressed in rat spermatids," Sixth Annual Meeting of the International Congress on Cell Biology and the Thirty–sixth American Society for Cell Biology, San Francisco, California, Dec. 7–11, 1996, *Molecular Biology of the Cell*, 7, (Suppl.), 638a, Abstract No. 3711 (1996).

Primary Examiner—Lorraine Spector
Assistant Examiner—Eliane Lazar-Wesley
Attorney, Agent, or Firm—Leydig, Voit & Mayer,Ltd.

[57] ABSTRACT

The present invention provides a nucleic acid comprising a sequence that encodes a sperm receptor that is related to, but is different from, a receptor of the odorant receptor family. The present invention also provides a method of obtaining a nucleic acid that comprises a sequence that encodes a sperm receptor, as well as a means of using the elements of the invention in a method of contraception, a method of detecting autoimmune infertility, and a method of affecting fertility.

19 Claims, 25 Drawing Sheets

```
           10         20         30         40         50
            *          *          *          *          *
ATGAC TGTCA ACTGT TCTCT GTGGC AGGAG AATAG TTTGA CTGTC AAACA
TACTG ACAGT TGACA AGAGA CACCG TCCTC TTATC AAACT GACAG TTTGT 60         70         80         90        100
            *          *          *          *          *
CTTTG CATTT GCCAA GTTCT CTGAG GTCCC TGGAG AATGC TTCCT CCTGT
GAAAC GTAAA CGGTT CAAGA GACTC CAGGG ACCTC TTACG AAGGA GGACA 110        120        130        140        150
            *          *          *          *          *
TCAAC CTCAT CCTTC TCATG TTCTT AGTAT CACTA ACAGG AAATA CTCTC
AGTTG GAGTA GGAAG AGTAC AAGAA TCATA GTGAT TGTCC TTTAT GAGAG 160        170        180        190        200
            *          *          *          *          *
ATAGT CCTTG CTATT TGTAC CAGTC CATCT CTACA CACCC CCATG TACTT
TATCA GGAAC GATAA ACATG GTCAG GTAGA GATGT GTGGG GGTAC ATGAA 210        220        230        240        250
            *          *          *          *          *
CTTTC TGGCC AACTT GTCTC TCCTG GAGAT TGGCT ATACT TGCTC TGTCA
GAAAG ACCGG TTGAA CAGAG AGGAC CTCTA ACCGA TATGA ACGAG ACAGT 260        270        280        290        300
            *          *          *          *          *
TACCC AAGAT GCTGC AGAGC CTTGT GAGTG AGGCC AGAGA GATCT CTCGG
ATGGG TTCTA CGACG TCTCG GAACA CTCAC TCCGG TCTCT CTAGA GAGCC 310        320        330        340        350
            *          *          *          *          *
GAGGG ATGTG CCACA CAGAT GTTTT TTTTC GCATT TTTTG GTATA ACTGA
CTCCC TACAC GGTGT GTCTA CAAAA AAAAG CGTAA AAAAC CATAT TGACT 360        370        380        390        400
            *          *          *          *          *
GTGCT GCCTA TTGGC AGCCA TGGCC TTTGA CCGCT GCATG GCCAT ATGCT
CACGA CGGAT AACCG TCGGT ACCGG AAACT GGCGA CGTAC CGGTA TACGA 410        420        430        440        450
            *          *          *          *          *
CCCCA CTCCA CTATG CAACC CGAAT GAGTC GNGAG GTATG TGCCC ATTTG
GGGGT GAGGT GATAC GTTGG GCTTA CTCAG CNCTC CATAC ACGGG TAAAC 460        470        480        490        500
            *          *          *          *          *
GCAAT TGTTT CATGG GGAAT GGGAT GCATA GTAAG TCTGG GACAA ACCAA
CGTTA ACAAA GTACC CCTTA CCCTA CGTAT CATTC AGACC CTGTT TGGTT 510        520        530        540        550
            *          *          *          *          *
TTTTA TTTTC TCCTT GAACT TCTGT GGACC CTGTG AAATA GACCA CTTCT
AAAAT AAAAG AGGAA CTTGA AGACA CCTGG GACAC TTTAT CTGGT GAAGA 560        570        580        590        600
            *          *          *          *          *
TCTGT GACCT TCCAC CTCTC CTGGC ACTTG CCTGT GGAGA TACAT CCCAA
AGACA CTGGA AGGTG GAGAG GACCG TGAAC GGACA CCTCT ATGTA GGGTT 610        620        630        640        650
            *          *          *          *          *
AACGA GGCTG CCATC TTTGT GGTAG CAGTC CTCTG CATAT CTAGC CCATT
```

Fig. 2A

```
TTGCT CCGAC GGTAG AAACA CCATC GTCAG GAGAC GTATA GATCG GGTAA 660         670         680         690         700
          *           *           *           *           *
TTTGC TGATC ATTTA TTCTT ATGTC AAAAT TCTCA TTGCA GTGCT NCTGA
AAACG ACTAG TAAAT AAGAA TACAG TTTTA AGAGT AACGT CACGA NGACT 710         720         730         740         750
          *           *           *           *           *
TGCCT TCACC TGAGG GGCGC CATAA AGCTC TTTCC ACCTG TTCGT CTCAC
ACGGA AGTGG ACTCC CCGCG GTATT TCGAG AAAGG TGGAC AAGCA GAGTG 760         770         780         790         800
          *           *           *           *           *
CTACT TGTAG TCACA CTTTT TTATG GCTCA GCATG TATTA CCTAT TTGAG
GATGA ACATC AGTGT GAAAA AATAC CGAGT CGTAC ATAAT GGATA AACTC 810         820         830         840         850
          *           *           *           *           *
GCCCA AGTCT AGCCA CTCAC CAGGA ATGGA CAAAT TCTTG GCCCT CTTCT
CGGGT TCAGA TCGGT GAGTG GTCCT TACCT GTTTA AGAAC CGGGA GAAGA 860         870         880         890         900
          *           *           *           *           *
ACACA GTAGT GACAT CCATG CTGAA CCCTA TCATC TATAG TTTAA GGAAC
TGTGT CATCA CTGTA GGTAC GACTT GGGAT AGTAG ATATC AAATT CCTTG 910         920         930         940         950
          *           *           *           *           *
AAGGA AGTCA AGGCA GCACT GAGAA GAACT CTGGG CCTGA AAAAA ATTCT
TTCCT TCAGT TCCGT CGTGA CTCTT CTTGA GACCC GGACT TTTTT TAAGA

960
          *
GTCAA TTAAT AGGTA A
CAGTT AATTA TCCAT T
```

Fig. 2B

```
          10         20         30         40         50
          *          *          *          *          *
ATGAG TGTCA ACTGT TCGCT GTGGC AGGAG AATAG TTTGT CTGTC AAACG
TACTC ACAGT TGACA AGCGA CACCG TCCTC TTATC AAACA GACAG TTTGC 60         70         80         90        100
          *          *          *          *          *
CTTTG CATTT GCCAA GTTCT CTGAG GTCCC TGGAG AATGC TTCCT CCTGT
GAAAC GTAAA CGGTT CAAGA GACTC CAGGG ACCTC TTACG AAGGA GGACA 110        120        130        140        150
          *          *          *          *          *
TCACC CTCAT CCTTC TCATG TTCTT AGTAT CACTA ACAGG AAATG CTCTC
AGTGG GAGTA GGAAG AGTAC AAGAA TCATA GTGAT TGTCC TTTAC GAGAG 160        170        180        190        200
          *          *          *          *          *
ATAGC CCTTG CTGNT TGTAC CAGTC CATCT CTACA CACCC CCATG TACTT
TATCG GGAAC GACNA ACATG GTCAG GTAGA GATGT GTGGG GGTAC ATGAA 210        220        230        240        250
          *          *          *          *          *
CTTTC TGGCC AACTT GTCTC TCCTG GAGAT TGGCT ATACT TGCTC TGTCA
GAAAG ACCGG TTGAA CAGAG AGGAC CTCTA ACCGA TATGA ACGAG ACAGT 260        270        280        290        300
          *          *          *          *          *
TACCC AAGAT GCTGC AGAGC TTGT GAGTG AGGCC AGAGA GATCT CTAGG
ATGGG TTCTA CGACG TCTCG GAACA CTCAC TCCGG TCTCT CTAGA GATCC 310        320        330        340        350
          *          *          *          *          *
GAGGG ATGTG CCACA CAGAT GTTTT TCTTC ACATT TTTTG GCATA ACTGA
CTCCC TACAC GGTGT GTCTA CAAAA AGAAG TGTAA AAAAC CGTAT TGACT 360        370        380        390        400
          *          *          *          *          *
GTGCT GCCTA TTGGC AGCCA TGGCC TTTGA CCGCT GCATG GGCAT ATGCT
CACGA CGGAT AACCG TCGGT ACCGG AAACT GGCGA CGTAC CCGTA TACGA 410        420        430        440        450
          *          *          *          *          *
CCCCA CTCCA CTATG CAACC CGAAT GAGTC GTGAG GTATG TGCCC ATTTG
GGGGT GAGGT GATAC GTTGG GCTTA CTCAG CACTC CATAC ACGGG TAAAC 460        470        480        490        500
          *          *          *          *          *
GCAAT TGTTT CATGG GGAAT GGGAT GCATA GTAGG TCTGG ACAG. ACCAA
CGTTA ACAAA GTACC CCTTA CCCTA CGTAT CATCC AGACC CTGTC TGGTT 510        520        530        540        550
          *          *          *          *          *
TTTNA TTTNC TCCTT GAACT TCTGT GGACC TTGTG AGATA GACCA CTTCT
AAANT AAANG AGGAA CTTGA AGACA CCTGG AACAC TCTAT CTGGT GAAGA 560        570        580        590        600
          *          *          *          *          *
TCTGT GACCT CCAC CTCTC CTGGC ACTTG CCTGT GGTGA TACAT CCCAA
AGACA CTGGA AGGTG GAGAG GACCG TGAAC GGACA CCACT ATGTA GGGTT
```

Fig. 3A

```
            610         620         630         640         650
              *           *           *           *           *
AACGA GGCTG CCATC TTTGT GGCAG CAATC CTCTG TATAT CTAGT CCATT
TTGCT CCGAC GGTAG AAACA CCGTC GTTAG GAGAC ATATA GATCA GGTAA 660         670         680         690         700
              *           *           *           *           *
TTTGG TGATC CTTTA TTCTT ATGTC AGAAT TCTCG TTGCA GTGCT GGTGA
AAACC ACTAG GAAAT AAGAA TACAG TCTTA AGAGC AACGT CACGA CCACT 710         720         730         740         750
              *           *           *           *           *
TGCCT TCACC TGAGG GGCGC CATAA AGCTC TTTCC ACCTG TTCCT CACAC
ACGGA AGTGG ACTCC CCGCG GTATT TCGAG AAAGG TGGAC AAGGA GTGTG 760         770         780         790         800
              *           *           *           *           *
CTACT TGTAG TCACA CTCTT TTATG GCTCT GTGTC CTTTA CCTAT TTGAG
GATGA ACATC AGTGT GAGAA AATAC CGAGA CACAG GAAAT GGATA AACTC 810         820         830         840         850
              *           *           *           *           *
GCCCA AGTCT AGCCA CTCAC CAGGA ATGGA CAAAC TCTTG GCCCT CTTCT
CGGGT TCAGA TCGGT GAGTG GTCCT TACCT GTTTG AGAAC CGGGA GAAGA 860         870         880         890         900
              *           *           *           *           *
ACACA GCAGT GACAT CCATG CTGAA CCCTA TCATC TACAG TCTAA GGAAC
TGTGT CGTCA CTGTA GGTAC GACTT GGGAT AGTAG ATGTC AGATT CCTTG 910         920         930         940         950
              *           *           *           *           *
AAGGA AGTCA AGGCA GCACT GAGAA GAACT CTCGA CCTGA AAAAA ATTAT
TTCCT TCAGT TCCGT CGTGA CTCTT CTTGA GAGCT GGACT TTTTT TAATA

960
              *
GTCAA TTAAT AGGTA A
CAGTT AATTA TCCAT T
```

Fig. 3B

```
          10         20         30         40         50
          *          *          *          *          *
ATGAG TGTGA ACTGT TCTCT GTGGC AGGAG AATAG TTTGT CTGTC AAACG
TACTC ACAGT TGACA AGAGA CACCG TCCTC TTATC AAACA GACAG TTTGC 60         70         80         90        100
          *          *          *          *          *
CTTTG CATTT GCCAA GTTCT CTGAG GTCCC TGGAG AATGC TTCCT CCTGT
GAAAC GTAAA CGGTT CAAGA GACTC CAGGG ACCTC TTACG AAGGA GGACA 110        120        130        140        150
          *          *          *          *          *
TCACC CTCAT CCTTC TCATG TTCTT AGTAT CACTA ACAGG AAATA CTCTC
AGTGG GAGTA GGAAG AGTAC AAGAA TCATA GTGAT TGTCC TTTAT GAGAG 160        170        180        190        200
          *          *          *          *          *
ATAGC CCTTG CTATT TGTAC CAGTC CATCT CTACA CACCC CCATG TACTT
TATCG GGAAC GATAA ACATG GTCAG GTAGA GATGT GTGGG GGTAC ATGAA 210        220        230        240        250
          *          *          *          *          *
CTTTC TGGCC AACTT GTCTC TCCTG GAGAT TGGCT ATACT TGCTC TGTCA
GAAAG ACCGG TTGAA CAGAG AGGAC CTCTA ACCGA TATGA ACGAG ACAGT 260        270        280        290        300
          *          *          *          *          *
TACCC AAGAT GCTGC AGAGC CTTGT GAGTG AGGCC CGAGG GATCT CTTGG
ATGGG TTCTA CGACG TCTCG GAACA CTCAC TCCGG GCTCC CTAGA GAACC 310        320        330        340        350
          *          *          *          *          *
GAGGG TTGTG CCTCA CAGAT GTTCT TCTTC ATATT CTTTG GTATA ACTGA
CTCCC AACAC GGAGT GTCTA CAAGA AGAAG TATAA GAAAC CATAT TGACT 360        370        380        390        400
          *          *          *          *          *
GTGCT GCCTA TTGGC AGCCA TGGCC TTTGA CCGCT ATATG GCTAT ATGTT
CACGA CGGAT AACCG TCGGT ACCGG AAACT GGCGA TATAC CGATA TACAA 410        420        430        440        450
          *          *          *          *          *
CCCCA CTCCA CTATG CAACC CGAAT GAGTC GTGGG GTATG TGCCT ATTTG
GGGGT GAGGT GATAC GTTGG GCTTA CTCAG CACCC CATAC ACGGA TAAAC 460        470        480        490        500
          *          *          *          *          *
GCAAT TGTCT CATGG GTGAT GGGAT GCATA GTAGG TCTGG ACAG ACCAA
CGTTA ACAGA GTACC CACTA CCCTA CGTAT CATCC AGACC CTGTC TGGTT 510        520        530        540        550
          *          *          *          *          *
TTTTA TTTTC TCCTT GAACT TCTGT GGACC CTGTG AGATA GACCA CTTCT
AAAAT AAAAG AGGAA CTTGA AGACA CCTGG GACAC TCTAT CTGGT GAAGA
```

Fig. 4A

```
            560         570         580         590         600
             *           *           *           *           *
         TCTGT GACCT TCCAC CTCTC CTGGC ACTTG CCTGT GGTGA TACAT CCCAA
         AGACA CTGGA AGGTG GAGAG GACCG TGAAC GGACA CCACT ATGTA GGGTT 610         620         630         640         650
             *           *           *           *           *
         AATGA GGCTG CCATC TTTGT GGCAG CAGTG CTCTG CATAT TTAGT CCATT
         TTACT CCGAC GGTAG AAACA CCGTC GTCAC GAGAC GTATA AATCA GGTAA 660         670         680         690         700
             *           *           *           *           *
         TTTAC TGATC ATTTC TTCCT ATGTC AGAAT TCTCG TTGCA GTGCT GGTGA
         AAATG ACTAG TAAAG AAGGA TACAG TCTTA AGAGC AACGT CACGA CCACT 710         720         730         740         750
             *           *           *           *           *
         TGCCT TCACC TGAGG GGCGC CATAA AGCTC TCTCT ACCTG TTCAT CTCAC
         ACGGA AGTGG ACTCC CCGCG GTATT TCGAG AGAGA TGGAC AAGTA GAGTG 760         770         780         790         800
             *           *           *           *           *
         CTACT TGTAG TCACA CTCTT CTATG GCTCA ACATC TGCCA CCTAT TTGAG
         GATGA ACATC AGTGT GAGAA GATAC CGAGT TGTAG ACGGT GGATA AACTC 810         820         830         840         850
             *           *           *           *           *
         GTCCA AGTCT AGCCA CTCAC CAGGA GTGGA CAAAC TCTTG GCCCT CTTCT
         CAGGT TCAGA TCGGT GAGTG GTCCT CACCT GTTTG AGAAC CGGGA GAAGA 860         870         880         890         900
             *           *           *           *           *
         ATACA TCAGT GACAT CCATG CTGAA TCCCA TCATC TACAG CTTAA GGAAC
         TATGT AGTCA CTGTA GGTAC GACTT AGGGT AGTAG ATGTC GAATT CCTTG 910         920         930         940         950
             *           *           *           *           *
         AAGGA AGTAA AGGGT GCACT GAGAA GAACT CTGGG CCTGA AGAAA GTTCT
         TTCCT TCATT TCCCA CGTGA CTCTT CTTGA GACCC GGACT TCTTT CAAGA

960
             *
         GACAA TGAAA AGGTA A
         CTGTT ACTTT TCCAT T
```

Fig. 4B

```
                 10         20         30         40         50
                  *          *          *          *          *
        ATGAC TGTCA ACTGT TCTCT GTGGC AGGAG AATAG TTTGT CTGTC AAACG
        TACTG ACAGT TGACA AGAGA CACCG TCCTC TTATC AAACA GACAG TTTGC 60         70         80         90        100
                  *          *          *          *          *
        TTTTG CATTT GCCAA GTTCT CTGAG GTCCC TGGAG AATGC TTCCT CCTGT
        AAAAC GTAAA CGGTT CAAGA GACTC CAGGG ACCTC TTACG AAGGA GGACA 110        120        130        140        150
                  *          *          *          *          *
        TCACC CTCAT CCTTC TCATG TTCTT AGTAT CACTA ACAGG AAATG CTCTC
        AGTGG GAGTA GGAAG AGTAC AAGAA TCATA GTGAT TGTCC TTTAC GAGAG 160        170        180        190        200
                  *          *          *          *          *
        ATAGC CCTTG CTATT TGTAC CAGTC CATCT CTACA CACCC CCATG TACTT
        TATCG GGAAC GATAA ACATG GTCAG GTAGA GATGT GTGGG GGTAC ATGAA 210        220        230        240        250
                  *          *          *          *          *
        CTTTC TGGCC AACTT GTCTC TCCTG GAGAT TGGCT ATACT TGCTC TGTCA
        GAAAG ACCGG TTGAA CAGAG AGGAC CTCTA ACCGA TATGA ACGAG ACAGT 260        270        280        290        300
                  *          *          *          *          *
        TACCC AAGAT GCTGC AGAGT CTTGT GAGTG AGGCC CGAGA GATCT TTCAG
        ATGGG TTCTA CGACG TCTCA GAACA CTCAC TCCGG GCTCT CTAGA AAGTC 310        320        330        340        350
                  *          *          *          *          *
        GTGGG ATGTG CCACA CAGAT GTTTT TCTTC ATATT CTTTG GTATA ACTGA
        CACCC TACAC GGTGT GTCTA CAAAA AGAAG TATAA GAAAC CATAT TGACT 360        370        380        390        400
                  *          *          *          *          *
        GTGCT GCCTA TTGGC AGCCA TGGCC TTTGA CCGCT ATATG GCTAT ATGTT
        CACGA CGGAT AACCG TCGGT ACCGG AAACT GGCGA TATAC CGATA TACAA 410        420        430        440        450
                  *          *          *          *          *
        CCCCA CTCCA CTATG CAACC CGAAT GAGTC GTGAG GTATG TGCCC ACTTG
        GGGGT GAGGT GATAC GTTGG GCTTA CTCAG CACTC CATAC ACGGG TGAAC 460        470        480        490        500
                  *          *          *          *          *
        GCAAT TGTTT CATGG GTGAT GGGAT GCATA GTAGG TCTGG ACAGT ACCAA
        CGTTA ACAAA GTACC CACTA CCCTA CGTAT CATCC AGACC TGTCT TGGTT 510        520        530        540        550
                  *          *          *          *          *
        TTTTA TTTTC TCCTT GAACT TCTGT GGACC CTGTG AGATA GACCA CTTCT
        AAAAT AAAAG AGGAA CTTGA AGACA CCTGG GACAC TCTAT CTGGT GAAGA 560        570        580        590        600
                  *          *          *          *          *
        TCTGT GATCT TCCAC CTCTC CTGGC ACTTG CCTGT GGTGA TACAT CCCAA
        AGACA CTAGA AGGTG GAGAG GACCG TGAAC GGACA CCACT ATGTA GGGTT
```

Fig. 5A

```
              610         620         630         640         650
               *           *           *           *           *
ATTGA GGCTG CCATC TTTGT GGTAG TTGTC CTCTG CATAT CTAGC CCTTT
TAACT CCGAC GGTAG AAACA CCATC AACAG GAGAC GTATA GATCG GGAAA 660         670         680         690         700
               *           *           *           *           *
TTTGC TGATC ATTTA TTCTT ATGTC AGAAT TCTCG TTGCA GTGCT GGTGA
AAACG ACTAG TAAAT AAGAA TACAG TCTTA AGAGC AACGT CACGA CCACT 710         720         730         740         750
               *           *           *           *           *
TGCCT TCACC TGAGG GGCGC CACAA AGCCC TTTCA ACCTG TTCCT CCCAC
ACGGA AGTGG ACTCC CCGCG GTGTT TCGGG AAAGT TGGAC AAGGA GGGTG 760         770         780         790         800
               *           *           *           *           *
CTACT TGTAG TCACA CTCTT TTATG GCTCA GGATC TGTTA CCTAT TTGAG
GATGA ACATC AGTGT GAGAA AATAC CGAGT CCTAG ACAAT GGATA AACTC 810         820         830         840         850
               *           *           *           *           *
GCCTA AGTCT AGCCA CTCAC CAGGA ATGGA CAAAC TCTTG GCCCT CTTCT
CGGAT TCAGA TCGGT GAGTG GTCCT TACCT GTTTG AGAAC CGGGA GAAGA 860         870         880         890         900
               *           *           *           *           *
ACACA GCAGT GACAT CCATG TTGAA CCCTA TCATC TATAG TTTAA GGAAC
TGTGT CGTCA CTGTA GGTAC AACTT GGGAT AGTAG ATATC AAATT CCTTG 910         920         930         940         950
               *           *           *           *           *
AAGGA TGTCA AGGCA GCACT GAGAA GAATT CTGGC CCTGA AAAAA ATTCT
TTCCT ACAGT TCCGT CGTGA CTCTT CTTAA GACCG GGACT TTTTT TAAGA

960
               *
GTCAA TAAAT AAGTA A
CAGTT ATTTA TTCAT T
```

Fig. 5B

```
              10         20         30         40         50
               *          *          *          *          *
      ATGGA ATGGC TAATG ACAGA GGAGA CAAGG AATGG GACTT TGGTC CTGGA
      TACCT TACCG ATTAC TGTCT CCTCT GTTCC TTACC CTGAA ACCAG GACCT 60         70         80         90        100
               *          *          *          *          *
      GTTCA TCCTT GAGGG GTACC CTGTG GCCGA GCACC TGAAG ATCCT CTTCT
      CAAGT AGGAA CTCCC CATGG GACAC CGGCT CGTGG ACTTC TAGGA GAAGA 110        120        130        140        150
               *          *          *          *          *
      TCCTA CTGCA CTTGC TGGCC TACTT GGCCT CCCTC ATGGG CAACA TGCTC
      AGGAT GACGT GAACG ACCGG ATGAA CCGGA GGGAG TACCC GTTGT ACGAG 160        170        180        190        200
               *          *          *          *          *
      ATAAT TACCA TCACC TGTGT GGACC ACCGA CTGCA GACGC CCATG TACTT
      TATTA ATGGT AGTGG ACACA CCTGG TGGCT GACGT CTGCG GGTAC ATGAA 210        220        230        240        250
               *          *          *          *          *
      CTTTC TCAGC ACCTT CTCTT TTGTG GAGTG TTGTT TTATA ACTAC TGCTA
      GAAAG AGTCG TGGAA GAGAA AACAC CTCAC AACAA AATAT TGATG ACGAT 260        270        280        290        300
               *          *          *          *          *
      TCCCC CAGCT CCTCA CCATC ATTCT GTCAG GGAGG CAAAA GATTC CCTTT
      AGGGG GTCGA GGAGT GGTAG TAAGA CAGTC CCTCC GTTTT CTAAG GGAAA 310        320        330        340        350
               *          *          *          *          *
      GGGGT CTGCT TCTCA CAGGC CTTCG TCTAT CTTGT CGTGG GGGCA ACAGG
      CCCCA GACGA AGAGT GTCCG GAAGC AGATA GAACA GCACC CCCGT TGTCC 360        370        380        390        400
               *          *          *          *          *
      TTTTT TCCTT TTGGC TGCGT TATCC CTGGA CCGCT TTCTG GCCAT CTGCA
      AAAAA AGGAA AACCG ACGCA ATAGG GACCT GGCGA AAGAC CGGTA GACGT 410        420        430        440        450
               *          *          *          *          *
      AACCT CTACA TTATC CAACC ATCAT GAGCC CAAGG ATGTG CTTCC TTCTC
      TTGGA GATGT AATAG GTTGG TAGTA CTCGG GTTCC TACAC GAAGG AAGAG 460        470        480        490        500
               *          *          *          *          *
      GTTAC TGTCT GTTTA TTTTT GGGCT TCCTC TTCAT GGCCA GTCCA GTTGT
      CAATG ACAGA CAAAT AAAAA CCCGA AGGAG AAGTA CCGGT CAGGT CAACA 510        520        530        540        550
               *          *          *          *          *
      GATGC TTTCC AAGAC ATTTT ACTGT GGTCC AAACA TTATT CCTCA CTTTT
```

Fig. 6A

```
CTACG AAAGG TTCTG TAAAA TGACA CCAGG TTTGT AATAA GGAGT GAAAA 560         570         580         590         600
            *           *           *           *           *
TCTGT GATTT TGGAC CACTG GCAAA TCTCT CCTGT TCAGA AACCA GGTCT
AGACA CTAAA ACCTG GTGAC CGTTT AGAGA GGACA AGTCT TTGGT CCAGA 610         620         630         640         650
            *           *           *           *           *
ATTGA GATGC TGTTT TTTAC CCTTG CTGTA ATTGT GCTTT TTGCT TCCTT
TAACT CTACG ACAAA AAATG GGAAC GACAT TAACA CGAAA AACGA AGGAA 660         670         680         690         700
            *           *           *           *           *
TCTTA TAGCC ATCTT TGCAT ACAGC AATAT AGTAG TCACC ATAGT GAGAC
AGAAT ATCGG TAGAA ACGTA TGTCG TTATA TCATC AGTGG TATCA CTCTG 710         720         730         740         750
            *           *           *           *           *
TCCCT TCAGC CAGGG AGCGA CAGAG AGCTT TTTCC ACCTG CTCCT CTCAT
AGGGA AGTCG GTCCC TCGCT GTCTC TCGAA AAAGG TGGAC GAGGA GAGTA 760         770         780         790         800
            *           *           *           *           *
CTCAT TGTCC TCTCT CTAAT GTATG GCAGC TGTGC ATTTA TATAC CTGAA
GAGTA ACAGG AGAGA GATTA CATAC CGTCG ACACG TAAAT ATATG GACTT 810         820         830         840         850
            *           *           *           *           *
GCCAA AGCAG AGAAG CAGAG TGGAC ACCAA CAGAG AGGCT GCTCT TGTGA
CGGTT TCGTC TCTTC GTCTC ACCTG TGGTT GTCTC TCCGA CGAGA ACACT 860         870         880         890         900
            *           *           *           *           *
ACATG GTTGT GACAC CCCTT CTGAA CCCTG TCATC TACAC CCTGC GCAAC
TGTAC CAACA CTGTG GGGAA GACTT GGGAC AGTAG ATGTG GGACG CGTTG 910         920         930         940         950
            *           *           *           *           *
AAGCA GGTCC ACCAG GCTCT CAGGG ATGCT CTGTC CAGGC TTCAA TTACA
TTCGT CCAGG TGGTC CGAGA GTCCC TACGA GACAG GTCCG AAGTT AATGT 960         970         980
            *           *           *
CAGAT ATCAG AGGAG GAAGG CTCCT TTCCT TTGA
GTCTA TAGTC TCCTC CTTCC GAGGA AAGGA AACT
```

Fig. 6B

```
          10          20          30          40          50
           *           *           *           *           *
MTVNC SLWQE NSLTV KHFAF AKFSE VPGEC FLLFN LILLM FLVSL TGNTL 60          70          80          90         100
           *           *           *           *           *
IVLAI CTSPS LHTPM YFFLA NLSLL EIGYT CSVIP KMLQS LVSEA REISR 110         120         130         140         150
           *           *           *           *           *
EGCAT QMFFF AFFGI TECCL LAAMA FDRCM AICSP LHYAT RMSRE VCAHL 160         170         180         190         200
           *           *           *           *           *
AIVSW GMGCI VSLGQ TNFIF SLNFC GPCEI DHFFC DLPPL LALAC GDTSQ 210         220         230         240         250
           *           *           *           *           *
NEAAI FVVAV LCISS PFLLI IYSYV KILIA VLLMP SPEGR HKALS TCSSH 260         270         280         290         300
           *           *           *           *           *
LLVVT LFYGS ACITY LRPKS SHSPG MDKFL ALFYT VVTSM LNPII YSLRN 310         320
           *           *
KEVKA ALRRT LGLKK ILSIN R*
```

Fig. 7

```
          10         20         30         40         50
           *          *          *          *          *
MSVNC SLWQE NSLSV KRFAF AKFSE VPGEC FLLFT LILLM FLVSL TGNAL 60         70         80         90        100
           *          *          *          *          *
IALAX CTSPS LHTPM YFFLA NLSLL EIGYT CSVIP KMLQS LVSEA REISR 110        120        130        140        150
           *          *          *          *          *
EGCAT QMFFF TFFGI TECCL LAAMA FDRCM GICSP LHYAT RMSRE VCAHL 160        170        180        190        200
           *          *          *          *          *
AIVSW GMGCI VGLGQ TNXIX SLNFC GPCEI DHFFC DLPPL LALAC GDTSQ 210        220        230        240        250
           *          *          *          *          *
NEAAI FVAAI LCISS PFLVI LYSYV RILVA VLVMP SPEGR HKALS TCSSH 260        270        280        290        300
           *          *          *          *          *
LLVVT LFYGS VSFTY LRPKS SHSPG MDKLL ALFYT AVTSM LNPII YSLRN 310        320
           *          *
KEVKA ALRRT LDLKK IMSIN R*
```

Fig. 8

```
              10         20         30         40         50
               *          *          *          *          *
       MSVNC SLWQE NSLSV KRFAF AKFSE VPGEC FLLFT LILLM FLVSL TGNTL 60         70         80         90        100
               *          *          *          *          *
       IALAI CTSPS LHTPM YFFLA NLSLL EIGYT CSVIP KMLQS LVSEA RGISW 110        120        130        140        150
               *          *          *          *          *
       EGCAS QMFFF IFFGI TECCL LAAMA FDRYM AICSP LHYAT RMSRG VCAYL 160        170        180        190        200
               *          *          *          *          *
       AIVSW VMGCI VGLGQ TNFIF SLNFC GPCEI DHFFC DLPPL LALAC GDTSQ 210        220        230        240        250
               *          *          *          *          *
       NEAAI FVAAV LCIFS PFLLI ISSYV RILVA VLVMP SPEGR HKALS TCSSH 260        270        280        290        300
               *          *          *          *          *
       LLVVT LFYGS TSATY LRSKS SHSPG VDKLL ALFYT SVTSM LNPII YSLRN 310        320
               *          *
       KEVKG ALRRT LGLKK VLTMK R*
```

Fig. 9

```
        10          20          30          40          50
         *           *           *           *           *
MTVNC SLWQE NSLSV KRFAF AKFSE VPGEC FLLFT LILLM FLVSL TGNAL 60          70          80          90         100
         *           *           *           *           *
IALAI CTSPS LHTPM YFFLA NLSLL EIGYT CSVIP KMLQS LVSEA REIFQ 110         120         130         140         150
         *           *           *           *           *
VGCAT QMFFF IFFGI TECCL LAAMA FDRYM AICSP LHYAT RMSRE VCAHL 160         170         180         190         200
         *           *           *           *           *
AIVSW VMGCI VGLGQ TNFIF SLNFC GPCEI DHFFC DLPPL LALAC GDTSQ 210         220         230         240         250
         *           *           *           *           *
IEAAI FVVVV LCISS PFLLI IYSYV RILVA VLVMP SPEGR HKALS TCSSH 260         270         280         290         300
         *           *           *           *           *
LLVVT LFYGS GSVTY LRPKS SHSPG MDKLL ALFYT AVTSM LNPII YSLRN 310         320
         *           *
KDVKA ALRRI LALKK ILSIN K*
```

Fig. 10

```
         10         20         30         40         50
          *          *          *          *          *
MEWLM TEETR NGTLV LEFIL EGYPV AEHLK ILFFL LHLLA YLASL MGNML 60         70         80         90        100
          *          *          *          *          *
IITIT CVDHR LQTPM YFFLS TFSFV ECCFI TTAIP QLLTI ILSGR QKIPF 110        120        130        140        150
          *          *          *          *          *
GVCFS QAFVY LVVGA TGFFL LAALS LDRFL AICKP LHYPT IMSPR MCFLL 160        170        180        190        200
          *          *          *          *          *
VTVCL FLGFL FMASP VVMLS KTFYC GPNII PHFFC DFGPL ANLSC SETRS 210        220        230        240        250
          *          *          *          *          *
IEMLF FTLAV IVLFA SFLIA IFAYS NIVVT IVRLP SARER QRAFS TCSSH 260        270        280        290        300
          *          *          *          *          *
LIVLS LMYGS CAFIY LKPKQ RSRVD TNREA ALVNM VVTPL LNPVI YTLRN 310        320
          *          *
KQVHQ ALRDA LSRLQ LHRYQ RRKAP FL*
```

Fig. 11

```
A  MSVNCSLWQENSLSVKRFAFAKFSEVPGECFLLFLLILLMFLVSLTGNIL      50
B  MIVNCSLWQENSLSVKRFAFAKFSEVPGECFLLFLLILLMFLVSLTGNAL      50
C  MIVNCSLWQENSLIVKRFAFAKFSEVPGECFLLFNLILLMPLVSLTGNIL      50
D  MSVNCSLWQENSLSVKRFAFAKFSEVPGECFLLFLLILLMFLVSLTGNAL      50

A  IPLAICTSPSLHTPMYFFLANLSLLEIGYTCSVIPKMLQSLVSEARQISW     100
B  IPLAICTSPSLHTPMYFFLANLSLLEIGYTCSVIPKMLQSLVSEAREIFQ     100
C  IMLAICTSPSLHTPMYFFLANLSLLEIGYTCSVIPKMLQSLVSEAREISR     100
D  IPLAMCTSPSLHTPMYFFLANLSLLEIGYTCSVIPKMLQSLVSEAREISR     100

A  EGCASQMFFFLFFGITECCLLAAMAFDRYMAICSPLHYATRMSRQVCAML     150
B  VGCATQMFFFLFFGITECCLLAAMAFDRYMAICSPLHYATRMSREVCALL     150
C  EGCATQMFFFAFFGITECCLLAAMAFDRQMAICSPLHYATRMSREVCAHL     150
D  EGCATQMFFFLFFGITECCLLAAMAFDRQMAICSPLHYATRMSREVCAHL     150

A  AIVSWVMGCIVGLGQTNFIFSLNFCGPCEIDHFFCDLPPLLALACGDTSQ     200
B  AIVSWVMGCIVGLGQTNFIFSLNFCGPCEIDHFFCDLPPLLALACGDTSQ     200
C  AIVSWCMGCIVSLGQTNFIFSLNFCGPCEIDHFFCDLPPLLALACGDTSQ     200
D  AIVSWCMGCIVGLGQTNFIFSLNFCGPCEIDHFFCDLPPLLALACGDTSQ     200

A  NEAAIFVAAVLCIRSPFLIIISYVRILAVIMMPSPEGRHKALSTCSSH      250
B  IEAAIFVVVLCISSPFLIIIYSYVRILAVILMPSPEGRHKALSTCSSH      250
C  NEAAIFVVAVLCISSPFLIIIYSYVRILAVILMPSPEGRHKALSTCSSH     250
D  NEAAIFVAAILCISSPFLILYSYVRILAVIMMPSPEGRHKALSTCSSH     250

A  LLVVTLFYGSTSATYLRFKSSHSPGMDKLLALFYTSVTSMLNPIIYSLRN     300
B  LLVVTLFYGSGSVTYLRFKSSHSPGMDKLLALFYTAVTSMLNPIIYSLRN     300
C  LLVVTLFYGSACITYLRFKSSHSPGMDKFLALFYTVVTSMLNPIIYSLRN     300
D  LLVVTLFYGSVSFTYLRFKSSHSPGMDKLLALFYTAVTSMLNPIIYSLRN     300

A  K--------------------                                 301
B  KDVKAALRRILALKKILSINK                                 321
C  K--------------------                                 301
D  K--------------------                                 301
```

Fig. 12

```
          10         20         30         40         50
           *          *          *          *          *
ATGAC TGTCA ACTGT TCTCT GTGGC AGGAG AATAG TTTGT CTGTC AAACG
TACTG ACAGT TGACA AGAGA CACCG TCCTC TTATC AAACA GACAG TTTGC 60         70         80         90
           *          *          *          *
TTTTG CATTT GCCAA GTTCT CTGAG GTCCC TGGAG AATGC TTCCT C
AAAAC GTAAA CGGTT CAAGA GACTC CAGGG ACCTC TTACG AAGGA G
```

Fig. 13

```
          10              20              30
           *               *               *
MTVNC SLWQE NSLSV KRFAF AKFSE VPGEC FL
```

Fig. 14

Spermatid Chemoreceptor D-2

```
                                              TMD 1
MTVNCSLWQENSLTVKHFAFAKFSEVPGECFLLFNLILLMFLVSLTGNTL    50

TMD 2
IVLAICTSPSLHTPMYFFLANLSLLEIGYTCSVIPKMLQSLVSEAREISR    100

TMD 3
EGCATQMFFFAFFGITECCLLAAMAFDRCMAICSPLHYATRMSREVCAHL    150

TMD 4
AIVSWGMGCIVSLGQTNFIFSLNFCGPCEIDHFFCDLPPLLALACGDTSQ    200

TMD 5
NEAAIFVVAVLCISSPFLLIIYSYVKILIAVLLMPSPEGRHKALSTCSSH    250

TMD 6                         TMD 7
LLVVTLFYGSACITYLRPKSSHSPGMDKFLALFYTVVTSMLNPIIYSLRN    300

KEVKAALRRTLGLKKILSINR                                 321
```

Fig. 15

Alignment of SCR D Family:
Amino Acid Sequence

```
PCR-D.aa    --------------------------------------------------         -
D-9.aa      MIVNCSLWQENSISVKRFAFAKFSEVPGECFLLEILILLMFLVSLTGNPL        50
D-2.aa      MIVNCSLWQENSIIVKHFAFAKFSEVPGECFLLFNLILLMFLVSLTGNIL        50
D-7.aa      MEVNCSLWQENSLSVKRFAFAKFSEVPGECELLFDLILLMFLVSLTGNPL        50
D-8.aa      MEVNCSLWQENSLSVKRFAFAKFSEVPGECFLLFILILLMFLVSLTGNIL        50

PCR-D.aa    ----------------FLANLSLLEIGYTCSVIPKMLQSLVSEAREISR         33
D-9.aa      IALAICTSPSLHTPMYFFLANLSLLEIGYTCSVIPKMLQSLVSEAREIFQ       100
D-2.aa      IVLAICTSPSLHTPMYFFLANLSLLEIGYTCSVIPKMLQSLVSEAREISR       100
D-7.aa      IALAACTSPSLHTPMYFFLANLSLLEIGYTCSVIPKMLQSLVSEAREISR       100
D-8.aa      IALAICTSPSLHTPMYFFLANLSLLEIGYTCSVIPKMLQSLVSEARGISW       100

PCR-D.aa    EGCAIQMFFFIFFGITECCLLAAMAFDRMMICSPLHYATRMSREVCAHL         83
D-9.aa      VGCAIQMFFFFFFGITECCLLAAMAFDRMMICSPLHYATRMSREVCAHL        150
D-2.aa      EGCAIQMFFFNFFGITECCLLAAMAFDRQMICSPLHYATRMSREVCAHL        150
D-7.aa      EGCAIQMFFFIFFGITECCLLAAMAFDRMGICSPLHYATRMSREVCAHL        150
D-8.aa      EGCASQMFFFIFFGITECCLLAAMAFDRMMICSPLHYATRMSRIVCAML        150

PCR-D.aa    AIVSWGMGCIVGLGQTNFIFSLNFCGPCEIDHFFCDLPPLLALACGDTSQ       133
D-9.aa      AIVSWMMGCIVGLGQTNFIFSLNFCGPCEIDHEFCDLPPLLALACGDTSQ       200
D-2.aa      AIVSWGMGCIVSLGQTNFIFSLNFCGPCEIDHFFCDLPPLLALACGDTSQ       200
D-7.aa      AIVSWGMGCIVGLGQTNNIISLNFCGPCEIDHFFCDLPPLLALACGDTSQ       200
D-8.aa      AIVSWMMGCIVGLGQTNFIFSLNFCGPCEIDHFFCDLPPLLALACGDTSQ       200

PCR-D.aa    NEAAIFVAAILCISSPFILIIYSYVRIILMAVLMMPSPEGRHKALS----       178
D-9.aa      IEAAIFVVVLCIBSPELIIIYSYVRIILMAVLMMPSPEGRHKALSICSSH       250
D-2.aa      NEAAIFVVAVLCISSPFLIIIYSYVKILLAVLMPSPEGRHKALSICSSH        250
D-7.aa      NEAAIFVAAILCISSPFLMILYSYVRIILMAVLMMPSPEGRHKALSICSSH      250
D-8.aa      NEAAIFVAAVLCIFSPFLIIISSYVRIILMAVLMMPSPEGRHKALSICSSH      250

PCR-D.aa    --------------------------------------------------       178
D-9.aa      LLVVTLFYGSGSVTYLRFKSSHSPGMDKLLALFYTAVTSMLNPIIYSLRN       300
D-2.aa      LLVVTLFYGSACITYLRFKSSHSPGMDKFLALFYTVVTSMLNPIIYSLRN       300
D-7.aa      LLVVTLFYGSVSFTYLRFKSSHSPGMDKLLALFYTAVTSMLNPIIYSLRN       300
D-8.aa      LLVVTLFYGSTSATYLRFKSSHSPGMDKLLALFYTSVTSMLNPIIYSLRN       300

PCR-D.aa    -------------------                                       178
D-9.aa      KDVKAALRRILALKKILSINK                                    321
D-2.aa      KEVKAALRRTLGLKKILSINR                                    321
D-7.aa      KEVKAALRRTLDLKKIMSINR                                    321
D-8.aa      KFVKGALRRTLGLKKVLTMKR                                    321
```

Fig. 16

Spermatid Chemoreceptor G-15

```
                                              TMD 1
MEWLMTEETRNGTLVLEFILEGYPVAEHLKI LFFLLHLLAYLASLMGNML    50

TMD 2
IITITCVDHRLQTPMYFFLSTFSFVECCFITTAIPQLLTIILSGRQKIPF    100

TMD 3
GVCFSQAFVYLVVGATGFFLLAALSLDRFLAICKPLHYPTIMSPRMCFLL    150

TMD 4
VTVCLFLGFLFMASPVVMLSKTFYCGPNIIPHFFCDFGPLANLSCSETRS    200

TMD 5
IEMLFFTLAVIVLFASFLIAIFAYSNIVVTIVRLPSAREROARAFSTCSSH   250

TMD 6                        TMD 7
LIVLSLMYGSCAFIYLKPKQRSRVDTNREAALVNMVVTPLLNPVIYTLRN    300

KQVHQALRDALSRLQLHRYQRRKAPFL                            327
```

Fig. 17

Alignment of SCR G Family: Amino Acid Sequence

```
PCR-G.aa    ------------------------------------------
G-15.aa     MEWLMTKEIKNGTLVLEFIFDRFPVAEHLRILFFLLHLLAYLASLMGNML
G-14.aa     MEWLMTKEIKNGTLVLEFIFDREPVAEHLRILFFLLHLLAYLASLMGNML
G-16.aa     MEWLMTDDTKNGTLVQEFILEGEPVAEHLRILFFLLHMLAYLASSMGNML

PCR-G.aa    ----------------FLSMFSSVECCFITTVIPQLLTIILSGRQKIPF
G-15.aa     IITITCVDHRLQTPMYFFLSMFSSVECCFITTVIPQLLTIILSGRQKIPF
G-14.aa     IITITCVDHRLQTPMYFFLSMFSSVECCFITTVIPQLLTIILSGRQKIPF
G-16.aa     IITYTCVDHRLQTPMYFFLSIIFSFVECCFITTVIPQLLTIILSGRQKIPF

PCR-G.aa    MACISQAFVMLVVGAITGFFLLGVLSLDRFLAICKPLHYPTIMSPRMCFLL
G-15.aa     MACISQAFVMLVVGAITGFFLLGVLSLDRFLAICKPLHYPTIMSPRMCFLL
G-14.aa     MACISQAFVMLVVGAITGFFLLGVLSLDRFLAICKPLHYPTIMSPRMCFLL
G-16.aa     MACFSQAFVMLFIGAVFFLMAVLSLDRFLAICKPLHYPTIMSPRMCFLL

PCR-G.aa    VTVSLVLGFLFMASPVVMLSQSFYCGPNIIPHFFCDFGPLANLSCSETRS
G-15.aa     VTVSLVLGFLFMASPVVMLSQSFYCGPNIIPHFFCDFGPLANLSCSETRS
G-14.aa     VTVSLVLGFLFMASPVVMLSQSFYCGPNIIPHFFCDFGPLANLSCSETRS
G-16.aa     VTVSLVLGFLFMASPVVMLSQSFYCGPNIIPHFFCDFGPLANLSCSETRS

PCR-G.aa    IEMLFFTLAIIVLFASLLIAIFAYSNIVVTIVRLPSARERQRAF------
G-15.aa     IEMLFFTLAIIVLFASLLIAIFAYSNIVVTIVRLPSARERQRAFSTCSSH
G-14.aa     IEMLFFTLAIIVLFASLLIAIFAYSNIVVTIVRLPSARERQRAFSTCSSH
G-16.aa     IEMLFFTLAIIVLFISLLIAIFAYSIIVVTIVRLPSARERQRAFSTCSSH

PCR-G.aa    --------------------------------------------------
G-15.aa     LIVLSLMYGSCAFIYLKPKQRSRVDINREAALVNIVVTPLLNPVIYTLRN
G-14.aa     LIVLSLMYGSCAFIYLKPKQRSRVDINREAALVNIVVTPLLNPVIYTLRN
G-16.aa     LIVLSLMYGSCVFIYLKPKQRSRVDTNREAMLVNMVVTPLLNPVIYTLRN

PCR-G.aa    ---------------------------
G-15.aa     KQVHQALRDALSRVQLHRYQRRHAPSL
G-14.aa     KQVHQALRDALSRVQLHRYQRRHAPSL
G-16.aa     KQVHQALRDALSRVQLHRYQSRKAPLS
```

Fig. 18

Alignment of SCR D 5' RACE Products with D-8: DNA Sequence

```
R500  TGTTTGTAACCATGTAAATTTATGCGTGAGCCCATTCCACAGAGCAGACA  -32
R350  --------------------------------------------------
D-8   --------------------------------------------------

+1
R500  TGTTCTAAAAGAAGAGGGGAAATGCTTAGAGATGAGTGTCAACTGTTCTC  19
R350  -TGTAATAATTTTGTCCTTTCTTTCAGGAGTATGAGTGTCAACTGTTCTC  19
D-8   -TGTAATAATTTTGTCCTTTCTTTCAGGAGTATGAGTGTCAACTGTTCTC  19

R500  TGTGGCAGGAGAATAGTTTGTCTGTCAAACGCTTTGCATTTGCCAAGTTT  79
R350  TGTGGCAGGAGAATAGTTTGTCTGTCAAACGCTTTGCATTCC--------  71
D-8   TGTGGCAGGAGAATAGTTTGTCTGTCAAACGCTTTGCATTTGCCAAGTTC  79

R500  TCTGAGGTCCCTGGAGAATGCTTCCTC                         156
R350  ---------------------------
D-8   TCTGAGGTCCCTGGAGAATGCTTCCTC                         156
```

Fig. 19A

Alignment of SCR D 5' RACE Products with D-8: Amino Acid Sequence

```
                                  +1
R500  CL*PCKFMREPIPQSRHVLKEEGFCLEMSVNCSLWQENSLSVKRFAFAKF  23
R350  --------------QEFL**FCPFFQEMSVNCSLWQENSLSVKRFAF---  20
D-8   --------------QEFL**FCPFFQEMSVNCSLWQENSLSVKRFAFAKF  23

R500  SEVPGECFL                                           32
R350  ---------
D-8   SEVPGECFL                                           32
```

Fig. 19B

SPERM RECEPTORS

This application claims priority to U.S. patent application Ser. No. 08/556,186, which was filed on Nov. 9, 1995, and which has been converted to a provisional application of Ser. No. 60/033,751 filed Sep. 16, 1996.

GOVERNMENT SUPPORT

This invention was made with government support under NIH grant numbers DC 17040, DA 00266, and DA 00074. Therefore, the government has certain rights in this invention.

TECHNICAL FIELD OF THE INVENTION

The present invention pertains to a nucleic acid comprising a sequence that encodes a sperm receptor that is related to, but is different from, a receptor of the odorant receptor family. The present invention also pertains to a method of obtaining a nucleic acid that comprises a sequence that encodes a sperm receptor, as well as a means of using the elements of the invention in a method of contraception, a method of detecting autoimmune infertility, and a method of affecting fertility.

BACKGROUND OF THE INVENTION

During development, spermatozoa exhibit a remarkable capability to respond to environmental cues, which dramatically alter their cell surfaces, transduction cascades, and motility. Spermatozoan development roughly can be divided into four phases, i.e., spermatogenesis, spermiation, ejaculation, and egg interaction. During spermatogenesis, spermatogonia in juxtaposition with Sertoli cells proliferate and differentiate into spermatozoa, and are immotile. In spermiation, sperm are discharged from the testis and acquire the potential for motility as they reach the vas deferens. Upon ejaculation, sperm motility is initiated. Further changes in functional competence and motility occur upon interaction of sperm with the follicular fluid and egg (i.e., in species with internal fertilization), or with water and egg (i.e., in species with external fertilization).

Specific cellular effectors present on the surface of sperm have been implicated at each developmental stage. However, relatively little is known about these receptors that transduce the environmental signals. In comparison, some of the molecular mediators of sperm activation and motility, which interact with the sperm receptors, have been identified.

As reviewed by Ronnett et al., Neuron, 15, 11–16 (1995), sperm developmental studies have revealed roles for environmental ionic composition, calcium, cyclic nucleotides such as cAMP and cGMP, protein modification such as protein phosphorylation and, potentially, protein carboxyl methylation, as well as other factors, at each sperm developmental stage. In particular, these environmental factors, and the cellular receptors with which they interact, have been implicated in the acquisition or exhibition of motility in sperm or sperm precursor cells. Moreover, receptor binding of unidentified chemoattractants appears to affect sperm chemotaxis (or the response of motile cells to a chemical gradient resulting in modulation of the direction of travel so as to approach an attractant or move away from a repellent) and sperm chemokinesis (or a change in swimming speed in response to a chemical stimulus). Both chemotaxis and chemokinesis ostensibly are important in the mammalian sperm-egg interaction.

While relatively little is known about sperm receptors in complex species such as mammals, putative egg peptide receptors have been identified in the sea urchin, *Arbacia punctulata*. Specifically, the sea urchin demonstrates sperm chemotaxis and chemokinesis toward peptides isolated from the jelly layer of the egg. Receptor cross-linking studies reveal binding of the egg peptides to a 77 kD cell-surface receptor, which is related to the LDL receptor, and to a 160 kD cell-surface receptor, which has been shown to be a membrane guanylyl cyclase.

This discovery of a classic component of a plasma membrane-associated signal transduction pathway in sperm provides a molecular basis for the increase in cGMP observed in sea urchin chemotaxis and chemokinesis studies. Moreover, the elucidation of components involved in sperm chemotaxis and chemokinesis, which typically characterize plasma membrane receptor signal transduction pathways, is interesting inasmuch as many of the same signal transduction pathways are activated in olfaction. This suggests that these systems (i.e., the olfactory system, and the sperm receptors and the signal transduction elements with which they interact in transducing environmental signals) may share relevant molecular components.

In terms of the overall design of the peripheral olfactory system, the olfactory cilia are the site of odor recognition and signal transduction. The specialized cilia are found on the dendritic knob in which the bipolar olfactory receptor neuron (i.e., the ORN) terminates at the surface of the neuroepithelium. The ORN is the primary sensory unit of the olfactory system and responds to odorant stimulation with a graded receptor potential, which results in an action potential, if the threshold is attained. The odorants activate adenylyl cyclase to increase cAMP in cilia. Activation occurs only in the presence of GTP, which suggests that the cascade is initiated when the odorants bind to seven transmembrane-spanning domain receptors coupled to guanine nucleotide binding proteins (i.e., G proteins). At least eighteen members of the multigene family that encodes the seven transmembrane domain proteins whose expression is limited to the olfactory epithelium have been identified (Buck et al., *Cell*, 65, 175–87 (1991)). Moreover, other signaling pathways appear to be activated by odorants to permit fine-tuning of the olfactory response. For instance, receptor-mediated stimulation of phospholipase C (PLC) generates inositol 1,4,5-triphosphate ($InsP_3$), which binds to an $InsP_3$ receptor located in the endoplasmic reticulum, resulting in a release of calcium from intracellular stores.

As regarding further similarities between the olfactory system and the sperm signal transduction system, more recent studies confirm that mediators of olfactory desensitization localize to the testis. Specifically, β-ARK-2 and β-arrestin-2, which are isoforms of chemosensory signalling desensitization proteins that are highly specific to olfactory receptor neurons, also are expressed in testis and round spermatids (Dawson et al., *Science*, 259, 825–829 (1993)). In contrast, β-ARK-1 and β-arrestin-1, the most ubiquitous isoforms of these proteins, are absent from both testis (i.e., round spermatids) and olfactory receptor neurons (Dawson et al. (1993), supra). These results confirm that highly specific isoforms of chemosensory signaling desensitization proteins are shared between olfactory receptor neurons and mature sperm.

Other studies similarly confirm the existence of odorant receptors in the male germ line, particularly in spermatocytes and spermatids (Parmentier et al., *Nature*, 355, 453–456 (1992); and Vanderhaeghen et al., *J. Cell Biology*, 123(6) 1441–1452 (1993)). Moreover, subcellular localization studies demonstrate that olfactory receptors and signal transduction proteins colocalize to the midpiece of mammalian sperm (Walensky et al., *Molecular Medicine*, 1(2), 130–141 (1995)). The respiratory center of the sperm is located in the tail midpiece, in close proximity to mitochondria and microtubule origins, and, thus, this region likely contains important signal transduction proteins. Accordingly, these results are consistent with a role for odorant receptors in transducing chemotactic signals in sperm.

Clearly, there is a need for a more thorough understanding of the response of spermatozoa to environmental cues, as effected by sperm receptors. Cloning of these sperm receptors can facilitate the understanding of the mechanism of sperm chemosensing by allowing production and further study of the receptors, as well as isolation of additional sperm receptors. Such production will enable, inter alia, identification of those ligands that interact with the receptors. This is advantageous, inasmuch as the ligands that bind to sperm can be difficult to isolate and analyze (e.g., due to their presence in very small amounts, or in gradients, which can vary only slightly, to effect a response). Moreover, it will allow manipulation of the sperm via manipulation of the receptor, e.g., as a means of contraception, and will provide a means of detecting autoimmune infertility.

Thus, there remains a need for a source of sperm receptors, to facilitate the further study of these receptors, as well as to identify additional receptors and ligands that bind to the receptors. There also remains a need for ways to alter the behavior of sperm, e.g., for use in contraception, and a need for a way to detect autoimmune infertility. Furthermore, there remains a need for a method to obtain a nucleic acid molecule that comprises a sequence that encodes a sperm receptor. The present invention provides nucleic acids encoding sperm receptors, thus remedying these needs. These and other objects and advantages of the present invention, as well as additional inventive features, will be apparent from the description of the invention set forth herein.

BRIEF SUMMARY OF THE INVENTION

The present invention provides a nucleic acid comprising a sequence encoding a sperm receptor that is related to, but is different from, a receptor of the odorant receptor family. The present invention also provides a method of obtaining a nucleic acid encoding a sperm receptor. Furthermore, the invention provides a means of using the elements further described herein in a method of contraception, a method of detecting autoimmune infertility, and a method of affecting fertility.

BRIEF DESCRIPTION OF THE DRAWINGS

FIG. 2 depicts the nucleic acid sequence [SEQ ID NO:5] present within the D class sperm receptor clone D-2. "N" stands for any nucleotide (i.e., A, C, G, T or U).

FIG. 3 depicts the nucleotide acid sequence [SEQ ID NO:6] present within the D class sperm receptor clone D-7. "N" stands for any nucleotide (i.e., A, C, G, T or U).

FIG. 4 depicts the nucleic acid sequence [SEQ ID NO:7] present within the D class sperm receptor clone D-8.

FIG. 5 depicts the nucleic acid sequence [SEQ ID NO:8] present within the D class sperm receptor clone D-9.

FIG. 6 depicts the nucleic acid sequence [SEQ ID NO:9] present within the D class sperm receptor clone G-X.

FIG. 7 depicts the predicted amino acid sequence [SEQ ID NO:10] present within the D class sperm receptor clone D-2. The asterisk represents the termination of the amino acid sequence due to a termination codon in the nucleic acid sequence.

FIG. 8 depicts the predicted amino acid sequence [SEQ ID NO:11] present within the D class sperm receptor clone D-7. The asterisk represents the termination of the amino acid sequence due to a termination codon in the nucleic acid sequence.

FIG. 9 depicts the predicted amino acid sequence [SEQ ID NO:12] present within the D class sperm receptor clone D-8. The asterisk represents the termination of the amino acid sequence due to a termination codon in the nucleic acid sequence.

FIG. 10 depicts the predicted amino acid sequence [SEQ ID NO:13] present within the D class sperm receptor clone D-9. The asterisk represents the termination of the amino acid sequence due to a termination codon in the nucleic acid sequence.

FIG. 11 depicts the predicted amino acid sequence [SEQ ID NO:14] present within the D class sperm receptor clone G-X. The asterisk represents the termination of the amino acid sequence due to a termination codon in the nucleic acid sequence.

FIG. 12 depicts the conservation of the amino acid sequences present within the "D" type sperm receptor clones D-8 (A), D-9 (B), D-2 (C), and D-7 (D).

FIG. 13 depicts the nucleic acid sequence [SEQ ID NO:15] used to generate an antibody against a D class sperm receptor. The sequence corresponds to the first 96 base pairs of the D-9 sperm receptor nucleic acid sequence.

FIG. 14 depicts the amino acid sequence [SEQ ID NO:16] of a D class sperm receptor against which an antibody was generated. The sequence corresponds to the first 32 amino acids of the predicted D-9 amino acid sequence.

FIG. 15 depicts the predicted amino acid sequence [SEQ ID NO:10] present within the D-class sperm receptor clone D-2, and delineates the seven transmembrane domains (TMD1–7) by bars drawn over the amino acid sequence.

FIG. 16 depicts the aligned amino acid sequences of pSCR D [SEQ ID NO:17], SCR D-2 [SEQ ID NO:18], D-7 [SEQ ID NO:19], D-8 [SEQ ID NO:20], and D-9 [SEQ ID NO:13]. The regions of amino acid identity are shaded and boxed.

FIG. 17 depicts the predicted amino acid sequence [SEQ ID NO:14] present within the G-class sperm receptor clone G-15, and delineates the seven transmembrane domains (TMD1–7) by bars drawn over the amino acid sequence.

FIG. 18 depicts the aligned amino acid sequences of pSCR G [SEQ ID NO:21], SCR G-14 [SEQ ID NO:22], G-15 [SEQ ID NO:23], and G-16 [SEQ ID NO:24]. The regions of amino acid identity are shaded and boxed.

FIG. 19A depicts the alignment of the nucleotide sequences of two SCR D cDNA species, which are designated R500 [SEQ ID NO:25] and R350 [SEQ ID NO:26], with the nucleotide sequence of SCR D-8 [SEQ ID NO:27].

FIG. 19B depicts the alignment of the predicted amino acid sequences of the two SCR D cDNA species R500 [SEQ ID NO:28] and R350 [SEQ ID NO:29] with the amino acid sequence of SCR D-8 [SEQ ID NO:30].

DETAILED DESCRIPTION OF THE PRESENT INVENTION

Figure 1:
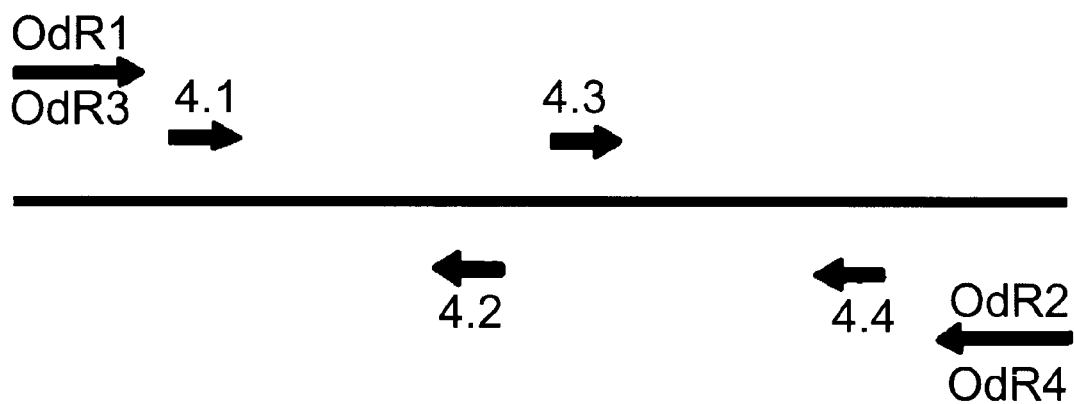
FIG. 1 depicts the nested primer design employed for obtaining the D class sperm receptor clones of the present invention. A similar design was employed for obtaining the G class sperm receptor clones.

The present invention provides an enriched or isolated nucleic acid comprising a sequence that encodes a sperm receptor that is related to, but is different from, a receptor of the odorant receptor family, as further defined herein.

Sperm Receptor Nucleic Acid

The term "nucleic acid" as employed herein refers to a polymer of DNA or RNA that can be single- or double-stranded, and, optionally, can contain synthetic, nonnatural, or modified nucleotides, which are capable of being incorporated into DNA or RNA polymers. A DNA polynucleotide can be comprised of genomic or cDNA sequences. The nucleic acid is "enriched" in that the concentration of the material is at least about 2, 5, 10, 100, or 1,000 times its natural concentration (i.e., if isolated from nature; otherwise, generated anew), for example, advantageously at least about 0.01% by weight, and preferably, at least about 0.1% by weight. Enriched preparations of at least about 0.5%, 1%, 5%, 10%, and 20% by weight also are contemplated. The nucleic acid is "isolated" in that the material has been removed from its original environment, e.g., the natural environment, if naturally occurring, or is produced from a naturally occurring substance. For example, a naturally occurring polynucleotide present in a living animal is not isolated, but the same polynucleotide, separated from some or all of the coexisting materials in the natural system, or reverse transcribed into cDNA, is isolated. It is also advantageous that the nucleic acids be purified, wherein "purified" does not mean absolute purity but, rather, relative purity.

Preferably, the "sperm receptor" nucleic acid is that of an animal, including, but not limited to, an amphibian, bird, fish, insect, reptile, or mammal. Optimally, the sperm receptor nucleic acid is that of a mammal, for instance, that of a rodent, an ape, a chimpanzee, a feline, a canine, an ungulate (such as ruminant or swine) as well as, in particular, that of a human.

As defined herein, "a receptor of the odorant receptor family" encompasses receptors that comprise the odorant or olfactory receptor superfamily as set out by Buck et al. (e.g, the seven transmembrane-spanning domain proteins whose expression is limited to the olfactory epithelium; Buck et al. (1991), supra) or receptors that are produced (i.e., transcribed and/or translated) in olfactory tissue. Such olfactory or odorant receptors also can be produced (i.e., transcribed and/or translated) in other tissues or cells as well.

"Related to, but different from" means the nucleic acid sequences encoding the sperm receptors of the present invention are more related to each other than they are to a nucleic acid sequence encoding a receptor of the odorant receptor family. Relatedness can be measured in terms of homology, and, as described herein, means that the polypeptide sequences that the sperm receptors encode demonstrate homology (i.e., the existence of regions of conserved amino acids), but not identity (i.e., complete or 100% homology), with the polypeptide sequences of odorant receptors. As defined herein, a "polypeptide" is a linear polymer of more than ten amino acids that are linked by peptide bonds (e.g., is a protein). Preferably, the polypeptide sequence encoded by the sperm receptor nucleic acid sequence is about 40% to about 50% homologous (i.e., at the amino acid level) to a receptor of the odorant receptor family. There is complete or 100% homology, for instance, at a particular amino acid residue, when the amino acids of sequences being compared are the same or represent a conservative amino acid substitution. A "conservative amino acid substitution" is an amino acid substituted by an alternative amino acid of similar charge density, hydrophilicity/hydrophobicity, size and/or configuration (e.g., Val for Ile). A "nonconservative amino acid substitution" is an amino acid substituted by an alternative amino acid of differing charge density, hydrophilicity/hydrophobicity, size and/or configuration (e.g., Val for Phe).

Optimally, such a nucleic acid encoding a sperm receptor, which is about 40% to about 50% homologous at the amino acid level to a receptor of the odorant receptor family, exhibits a pattern of tissue-specific expression that differs from said receptor of the odorant receptor family. Optimally, the sperm receptor nucleic acid is expressed predominantly and, most preferably, exclusively, in sperm.

Moreover, the invention preferably also provides an enriched or isolated nucleic acid comprising a sequence that encodes a sperm receptor that is about 20% to about 30% homologous at the amino acid level to a receptor of the odorant receptor family, and that exhibits a pattern of tissue-specific expression that differs from said receptor of the odorant receptor family. Desirably, the sperm receptor nucleic acid is expressed primarily, and preferably, exclusively, in sperm.

Relatedness also can be measured in terms of the ability of single strands of the nucleic acid to hybridize (i.e., form double-helical segments) under defined conditions, using a standard hybridization assay (e.g., as described by Sambrook et al., *Molecular Cloning, A Laboratory Manual*, 2nd ed. (Cold Spring Harbor Laboratory, Cold Spring Harbor, N.Y., 1989)). Preferably, the sperm receptor nucleic acid sequence demonstrates hybridization to a probe comprising a conserved region of an olfactory receptor coding sequence under relatively highly stringent conditions, as that term is understood by one skilled in the art. For instance, preferably, the hybridization is carried out using a standard hybridization buffer at a temperature ranging from about 50° C. to about 75° C., even more preferably from about 60° C. to about 70° C., and optimally from about 65° C. to about 68° C. Alternately, formamide can be included in the hybridization reaction, and the temperature of hybridization can be reduced to preferably from about 35° C. to about 45° C., even more preferably from about 40° C. to about 45° C., and optimally to about 42° C. Desirably, formamide is included in the hybridization reaction at a concentration of from about 30% to about 50%, preferably from about 35% to about 45%, and optimally at about 40%. Moreover, optionally, the hybridized sequences are washed (if necessary to reduce non-specific binding) under relatively highly stringent conditions, as that term is understood by those skilled in the art. For instance, desirably, the hybridized sequences are washed one or more times using a solution comprising salt and detergent, preferably at a temperature of from about 50° C. to about 75° C., even more preferably at from about 60° C. to about 70° C., and optimally from about 65° C. to about 68° C. Preferably, a salt (e.g., such as sodium chloride) is included in the wash solution at a concentration of from about 0.01 M to about 1.0 M. Optimally, a detergent (e.g., such as sodium dodecyl sulfate) is also included at a concentration of from about 0.01% to about 1.0%.

Preferably, the probe employed for hybridization to identify sperm receptors (i.e., the "probe comprising a conserved region of an olfactory receptor coding sequence") comprises the sequence of SEQ ID NO:1 (i.e., the OdR1 primer), SEQ ID NO:2 (i.e., the OdR2 primer), SEQ ID NO:3 (i.e., the OdR3 primer), or SEQ ID NO:4 (i.e., the OdR4 primer). When such a probe was employed, and as further described herein, several clones comprising sperm receptors were identified and isolated. These clones include the D class receptor clones D-2, D-7, D-8, and D-9, and the G class receptor clone G-X. Thus, preferably, the present invention provides an enriched or isolated nucleic acid comprising a sequence selected from the group consisting of SEQ ID NO:5 (i.e., comprising the nucleotide sequence contained in the D-2 clone), SEQ ID NO:6 (i.e., comprising the nucleotide sequence contained in the D-7 clone), SEQ ID NO:7 (i.e., comprising the nucleotide sequence contained in the D-8 clone), SEQ ID NO:8 (i.e., comprising the nucleotide sequence contained in the D-9 clone), and SEQ ID NO:9 (i.e., comprising the nucleotide sequence contained in the G-X clone).

The use of antisense technology and gene modification are well known to those skilled in the art. Accordingly, the present invention preferably also provides an enriched or isolated nucleic acid comprising a sequence, which is complementary to, or substantially equivalent to, a sequence selected from the group consisting of SEQ ID NO:5, SEQ ID NO:6, SEQ ID NO:7, SEQ ID NO:8, and SEQ ID NO:9.

A "complementary sequence" is a sequence, the base sequence of which is related to the base sequence in another nucleic acid molecule by the base-pairing rules. A "substantially equivalent" sequence is a sequence that varies from a sperm receptor sequence by one or more substitutions, deletions, or additions, the effect of which may or may not result in a difference in the sequence at the amino acid level, and does not result in an undesirable functional dissimilarity between the two sequences (i.e., the polypeptide which results from the substantially equivalent sequence has the binding activity characteristic of the sperm receptor that was modified). Techniques for constructing and screening libraries of polypeptide sequences to identify polypeptides that specifically bind to a given protein are known (see, e.g., Scott et al., Science, 249, 386–390 (1990), and others).

A difference in a nucleotide sequence, which does not result in a difference at the amino acid level, can include modifications that result in conservative amino acid substitutions, as well as DNA sequence differences due to the degeneracy of the genetic code, i.e., the fact that different nucleic acid sequences can code for the same protein or peptide. A difference in sequence at the amino acid level (i.e., due to a difference in the nucleotide sequence) can include single amino acid substitution (preferably, a conservative substitution), deletion, and/or insertion, or a plurality of amino acid substitutions, deletions, and/or insertions, wherein the resulting polypeptide is still recognizable as related to the sperm receptor as defined by binding activity. Moreover, a difference in sequence at the amino acid level also can include those amino acid sequence differences that result in a polypeptide of altered size, such as a larger protein, or a truncated protein. The means of making such modifications are well known in the art, and also can be accomplished by means of commercially available kits and vectors (e.g., New England Biolabs, Inc., Beverly, Mass.; and Clontech, Palo Alto, Calif.).

The enriched or isolated nucleic acid, which comprises the complementary sequence, or the substantially equivalent sequence, can be identified by hybridization under relatively highly stringent conditions to a probe comprising a region of a sperm receptor nucleic acid sequence, or some part thereof, e.g., either the entirety or a portion of the nucleic acid sequence of SEQ ID NO:5, SEQ ID NO:6, SEQ ID NO:7, SEQ ID NO:8 or SEQ ID NO:9. As defined herein, a "probe" is a molecule (i.e., a DNA fragment, cDNA fragment or oligonucleotide) that is labeled in some fashion (e.g., with a radioactive isotope) and used to identify or isolate a gene or cDNA, or a fragment thereof. When only a portion of any of these nucleic acid sequences is employed as a probe, preferably that portion comprises a sequence of from about 1 to about 500 base pairs, more preferably from about 1 to about 100 base pairs, and most preferably from about 1 to about 50 base pairs.

Moreover, further sperm receptors (i.e., either previously unidentified sperm receptors, or sperm receptors from different species) can be identified using as a probe under relatively highly stringent conditions either the entirety or a portion of the nucleic acid sequence of SEQ ID NO:5, SEQ ID NO:6, SEQ ID NO:7, SEQ ID NO:8 or SEQ ID NO:9. Optimally, such a probe is derived from regions of the sperm receptor nucleic acid sequences that demonstrate commonality with other sperm receptors at the amino acid level, i.e., regions corresponding to polypeptide sequences that fall within the "boxed" sequences in FIG. 12 (e.g., corresponding to residues 3–13, 18–34; etc.).

Thus, the invention provides a method of obtaining a nucleic acid comprising a sequence, or a portion thereof, that encodes a sperm receptor that is related to, but is different from, a receptor of the odorant receptor family. This method comprises hybridizing (preferably under relatively high stringency conditions) a cDNA or genomic DNA library with a probe comprised of a portion, or the entirety, of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9, and isolating a host or vector (i.e., depending on the form of the library) comprising the sperm receptor nucleic acid.

According to this invention, a "genomic DNA library" is a clone library, which contains representative nucleotide sequences from all sections of the DNA of a given genome. It is constructed using various techniques that are well known, for instance, by enzymatically or mechanically fragmenting the DNA from an organism, organ, or tissue of interest, linking the fragments to a suitable vector, and introducing the vector into appropriate cells so as to establish the genomic library. A genomic library contains both transcribed DNA fragments as well as nontranscribed DNA fragments.

In comparison, a "cDNA library" is a clone library that differs from a gene library in that it contains only transcribed DNA sequences (i.e., exons) and no nontranscribed sequences (e.g., introns, spacer DNA; etc.). It is established using techniques that are well known in the art, i.e., making cDNA from a population of cytoplasmic mRNA molecules using the enzyme RNA-dependent DNA polymerase (i.e., reverse transcriptase), converting the single-stranded DNA into double-stranded DNA, cloning the resultant molecules into a vector, and introducing the vector into appropriate cells so as to establish the cDNA library. Alternately, a cDNA library need not be cloned into a vector and/or established in cells, but can be screened using PCR with gene-specific primers. A "primer" is a short, single stranded RNA or DNA segment that functions as the starting point for the polymerization of nucleotides. Generally speaking, the primers according to the present invention preferably fall within the same size constraints as the probes of the invention. If a desired PCR product is generated by PCR using gene-specific primers, the amplified fragment can be cloned directly, e.g., using a commercially available PCR cloning system, such as a T/A Cloning System (Clontech, Palo Alto, Calif.) or other commercially available system. Similarly, such a cDNA library can be used as a template for rapid amplification of cDNA ends (i.e., RACE) using a combination of primers.

Thus, the invention provides a further method of obtaining a nucleic acid comprising a sequence that encodes a sperm receptor that is related to, but is different from, a receptor of the odorant receptor family. This method comprises: (1) preparing one or more primers from a portion of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9; and (2) using PCR or other suitable means to screen a cDNA library and generate said nucleic acid, or a portion thereof. These methods are further described in the Examples that follow.

Vector

The present invention provides a vector, which comprises a nucleic acid comprising a sequence encoding a sperm receptor that is related to, but is different from, a receptor of the odorant receptor family. The vector utilized in the context of the present invention can comprise sequences so as to constitute any type of suitable vector appropriate for introduction into cells. For instance, the vector can comprise an expression vector, a vector in which the coding sequence of the sperm receptor is under the control of its own cis-acting regulatory elements, a vector designed to facilitate gene integration or gene replacement in host cells, and the like.

Thus, according to the invention, a "vector" encompasses a DNA molecule, such as a plasmid, bacteriophage, phagemid, virus or other vehicle, which contains one or more heterologous or recombinant DNA sequences, e.g., a sperm receptor gene or sperm receptor coding sequence of interest under the control of a functional promoter and, possibly, also an enhancer, and that is capable of functioning as a vector as that term is understood by those of ordinary skill in the art. Appropriate phage and viral vectors include, but are not limited to, lambda (8) bacteriophage, EMBL bacteriophage, simian virus 40, bovine papilloma virus, Epstein-Barr virus, adenovirus, herpes virus, vaccinia virus, Moloney murine leukemia virus, Harvey murine sarcoma virus, murine mammary tumor virus, and Rous sarcoma virus.

Reference to a vector or DNA sequences contained therein as "recombinant" merely acknowledges the linkage of DNA sequences that are not typically conjoined as isolated from nature. A "gene" is any nucleic acid sequence coding for a protein or a nascent mRNA molecule. Whereas a gene comprises coding sequences plus any noncoding (e.g., regulatory) sequences, a "coding sequence" does not include any noncoding DNA. A "promoter" is a DNA sequence that directs the binding of RNA polymerase and, thereby, promotes RNA synthesis. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

Preferably, a vector according to the invention is compatible with the cell into which it is introduced, e.g., is capable of imparting expression on the cell of the sperm receptor gene or coding sequence, and is stably maintained or relatively stably maintained in the host cell. Desirably, the vector comprises an origin of replication functional in the cell. When a sperm receptor coding sequence is transferred (i.e., as opposed to a sperm receptor gene having its own promoter), optimally the vector also contains a promoter that is capable of driving expression of the coding sequence and that is operably linked to the coding sequence. A coding sequence is "operably linked" to a promoter (e.g., when both the coding sequence and the promoter together constitute a native or recombinant sperm receptor gene) when the promoter is capable of directing transcription of the coding sequence.

In a recombinant vector of the present invention, preferably all the proper transcription (e.g., initiation and termination signals), translation (e.g., ribosome entry or binding site and the like) and processing signals (e.g., splice donor or acceptor sites, if necessary, and polyadenylation signals) are arranged correctly on the vector, such that the sperm receptor gene or coding sequence will be appropriately transcribed and translated in the cells into which it is introduced. The manipulation of such signals to ensure appropriate expression in host cells is well within the knowledge and expertise of the ordinary skilled artisan. Whereas a sperm receptor gene is controlled by (i.e., operably linked to) its own promoter, another promoter, including a constitutive promoter, such as, for instance the adenoviral type 2 (Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, including promoters appropriate for expression in prokaryotic cells, can be employed to command expression of the sperm receptor coding sequence.

Alternately, a tissue-specific promoter (i.e., a promoter that is preferentially activated in a given tissue and results in expression of a gene product in the tissue where activated) can be used in the vector when employed for expression in an animal host, or in cells, tissues or organs of the host. Such promoters include, but are not limited to, the elastase I gene control region, which is active in pancreatic acinar cells as described by Swift et al. (*Cell*, 38, 639–646 (1984)) and MacDonald (*Hepatology*, 7, 425–515 (1987)). Similarly, a promoter that is selectively activated at a particular developmental stage can be employed, e.g., globin genes are transcribed differentially in embryos and adults. Another option is to use an inducible promoter, such as the IL-8 promoter, which is responsive to TNF, or to use other similar promoters responsive to other factors present in a host or that can be administered exogenously. According to the invention, any promoter can be altered by mutagenesis, so long as it has the desired binding capability and promoter strength.

Preferably, the vector also comprises some means by which the vector or its contained subcloned sequences can be identified and selected. Vector identification and/or selection can be accomplished using a variety of approaches known to those skilled in the art. For instance, vectors containing particular genes or coding sequences can be identified by hybridization, the presence or absence of so-called "marker" gene functions encoded by marker genes present on the vectors, and/or the expression of particular sequences. In the first approach, the presence of a particular sequence in a vector can be detected by hybridization (e.g., by DNA-DNA hybridization) using probes comprising sequences that are homologous to the relevant sequence. In the second approach, the recombinant vector/host system can be identified and selected based upon the presence or absence of certain marker gene functions, such as resistance to antibiotics, thymidine kinase activity, and the like, caused by particular genes encoding these functions present on the vector. In the third approach, vectors can be identified by assaying for a particular gene product encoded by the vector. Such assays can be based on the physical, immunological, or functional properties of the gene product.

Accordingly, the present invention preferably provides a vector comprising a nucleic acid comprising a sequence encoding a sperm receptor that is about 40% to about 50% homologous (i.e., at the amino acid level) to a receptor of the odorant receptor family. The invention further preferably provides a vector comprising a nucleic acid selected from the group consisting of SEQ ID NO:5, SEQ ID NO:6, SEQ ID NO:7, SEQ ID NO:8, and SEQ ID NO:9.

A vector according to the present invention can be introduced into any suitable host cell, whether eukaryotic or prokaryotic. Suitable prokaryotic host cells include, but are not limited to, *Escherichia coli, Bacillis subtilis, Pseudomonas aeruginosa*, and members of the genus Salmonella (e.g., *S. typhimurium, S. typhi, S. enteritidis*, and the like). Preferably, a prokaryotic host cell is avirulent. Suitable eukaryotic host cells include, but are not limited to, rodent or mouse cells, *Saccharomyces cerevislae*, and, particularly, human cells. Preferably, the vector comprises an expression vector appropriate for expression of a sperm receptor gene or coding sequence in a human or rat cell, or, alternately, in an *E. coli* cell. The isolation of such cells, and/or the maintenance of such cells or cell lines derived therefrom in culture, has become a routine matter, and one in which the ordinary skilled artisan is well versed.

The form of the introduced vector can vary with the rationale underlying the introduction of the vector into the host cell. For example, the nucleic acid can be closed circular, nicked, or linearized, depending on whether the vector is to be maintained extragenomically (i.e., as an autonomously replicating vector), integrated as a provirus or prophage, transiently transfected, transiently infected as with use of a replication-deficient or conditionally replicating virus or phage, or stably introduced into the host genome through double or single crossover recombination events.

Any appropriate means of introducing the vector into a host cell can be employed. In the case of prokaryotic cells, vector introduction can be accomplished, for instance, by electroporation, transformation, transduction, conjugation or triparental mating. For eukaryotic cells, vectors can be introduced through the use of, for example, electroporation, transfection, infection, membrane fusion with liposomes, high velocity bombardment with DNA-coated microprojectiles, incubation with calcium phosphate-DNA precipitate, direct microinjection into single cells, and the like. Other methods are available and are known to those skilled in the art.

Thus, the present invention provides a host cell, wherein the cell has been modified by introduction of a vector comprising a nucleic acid comprising a sequence encoding a sperm receptor that is about 40% to about 50% homologous (i.e., at the amino acid level) to a receptor of the odorant receptor family, as further described herein. The invention further provides a preferred host cell, which comprises a vector comprising a nucleic acid selected from the group consisting of SEQ ID NO:5, SEQ ID NO:6, SEQ ID NO:7, SEQ ID NO:8, and SEQ ID NO:9.

Sperm Receptor Polypeptide

The introduction of a vector according to the present invention into a host cell also provides a method of producing a sperm receptor polypeptide. Specifically, the vector can be used to express a double-stranded DNA sequence, which is transcribed and translated in the host cell into a polypeptide. The expression host is maintained under conditions whereby the host cell produces a sperm receptor. In other words, the host is grown in an appropriate nutrient medium, such as is known to those skilled in the art, under conditions such that the desired polypeptide is produced in the cells.

In particular, this method preferably comprises introducing into a host cell a vector comprising a nucleic acid comprising a sequence encoding a sperm receptor that is about 40% to about 50% homologous (i.e., at the amino acid level) to a receptor of the odorant receptor family. Moreover, the method comprises introducing into a host cell a vector comprising a nucleic acid selected from the group consisting of SEQ ID NO:5, SEQ ID NO:6, SEQ ID NO:7, SEQ ID NO:8, and SEQ ID NO:9.

The polypeptide products that can be obtained by this method are isolated in substantially pure form. Notably, a polypeptide can be obtained that is free of cellular debris, which can include such contaminants as, for instance, proteins, polysaccharides, lipids, nucleic acids, viruses, bacteria, fungi, and combinations thereof.

Thus, the present invention preferably provides an enriched or isolated polypeptide comprising an amino acid sequence encoded by a nucleic acid comprising a sequence encoding a sperm receptor that is about 40% to about 50% homologous (i.e., at the amino acid level) to a receptor of the odorant receptor family.

The invention also preferably provides an enriched or isolated polypeptide comprising an amino acid sequence encoded by a nucleic acid comprising a sequence selected from the group of sequences consisting of SEQ ID NO:5, SEQ ID NO:6, SEQ ID NO:7, SEQ ID NO:8, and SEQ ID NO:9. Even more preferably, the present invention provides an enriched or isolated polypeptide comprising a polypeptide selected from the group of polypeptides consisting of SEQ ID NO:10, SEQ ID NO:11, SEQ ID NO:12, SEQ ID NO:13, and SEQ ID NO:14.

Illustrative Uses

The availability of clones encoding sperm receptors provides a means of producing large quantities of sperm receptor polypeptides, and sources for probes that can be used to identify and isolate more sperm receptor nucleic acid sequences, as well as to study the expression and regulation of the sperm receptor genes. In addition, these sequences can be used in antisense approaches to inhibit the transcription or translation of endogenous sperm receptors, as previously described.

However, there are further uses for sperm receptor polypeptides, or immunologically active fragments thereof, which are produced in accordance with the present invention. For instance, the polypeptides can be employed as means of detecting autoimmune infertility due to circulating antibodies directed against the sperm receptor.

This is based upon the fact that, in the normal physiological condition, the immune system does not respond to sperm, egg, or fetus. Moreover, the sperm receptor polypeptides also can be used as vaccines, as a means of fertility control. This latter approach has a few important advantages as compared with anti-egg or anti-fetus immunocontraception, and as compared with traditional means of contraception. First, it would work in both males and females. Second, use of a sperm-specific protein for immunization in a female does not raise any problems of autoimmunity. Furthermore, sperm receptor polypeptides can be employed to modulate sperm receptor binding, and in this fashion, can affect fertility, or contribution to fertility.

The methods can be used in any animal, including, but not limited to, an amphibian, bird, fish, insect, reptile, or mammal. One or more of the methods may have particular utility in humans, domestic animals (e.g., cow, pigs, sheep or horses, as well as cats and dogs), and in common pests (i.e., insects or rodents).

Accordingly, the present invention provides antigenic polypeptides (also referred to herein as "antigens") that can be used as an immunocontraceptive agent, or for the diagnosis of autoimmune infertility, as further described herein. The antigenic polypeptides preferably comprise (1) the entirety of the polypeptides of SEQ ID NO:10 through SEQ ID NO:14; (2) fragments of the polypeptides of SEQ ID NO:10 through SEQ ID NO:14, which desirably are from about 5 to about 50 amino acids in length and, optimally, are less than about 30 amino acids in length; (3) a modified fragment comprising the aforementioned fragment that has been modified by the replacement of one or more amino acid residues, as previously described; or (4) a longer polypeptide, which comprises the aforementioned fragment and further comprises a carrier protein attached to the C- or N-terminal end of the sequence. The sizes of carrier proteins can vary; such proteins are well known to those skilled in the art.

One antigenic polypeptide according to the invention is that comprised of a polypeptide having the amino acid sequence of SEQ ID NO:16, which is derived from the nucleic acid sequence of SEQ ID NO:15. Longer polypeptides can also include this sequence, as well as other sequences contained in SEQ ID NO:10 through SEQ ID NO:14. Generally, however, longer polypeptides must provide the sequence in an exposed portion of the molecule, and not where it is sequestered from antibody binding. Furthermore, polypeptides that can be used to carry out the invention include analogs of such polypeptides. As described herein, an "analog" is a polypeptide which, while not having identity to the sequence of a sperm receptor as described herein, has a similar three-dimensional structure. An analog can be obtained, as previously described, by modification of the nucleic acid sequence that encodes the sperm receptor to which the analog is related.

The invention, thus, also provides an immunocontraceptive method, which comprises administering to a subject (e.g., a female subject) an antigen as described above in an amount sufficient to stimulate an immune response, and reduce the fertility of the subject. Preferably, however, the method can be employed with male subjects, i.e., as a novel male-oriented means of contraception, to reduce the ability of the subject to contribute to fertilization. Further, this immunocontraceptive method preferably comprises administering to a subject a polypeptide comprising an amino acid sequence encoded by a nucleic acid comprising a sequence selected from the group consisting of SEQ ID NO:5, SEQ ID NO:6, SEQ ID NO:7, SEQ ID NO:8, and SEQ ID NO:9, optimally, in an amount sufficient to reduce the fertility, or contribution to fertility, of the subject.

The invention also accordingly provides an immunocontraceptive vaccine formulation comprising an antigen as described above, optimally in an amount that is sufficient to reduce the fertility, or contribution to fertility, of a subject, and in combination with a pharmaceutically acceptable carrier. According to the invention, and as further described below, a "pharmaceutically acceptable carrier" includes any physiologically acceptable vehicle, generally distilled water, phosphate-buffered saline, physiological saline, buffers containing SDS or EDTA, and the like. Preferably, various adjuvants, such as aluminum hydroxide, MTP in saline, Freund's complete or incomplete adjuvant, and Tween 80, are included in the vaccine formulation.

A preferred immunocontraceptive vaccine formulation according to the invention comprises a polypeptide comprising an amino acid sequence encoded by a nucleic acid comprising a sequence selected from the group consisting of SEQ ID NO:5, SEQ ID NO:6, SEQ ID NO:7, SEQ ID NO:8, and SEQ ID NO:9, optimally, in an amount sufficient to reduce the fertility, or contribution to fertility, of the subject, and a pharmaceutically acceptable carrier.

Similarly, a sperm receptor nucleic acid sequence can be joined with other sequences (for instance, to increase its immunogenicity), such as viral sequences, e.g., such as those of baculovirus, vaccinia virus, and adenovirus, for use in vaccination. The DNA sequence of the sperm receptor can be inserted into a virus at a site where it can be expressed, so as to provide an antigen of the sperm receptor to be recognized as an immunogen by the vaccinated subject. Alternately, the sperm receptor coding sequence can be genetically conjugated to other proteins so as to form protein fusions.

As part of the invention, also provided is a host cell (preferably, an avirulent host cell) that contains a recombinant DNA sequence encoding a sperm receptor, and that is capable of expressing the encoded DNA sequence. The invention, thus, further preferably provides an immunocontraceptive vaccine formulation comprising a host cell that comprises a vector, which comprises a nucleic acid comprising a sequence selected from the group consisting of SEQ ID NO:5, SEQ ID NO:6, SEQ ID NO:7, SEQ ID NO:8, and SEQ ID NO:9, optimally, in an amount sufficient to reduce the fertility, or contribution to fertility, of the subject, and a pharmaceutically acceptable carrier.

As previously indicated, the invention further provides a means of screening for autoimmune infertility in a subject (i.e., in a male or female subject). This method comprises detecting the presence in the subject of antibodies, which bind to a polypeptide antigen as described above, and wherein the presence of such antibodies is indicative of autoimmune infertility.

Such a method can be carried out by a variety of means known to those skilled in the art. Basically any conventional procedure that can be employed for detecting antibodies can be used, using the sperm receptor polypeptide. Such conventional procedures include, but are not limited to, sperm agglutination and precipitation assays, radioimmunoassays, enzyme immunoassays, and the like, as further described in International Application WO 95/15764.

Preferably, antibodies are detected using a sample of whole blood (or serum isolated therefrom) from a subject to be tested. The serum is placed in contact with an antigenic polypeptide, as previously described, under conditions such that the antigen is able to interact and bind to any antibodies present in the sample. The antigen can be bound to a solid support, or can be employed free in solution (e.g., as with certain types of immunoassay). The antigenic polypeptide can be bound to the support using techniques well known in the art, e.g., attachment by means of a bifunctional organic molecule, followed by cross-linking, if necessary. The solid support can comprise plastic, fiberglass, nitrocellulose, and the like.

In one embodiment, the antigenic polypeptide, as bound to the antibody of interest, is deleted, e.g., through a reporter group attached to the antigenic polypeptide. In another embodiment, the antibody to be detected is allowed to interact with the polypeptide antigen, which may or may not be bound to a solid support. Subsequently, a second antibody is added, which is capable of binding to the antibody that may be present in the subject's sample. For instance, the second antibody can be an immunoglobulin antibody that is directed against antibodies of the species of subject from which the sample was obtained. The second antibody can be conjugated to any suitable reporter group that allows detection of the second antibody. For instance, the reporter group can be an enzyme that can be detected in the presence of its substrate (e.g., in particular, horseradish peroxidase can be detected in the presence of o-phenylenediamine), a fluorescent group, a radioactive group, and any other such group, which can be employed in an immunoassay. The presence of antibody in the subject's sample can then be detected and, optionally, the amount of antibody present in the subject's sample can be quantitated, by adding a substrate for the reporter group present on the second antibody, or by other means of detecting, and, preferably, quantitating the reporter group.

In particular, the invention provides a method of screening for autoimmune infertility, which comprises detecting the presence of antibodies that bind to a polypeptide comprising an amino acid sequence encoded by a nucleic acid comprising a sequence selected from the group consisting of SEQ ID NO:5, SEQ ID NO:6, SEQ ID NO:7, SEQ ID NO:8, and SEQ ID NO:9, wherein the presence of such antibodies is taken as indicative of autoimmune infertility.

Accordingly, the present invention also provides an antigenic polypeptide, useful as an immunocontraceptive agent or for the diagnosis of autoimmune infertility, as described above. Preferably, the peptide comprises an antigenic fragment of less than about 30 amino acids in length of a polypeptide comprising an amino acid sequence encoded by a nucleic acid comprising a sequence selected from the group consisting of SEQ ID NO:5, SEQ ID NO:6, SEQ ID NO:7, SEQ ID NO:8, and SEQ ID NO:9.

A sperm receptor polypeptide according to the invention also can be employed to modulate the behavior of sperm, namely, by the application of agents that interact with the sperm, preferably via interaction with a sperm receptor according to the invention. Such a method can have particular application, not only as a means of fertility control (e.g., when practiced in the form of use of a spermicide), but, alternately, as a means of enhancing fertility or contributing to fertility.

As described herein, a spermicide includes not only agents that result in sperm degradation, but also agents that prevent sperm from migrating towards or fertilizing an egg. Such agents can be formulated into a composition comprising further carriers, such as are known in the art, as well as further diluents.

Accordingly, the means of affecting fertility, or contribution to fertility, can comprise either stimulating or inhibiting the binding of a particular ligand to a polypeptide comprising a sperm receptor as defined herein, particularly a polypeptide encoded by a nucleic acid comprising a sequence selected from the group consisting of SEQ ID NO:5, SEQ ID NO:6, SEQ ID NO:7, SEQ ID NO:8, and SEQ ID NO:9. Such stimulation or inhibition can comprise simply adding more of less of the sperm receptor ligand, itself. Other means of affecting fertility, or contribution to fertility, involving modulation of the sperm receptors are also contemplated according to the invention.

Means of Administration

A vaccine or spermicide of the present invention can be made into a pharmaceutical composition by combination with appropriate, pharmaceutically acceptable carriers or diluents, as previously described, and can be formulated to be appropriate for either human or veterinary applications. A vaccine (i.e., an "antisperm composition") or a spermicide can be administered in a variety of ways, including orally, parenterally, intravenously, intra-arterially, subcutaneously, intramuscularly, and the like. Such a composition can be formulated into preparations in solid, semisolid, liquid or gaseous forms, such as tablets, capsules, powders, granules, ointments, solutions, suppositories, injections, inhalants, and aerosols in the usual ways for their respective route of administration. In pharmaceutical dosage forms, the composition can be used alone or in appropriate association, as well as in combination with other pharmaceutically active compounds, including other antisperm compounds or spermicides.

In the case of oral preparations (e.g., wherein the vaccine or spermicide is formulated as an enteric agent), a composition according to the invention can be used alone, or in combination with other antisperm agents and spermicides, together with appropriate additives to make tablets, powders, granules or capsules, e.g., with conventional additives, such as lactose, mannitol, corn starch or potato starch; with binders, such as crystalline cellulose and cellupropriate.

The compositions of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and nonaqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations suitable for vaginal administration can be presented as pessaries, tampons, creams, gels, pastes, foams, or spray formulas containing, in addition to the active ingredient, such carriers as are known in the art to be appropriate.

Unit dosage forms for oral, vaginal or rectal administration, such as syrups, elixirs, and suspensions, can be provided, wherein each dosage unit, e.g., teaspoonful, tablespoonful, tablet or suppository, contains a predetermined amount of the composition containing the antisperm composition, alone or in combination with other antisperm agents. Similarly, unit dosage forms for injection or intravenous administration can comprise a composition as a solution in sterile water, normal saline or other pharmaceutically acceptably carrier.

The term "unit dosage form" as used herein refers to physically discrete units suitable as unitary dosages for human and animal subjects, each unit containing a predetermined quantity of a composition of the present invention, alone or in combination with other antisperm agents or spermicides, calculated in an amount sufficient to produce the desired effect in association with a pharmaceutically acceptable, diluent, carrier or vehicle. The specifications for the novel unit dosage forms of the present invention depend on the particular effect to be achieved, and the particular pharmacodynamics associated with the compound in the individual host.

Accordingly, the present invention also provides a method of fertility regulation (i.e., inhibition or stimulation), which comprises administering such a composition according to the invention. An "effective amount" of a composition of the present invention is administered, wherein the "effective amount" is defined, for example, as that amount required to be administered to an individual subject to achieve an effective blood and/or tissue level of the compound of the present invention sufficient to modulate the behavior of sperm (e.g., to agglutinate sperm cells, or to inhibit or stimulate the chemotaxis, chemokinesis or egg interaction of the sperm). The effective blood level can be chosen, for example, as that level which is sufficient to agglutinate the sperm, or to inhibit or stimulate the chemotaxis, chemikinesis or egg interaction of the sperm in an in vitro screening assay, such as those described in the Examples. The actual dose and schedule for drug administration for each subject can vary depending upon interindividual differences in pharma-cokinetics, drug disposition and metabolism. Moreover, the dose can vary when the compound is used in combination with other drugs. One skilled in the art can easily make any necessary adjustments in the dose to meet the particular needs of the individual, and in view of the individual subject's overall physical health. In particular, the dosages, number of times of administration, and manner of administration can be determined empirically as set out in the following Examples.

EXAMPLES

The following examples further illustrate the present invention but, of course, should not be construed as in any way limiting its scope.

Example 1

This example describes the means employed to identify classes of expressed genes encoding sperm and/or testis-specific receptors.

The rat was chosen for these studies inasmuch as probes are available for this species, and other signal transduction components have been cloned, which will facilitate further studies, e.g., studies of receptor function. Moreover, the vast majority of extant reproductive endocrinological data has been established in the rat (see, e.g., Altman et al., In: *Inbred and Genetically Defined Strains of Laboratory Animals. Part 1: Mouse and Rats*, (Bethesda: FASEB, 1992) 340–348).

The reverse-transcription polymerase chain reaction (RT-PCR) was employed in these experiments. Since mature sperm do not express mRNA, sperm receptors were identified in rat cells that are the immediate precursors of mature, differentiated spermatids. Accordingly, round spermatids were purified from rat testes by elutriation, and RNA was isolated from the spermatids for RT-PCR.

For these experiments, two pairs of degenerate primers were employed that were designed to hybridize to conserved regions of all members of the originally cloned putative odorant receptor family. This increased the likelihood of identifying receptor nucleic acid sequences that actually are expressed in sperm. The sequences for these primers are as follows:

| | |
|---|---|
| ATGGCCTATGCC(G/A)CTA(T/C)GTGGC ("OdR1" sequence); | [SEQ ID NO: 1] |
| T(C/T/A)AG(G/A)TAGATGAA(G/A/C)GG(G/A)TTCAGC ("OdR2" sequence); | [SEQ ID NO: 2] |
| CT(C/G/A)CACAC(A/C)CCCATGTA(C/T)TT(G/T/C)TT(C/T) ("OdR3" sequence); | [SEQ ID NO: 3] |
| and | |
| AG(G/A)TG(G/A)GAA(G/C)CG(A/G)CAGGT(G/T/A) ("OdR4" sequence). | [SEQ ID NO: 4] |

Since the known odorant receptor genes lack introns, controls were performed for each PCR reaction using RNA that was mock reverse-transcribed in the absence of reverse transcriptase. No signal was detected in the control under these conditions. RT-PCR in round spermatids using OdR1 and OdR2 or OdR3 and OdR4 yielded PCR products of 506 base pairs in length. The 506 base-pair PCR fragments were gel-purified, usually yielding approximately 2 βg of DNA per fragment.

The PCR products were subcloned into a pCR", vector using an InVitrogen TA Cloning® Kit (InVitrogen, San Diego, Calif.), and were used to transform One-Shot™ cells (InVitrogen). The resultant transformed cells were screened on LB (Luria-Bertani medium) plates containing ampicillin and Xgal (5-bromo-4-chloro- 3-indolyl-:-D-galactoside). Eight white colonies were initially isolated. Plasmid DNA was purified from these colonies using a Promega Minipreps DNA purification system (Promega, Madison, Wis.).

Sequencing of the clones revealed that the PCR products grouped into two classes, namely class "D" and class "G," which are unrelated at the DNA and protein levels, except for the presence of some conserved motifs. Eight PCR products were initially picked for further characterization. Interestingly, of these colonies, 100% of the PCR insert sequenced demonstrate unique sequences. Namely, these testis and spermatid-specific products shared only about 40% to 50% homology with known members of the odorant receptor gene family, and actually were more related to each other than to any other known sequenced receptor. This confirms that the nucleic acid sequences are novel sperm receptors, and, further, appear to comprise a novel multigene family, which may be specific to spermatids.

Similar studies can be employed to obtain sperm receptor clones from humans, particularly once the sperm-specific production of these proteins has been confirmed. Furthermore, subsequent screens can be performed in either rat or humans, using the methods identified herein, to identify additional clones comprising further novel sperm receptors.

As a result of these experiments, the full-length clones of these putative novel sperm chemoreceptors were obtained.

Example 2

This example describes the development of class D and class G receptor probes based on specific sequences determined by PCR, and the identification of full-length clones encompassing class D and G receptors from a rat genomic library.

In the second step, specific primers were designed to either D or G receptor classes in a "nested" fashion. The scheme employed for the D class receptor probes is shown in FIG. 1. The primer pairs 4.1 and 4.2 were designed to generate a probe that recognizes the 5' half of the class D sperm receptor transcript (i.e., probe 3), whereas the primer pairs 4.3 and 4.4 were used to generate a probe that recognizes the 3' half of the class D receptor transcript (i.e., probe 4).

A similar scheme (i.e., using different primers) was employed for the development of the G class receptor probes. Namely, primers designated 1.1 and 1.2 and a second set designated 1.3 and 1.4 were designed specifically to the G class of receptors. Primers 1.1 and 1.2 yield a PCR product encompassing the 5' half of G class PCR products (i.e., probe 1), whereas primers 1.3 and 1.4 generate a PCR product that recognizes the 3' half (i.e., probe 2). Moreover, the development of probes according to this example similarly can be employed to generate further probes based on isolated G and D class receptors.

The double-stranded PCR products generated by primer pairs 4.1 and 4.2, primer pairs 4.3 and 4.4, primer pairs 1.1 and 1.2, and primer pairs 1.3 and 1.4, all were approximately 250 base pairs in length. This design of primers to generate PCR products, which serve as probes for library screening, was advantageous in that it enabled "double" screening of a rat genomic library to be carried out. Specifically, two sets of lifts could be made. One lift was screened with the 5' probe, i.e., probe 3 (or probe 1), and the other lift was screened with a 3' probe, i.e., probe 4 (or probe 2). Only those colonies that hybridized with both probes were used, so as to minimize the likelihood that weakly related "false positive" clones were obtained and sequenced.

Accordingly, probes 1, 2, 3 and 4 were labeled using a Boehringer Mannheim nick translation kit according to the manufacturer's recommendations, and using both $^{32}$P-dATP and $^{32}$P-dCTP as radionucleotides. The labeled probes were employed to screen a genomic Sprague-Dawley rat library (Clontech, Palo Alto, Calif.) in EMBL3 bacteriophage. The EMBL bacteriophage were infected into bacteriophage 8-sensitive K802 cells (Clontech), and were hybridized in situ using standard library screening protocols according to the manufacturer, which employ 40% formamide at 42° C. Double nitrocellulose (Schleicher & Schuell BA-S 85) lifts were taken, and only colonies that were doubly positive (i.e., using both probes 1 and 2, or probes 3 and 4) were taken for large-scale isolation and subsequent sequencing off of phage DNA. To ensure that single colonies were picked, secondary and tertiary lifts were performed prior to sequencing.

About eleven full-length receptor clones were obtained in this fashion, of which five receptors (i.e., four class D receptors and one class G receptor) have been fully sequenced. Additional full-length clones can be obtained through further screening (e.g., through screening of libraries other than a rat library), and using further probes based on the identified sperm receptor nucleic acid sequences. For instance, highly conserved regions of sperm receptors can be used to generate PCR probes, and the library can be rescreened using the new probes to identify yet other members of the sperm receptor family.

Example 3

This example describes the sequencing of the five full-length clones obtained from a rat genomic library.

Non-radioactive sequencing reactions were performed (Core Labs, Johns Hopkins Hospital) off of EMBL3 phage, which yielded about 300 to 400 base pairs per reaction. Sequencing was performed in both directions so as to ensure the correctness of the sequence. The sequences of the inserts present in four D receptor clones are depicted in FIG. 2 (i.e., the sequence in the "D-2" clone, which also is set out in SEQ ID NO:5), FIG. 3 (i.e., the sequence in the "D-7" clone, which also is set out in SEQ ID NO:6), FIG. 4 (i.e., the sequence in the "D-8" clone, which also is set out in SEQ ID NO:7) and FIG. 5 (i.e., the sequence in the "D-9" clone, which also is set out in SEQ ID NO:8) and FIG. 6 (i.e., the sequence in the "G-X" clone, which also is set out in SEQ ID NO:9).

For both D and G class sequenced clones, the amino acid sequences were deduced using the MacVector program (Apple Products), and the obtained sequences were aligned. The deduced amino acid sequences for phage clones D-2, D-7, D-8, D-9, and G-X are presented in FIG. 7 through FIG. 11, respectively. The sequences of the four D class phage clones, which represent novel members of the sperm receptor D family are aligned in FIG. 12. Significant homology between the members of the D family exist and are highlighted by inclusion of homologous sequences in "boxed" regions. The putative start sites align well with the start site of the odorant receptor families, although the overall conservation of the sequence between sperm and odorant receptors is only 40 to 50% at the amino acid level. This confirms that these isolated sperm receptors, indeed, represent a new family of putative chemosensory receptors.

Example 4

This example describes the genomic cloning of spermatid chemoreceptors D and G.

For the D class of receptors, two probes representing each half of the PCR product were employed and designated D.1–D.2 and D.3–D.4. Double lifts of an EMBL3 rat genomic library were screened with D.1–D.2 and D.3–D.4 probes at high stringency and 10 of 52 cohybridizing plaques were isolated. This strategy was employed to significantly decrease the probability of identifying the potentially thousands of related seven transmembrane odorant receptors.

Double-strand sequencing of purified phage DNA resulted in the identification of four DNA species containing the pSCR D sequence. A methionine flanked by a secondary Kozak sequence (Kozak (1987)) begins an open reading frame of 963 base pairs in each species. The DNA sequence encodes 321 amino acids [SEQ ID NO:10] that contain seven transmembrane domains (FIG. 15) as predicted by Kyte-Doolittle hydrophilicity plots and align with published full-length odorant receptors cDNAs. Intervening hydrophilic sequences represent intracellular and extracellular loops. Amino acid alignment demonstrates that the four D receptors (designated D-2, D-7, D-8, and D-9) are greater than 85% identical to each other at the amino acid level (FIG. 16). The existence of a family of D-type spermatid chemoreceptors is apparent based upon the distinct amino acid differences among the receptors and their disparate 3' untranslated regions.

Using the same strategy followed for cloning SCR D, two probes representing each half of PCR product G were employed and designated G.1–G.2 and G.3–G.4. Double lifts of an EMBL3 rat genomic library were screened with these probes at high stringency and 10 of 221 cohybridizing plaques were isolated. Double-strand sequencing of purified phage DNA resulted in the identification of three DNA species containing the pSCR G sequence. A methionine flanked by a secondary Kozak sequence begins an open reading frame of 981 base pairs in each species. The DNA sequence encodes 327 amino acids [SEQ ID NO:14] that contain seven transmembrane domains (FIG. 17) as predicted by Kyte-Doolittle hydrophilicity plots and align with published full-length odorant receptors cDNAs. Intervening hydrophilic sequences represent intracellular and extracellular loops. Amino acid alignment demonstrates that the three G receptors (designated G.14, G.15, and G.16) are greater than 92% identical to each other at the amino acid level and represent another family of spermatid chemoreceptors (FIG. 18).

Example 5

This example describes the means of analyzing the 5' flanking sequence of the sperm receptor coding sequence.

A major concern when cloning from genomic libraries is to ensure that the correct start methionine is identified. It is important to identify the correct start site, as the N-terminal sequence may be important for ligand binding and correct targeting of nascent proteins to the plasma membrane. Moreover, it is possible the additional coding sequences can lie immediately upstream of the sperm receptor coding sequence. To confirm this, 5' rapid amplification of cDNA ends (i.e., RACE) can be performed to amplify nucleic acid sequences from a messenger RNA template between a defined internal site and a sequence at the 5' end of the mRNA (Life Technologies, Gaithersburg, Md.). For these experiments, spermatid mRNA can be isolated and subjected to 5' RACE analysis. This will demonstrate that these receptors are actually expressed in spermatid mRNA and will allow for the identification of the appropriate start site.

The 5' flanking sequence of the sperm receptor coding sequence additionally can be examined to confirm that the open reading frame is actually translated into protein. The likely start methionine residues can be identified by an examination of the sequence. Within a limited number of base pairs upstream from that methionine start site, there should occur a TATA box and a Kozak consensus sequence. Further confirmation can be obtained by generating antibodies to fusion proteins bacterially expressed from plasmids containing the 5' regions. These antibodies can then be used for immunoblot analysis and immunohistochemistry to confirm that the receptors are expressed in the proper location and are associated with antibodies directed against the rest of the receptor molecules. In addition, full-length sperm receptor sequences can be used in a rabbit reticulocyte lysate in vitro translation system (such as is commercially available, for instance) to confirm translation into protein. The experiments similarly can confirm or negate the existence of additional 5' coding regions.

Example 6

This example describes the identification of 5' splice variants of SCR D and SCR G.

A striking feature common to all D receptors identified is the presence of the splice acceptor site, TGTC-CTTTCTTTCAGG [SEQ ID NO:31], in the genomic DNA immediately upstream of the presumptive starting methionine. This suggested the possibility of either alternative amino terminal splicing of spermatid chemoreceptors or the existence of processing of the 5' untranslated regions for the purpose of regulating receptor expression.

5' RACE PCR was employed using testis poly A+ RNA in order to identify amino terminal splice variants of D receptors. Two 5' RACE products were obtained, subcloned into the pCRII vector, and DNA sequenced. Whereas one 5' RACE product (R350) was identical to the D-8 genomic sequence, the other product (R500) contained a novel 5' sequence immediately upstream of SCR sequence corresponding to the D-8 receptor (FIG. 19A). The cDNA encodes an upstream open reading frame of 25 amino acids with a potentially new starting methionine at position −20. The novel sequence is in frame with a downstream SCR sequence that corresponds to SCR D-7 and SCR D-8. Corresponding RACE PCR work with the SCR G family of receptors has also revealed 5' splicing.

The alignment of the predicted amino acid sequences of the two SCR D cDNA species R500 and R350 with the amino acid sequence of SCR D-8 is shown in FIG. 19B.

Example 7

This example demonstrate that the D- and G-type SCRs are unique subfamilies of the odorant receptor superfamily.

Figure 20:
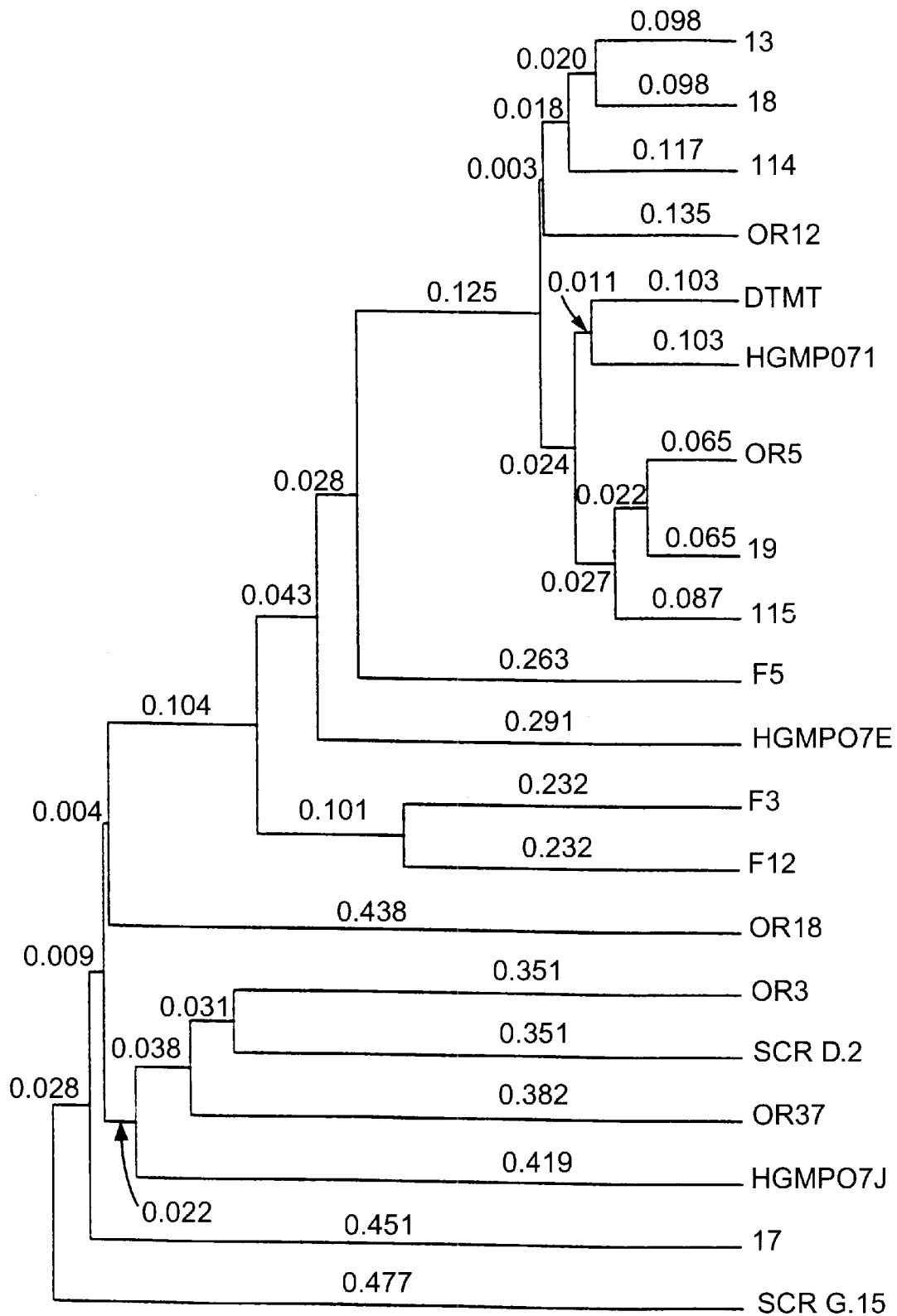
FIG. 20 is a phylogenetic tree (GeneWorks), which demonstrates the relatedness of SCR D-2 and G-15 to other full-length members of the odorant receptor superfamily.

Alignment of SCRs with known full length odorant receptors (Buck and Axel, Cell, 65, 175–187 (1991); Nef et al., PNAS(USA), 89, 8948–8952 (1992); Parmentier et al. (1992), supra; and Raming et al., Nature, 361, 353–356 (1993)) demonstrates that they share characteristic olfactory receptor sequence identities in transmembrane domains (TMDs) 1, 2, 3, 6 and 7, and in the intracellular loop between TMD 3 and TMD 4. However, the total amino acid identities between SCRs and other odorant receptors is at best 35–40%. This is a relatively low percentage identity compared to the relatedness of other odorant receptors to each other, which ranges from 35% to over 90%. A phylogenetic tree, which was constructed using the GeneWorks program, demonstrates that the SCR G family is the most evolutionarily divergent among all known full-length receptors (FIG. 20). The SCR D family is additionally quite divergent, but does share some commonalities with the OR3 (Nef et al. (1992), supra) and OR37 receptors (Raming et al. (1993), supra). The rat D SCRs are more closely related to certain rodent olfactory receptors than to chemoreceptors cloned from dog testis.

Example 8

This example describes the means of assessing the expression of the sperm receptor coding sequence, in various host tissues, and at various developmental stages.

Precise developmental and spatial localization of members of the sperm receptor family will serve several purposes. Different classes or subfamilies of receptors can demonstrate differential localization. Thus, some receptors may serve as chemoreceptors for development from spermatogonia to spermatid in the seminiferous tubules. Others may be expressed in sperm as they traverse the epididymis. Still other chemoreceptors may be present but not exposed on the surface until capacitation or hyperactivation.

A number of organ systems can be screened to demonstrate the specificity of the sperm receptors. It may be that some receptors are, indeed, expressed in multiple tissues as they may serve a common function. In contrast, others may be uniquely localized or on maturing spermatozoa. However, to be a viable target of a contraceptive vaccine, a receptor preferably is expressed ubiquitously in sperm, and not on only a small subset of sperm.

Determination of the site of receptor synthesis by investigating mRNA localization can be done by several different approaches, which are well known to those of skill in the art. Taken together, these methods should establish with sensitivity site(s) of synthesis of individual members of the various classes of the sperm chemoreceptors. For instance, trans-tissue RT-PCR has the advantage of being rapid and sensitive. By merely designing primers specific for individual or groups of receptors, many tissues can be screened rapidly for expression. In addition, PCR fragments can be cloned and sequenced so as to determine if the PCR product obtained reflects the anticipated receptor species. This can reveal new, related receptors, which share homology in the region of primer design but have divergent internal sequences. This can be done by assessing the base pair size of the PCR product. Based on the known sequence, the predicted size can be quite accurately determined. Deviation from this size can be taken to represent new sequences, which might reflect new members of a class of receptors.

To confirm RT-PCR, trans-tissue Northern blot analysis can be performed using probes designed against receptor classes or against individual receptors. Northern blot analysis is quantitative, essentially unaffected by genomic contamination, and can provide information as to message size. Should certain transcripts be of extremely low abundance, it may, however, be difficult to determine the tissue specificity by Northern blot analysis. In these cases, trans-tissue RNase protection assays can be employed. RNase protection assays combine sensitivity and quantitation. In this method, probes designed to specific sequences are incubated with RNA. Should the probe hybridize with the species in RNA extracted from that tissue, a region of RNA will be protected that corresponds to some part of that probe. Thus, gel electrophoresis will reveal a band that is "protected."

With at least some classes of receptors, it is possible that alternative splicing occurs. This can be assessed via pilot studies, and, if detected, will necessitate the generation of antibodies to splice variants so as to determine the sperm receptors'temporal or spatial patterns of expression.

Northern blot analysis using probes directed against the five full-length receptor clones confirms that these sperm receptors are uniquely expressed in testis. Based on these results, the cellular site of synthesis of these proteins was determined.

Example 9

This example demonstrates the expression of the sperm receptor coding sequence in mature sperm.

In order to prove that SCRs are expressed in spermatids of the testis, RNAse protection assays were conducted using riboprobes corresponding to D.1–D.4 (pSCR D), D.5–D.6 (amino terminus SCR D), and G.1–G.4 (pSCR G). Using 10 μof total RNA from pachytene spermatocytes, round spermatids and olfactory epithelium, full-length protection of all three riboprobes was observed in round spermatids and olfactory epithelium, but not in pachytene spermatocytes (after 24 hr hybridization at 45° C., RNAse-treated samples were run on nondenaturing 6% polyacrylamide TBE gels). Whereas pachytene spermatocytes are involved in the meiotic program, round spermatids specialize in differentiating into testicular spermatozoa. Given that the olfactory epithelium is believed to express thousands of olfactory receptors, it is not surprising that members of the SCR family are likewise expressed in this tissue. With the G.1–G.4 probe, multiple protected fragments are observed using olfactory RNA, suggesting that select motifs of the SCR G receptor may be present in other odorant receptor transcripts. The expression of SCRs in tissues other than testis and olfactory epithelium was evaluated by using polyA+ RNA (0.5 βg) from testis, lung, brain, liver and spleen. The integrity of template RNA was confirmed using a 125 bp β-actin riboprobe. Ten pg of yeast RNA served as a negative control. Full-length protection of the three riboprobes was observed in testis and faint bands were additionally detected in spleen.

Example 10

This example describes the means of determining the cellular site of synthesis of the sperm receptor proteins according to the invention.

Once the site(s) of tissue expression for individual members and classes of putative sperm chemoreceptors have been determined, it is necessary to determine the cellular site of synthesis. Pilot studies demonstrate that mature spermatozoa contain at least one class of receptors, located to the mid-piece (Walensky et al. (1995), supra). However, other receptors can be expressed or active at the times of spermatogenesis and spermiation, and can be present in other cells of the testis (and even other chemosensing cells in the body). To determine this, in situ hybridization can be done using two techniques, $^{35}$S-labeling and digoxigenin labeling of cRNA probes. For in situ hybridization using $^{35}$S-nucleotide cRNA probes, modification of the Stratagene (Stratagene, La Jolla, Calif.) in vitro transcription protocol can be employed as previously described (see, e.g., Ressler et al., Cell, 791, 1245–255 (1994); and Ressler et al., Cell, 73, 596–609 (1993)). Similarly, digoxigenin labeling of cRNA probes can be carried out as specified by the manufacturer (e.g., Boehringer Mannheim, Indianapolis, Ind.) with several modifications (see, e.g., Wiermer-Schaeren et al., Histochem., 100, 431–440 (1993); and Bradley et al., Proc. Natl. Acad. Sci., 91, 8890–8894 (1994)).

In situ hybridization studies on sexually mature testis demonstrate specific localization of the full-length sperm receptors described herein to mature sperm. These findings, coupled with the results described in Example 8, confirm that these new sperm receptors are unique to the cell surface of mature sperm. Moreover, these findings indicate that the sperm receptors are correctly positioned to be involved in sperm signal transduction and, thus, prime targets for both infertility therapy and contraceptive design.

Example 11

This example describes the localization of expression of SCR D in the testis in situ.

To confirm the localization of SCR D expression in the testis, in situ hybridization studies were conducted using the $^{32}$P-labeled antisense riboprobe D.5–D.6, which corresponds to the amino terminus of SCR D. The riboprobe labels adluminal cells of the seminiferous tubule, which correspond to elongating spermatids of the testis. Furthermore, this riboprobe labels only a fraction of those seminiferous tubule cross sections that contain elongating spermatids. This suggests that different populations of spermatids express distinct receptors. The remaining seminiferous epithelial and interstitial cells are negative. No labeling is detected in testis sections incubated with the sense riboprobe. The in situ results are consistent with the localization of chemoreceptor proteins to spermatids by immunohistochemistry, and with RNAse protection of SCR riboprobes using round spermatid but not pachytene spermatocyte RNA.

Example 12

This example describes the design of antibodies to sperm receptor proteins according to the invention.

Once the general tissue distribution and cellular distribution of the sites of synthesis of the individual and classes of sperm receptors has been determined, it will be possible to design and detect antibodies thereto. Immunodetection will serve several purposes. First, it will confirm results of mRNA localization studies. Second, inasmuch as detection by antibodies is based on interactions at the protein-protein level, whereas mRNA detection is based upon hybridization of complementary nucleotide sequences, these two methodologies provide excellent controls for each other. Third, immunolocalization by immunoblot analysis can provide rapid quantitative information on the site of tissue production.

This is of further importance since a receptor must be expressed relatively abundantly to be a viable target for vaccine design. Fourth, immunohistochemistry and immunocytochemistry can confirm the subcellular localization of these receptors, which is of critical importance in assessing the function of the receptors. Fifth, the antibodies can be used to determine which receptor domains are expressed externally and internally. This is important in further designing antibodies to be employed for functional studies. Moreover, it is important to identify which regions are externally expressed in terms of contraceptive vaccine design.

Two types of polyclonal antibodies can be generated. The first type of antibody can be directed against fusion proteins representing regions of sequence derived from bacterially-expressed receptors. Antibodies generated in this manner can be directed against specific, predirected portions of the receptor. This yields robust antibody synthesis, as the antigen is often 10 to 30 kDa in length, allowing for multiple epitope recognition. Given the large size of the antigen, it is unlikely the epitopes that these antibodies recognize are all hidden internally. Such antibodies can be extremely useful in recognizing individual receptors and classes of receptors. On the other hand, if receptors are closely related, except for restricted sequence differences, it may be hard to design antibodies that are specific for one particular receptor. In this case, antibodies generated against synthetic peptides representing restricted 15 to 18 amino acid stretches of a receptor can be the preparation of choice. Such antibodies can also be designed against various specific short stretches of highly conserved sequences and, therefore, recognize a particular class of sperm receptor. The potential drawback associated with use of anti-peptide antibodies is that the region of the protein comprising the antigen may actually be buried within the tertiary structure of the antibody. In this case, it is often necessary to use an ionic detergent, such as sodium dodecyl sulfate, to partially denature the protein (Jones et al., *Science*, 244, 790–795 (1989)). Thus, initially, anti-fusion protein antibodies can be employed. Later, specific anti-peptide antibodies can be designed.

One fusion protein system, which can be employed and which already has been used to generate an antibody to an N-terminal 10 kDa fragment of the insert present in receptor clone D-9, is the pET-20b positive expression system by Novagen (Madison, Wis.). The nucleic acid sequence [SEQ ID NO:15] used to generate this antibody is depicted in FIG. 13. The amino acid sequence [SEQ ID NO:16] against which the antibody was generated is depicted in FIG. 14.

The pET-20b vector allows fusion to an N-terminal signal sequence for potential periplasmic localization. The vector has proven useful in expression of membrane receptors that contain hydrophobic regions, which may make bacterial expression difficult. Typically, for fusion proteins containing hydrophobic regions of a membrane-spanning main receptor, there may be difficulty in achieving bacterial expression, unless this vector is used. The pET-20b vector allows for ampicillin selection, contains a strong T7 promoter for controlling gene expression, and possesses numerous restriction sites. In addition, the vector incorporates an optional C-terminal His.Tag™ oligohistidine domain for purification using affinity chromatography.

Fusion protein production can be done according to the manufacturer's instructions. Briefly, the vector is prepared by restriction digestion of both sites. The cDNA coding for the desired region of the receptor is prepared for insertion by restriction digestion followed by gel purification. Thereafter, the insert is ligated to vector and introduced into HMS174 competent cells (Novagen). An aliquot from a 50 βl sample of each transformation is spread onto LB agar plates containing ampicillin. After overnight incubation at 37° C., plasmids are screened by PCR for incorporation of vector sequences. After positive clones are identified, the plasmids can be isolated for transformation into expression hosts. After plasmid isolation, approximately 1 ng of plasmid is diluted in sterile water and transformation is again performed. The expression of the target DNA is induced by the addition of IPTG (isopropylthiogalactoside, typically at a concentration of about 0.4 mM) to a culture in log phase growth.

To determine the optimal time course for target protein production following gene induction, aliquots of the culture are taken at 60 min intervals following IPTG addition. The cells are collected and homogenized to yield cell pellets and cell supernatants after centrifugation. The yields are assessed in comparison to those of uninduced cells using SDS-PAGE. It is unlikely, but should the fusion protein remain associated with the pellet, it is possible to solubilize fusion protein using an increasing molarity of urea. Furthermore, other techniques and approaches for obtaining a soluble fusion protein are known in the art and can be employed should this be a technical impediment.

In this manner, milligram amounts of fusion protein can be obtained for injection into rabbits as has been previously described (e.g., Walensky et al. (1995), supra).

Generally, about 0.7 ml of antigen containing about 150 to 200 βg of protein and present in complete Freund's adjuvant (Hazelton Research, Vienna, Va.) can be injected subdermally. Animals can be boosted after about 3 weeks following injection by injection of a similar amount of antigen intravenously. Subsequent boosts in incomplete Freund's adjuvant can be injected subdermally about every 4 weeks. Test bleeds can typically be done about 7 to 10 days after each boost.

Anti-peptide antibodies also can be obtained. In general, peptides will be designed to serve two purposes. First, sequences will be selected that are extremely specific for an individual receptor. This is the case for the D clones, which thus far appear to be localized specifically to mature sperm. However, should the results of RNA expression and localization studies indicate that certain classes of receptor are expressed specifically in sperm, antibodies can be designed to recognize that particular class of receptors. To generate anti-peptide antibodies, generally 15 to 18 amino acid stretches of sequence are identified for in vitro peptide synthesis (Core Labs, Johns Hopkins Hospital). On the C-terminal side, a terminal lysine is added so as to permit coupling to a carrier protein, such as bovine serum albumin (BSA; see, e.g., Roskams et al., *A. Chem. Society*, 16, 308 (1994)). Hydrophilic peptides are the easiest to work with, although it is possible to immunize using even extremely hydrophobic sequences. Peptides are then chemically cross-linked to the carrier BSA for immunization into rabbits according to the aforementioned protocols. For hydrophobic peptides, cross-linking optimally is done in a Tris buffer at pH 7.0. Moreover, hydrophobic peptides can be dissolved in a mixture of isopropanol and Tris buffers.

Antibodies to fusion protein can be affinity-purified using commercially available affinity columns (e.g., Pharmacia, Piscataway, N.J.) in which sepharose is coupled to His, which is recognized by the His.Tag™ system. Eluates can be purified further by absorbing anti-BSA antibodies with two passes with a BSA-sepharose column (Pharmacia). The subsequent eluates from either column are spectrophotometrically assayed for IgG concentration, which is confirmed by SDS-PAGE using standard BSA solutions as a control. Subsequently, antibody specificity can be confirmed by immunoblot or immunodot analysis, such as is known in the art.

The antibodies obtained according to this Example can be employed in localization of the sperm receptors by immunohistochemistry and immunocytochemistry (see, e.g., Walensky et al. (1995), supra; and Roskams et al. (1994), supra). Moreover, subcellular immunolocalization in spermatozoa also can be performed, e.g., as previously described (Walensky et al. (1995), supra; and Cunningham et al., *Soc. Neurosci. Abst.*, 17, 180 (1991)). Furthermore, the antibodies can be employed to study the sperm receptors and modulate the behavior of the sperm, as described in the following Example.

Example 13

This example describes the use of antibodies described in Example 12 to study the sperm receptors and modulate the behavior of sperm.

Previous studies confirm that at least some of the D class receptors are located on the surface membrane of the tail mid-piece and are accessible to antibody recognition under non-permeabilizing conditions. For one receptor tested thusfar, a protein of the same molecular weight was found in human sperm (Walensky et al. (1995), supra). These results demonstrate that these receptors are involved in signal transduction pathways modulating sperm respiration or motility.

Accordingly, the ability of affinity-purified antibodies to the sperm receptors to agglutinate sperm can be determined. Receptor occupancy by antibody can potentially "block" or "enhance" motility. This can be assessed by directing microscopic examination of the effect of antibody on the motility of isolated sperm, and quantitating any effect using a Hamilton Thorn 2000 analyzer as previously described (e.g., Klinefelter et al., *J. Androl.*, 15(4), 318–327 (1994)). It may be necessary to add follicular fluid in these experiments to have sperm dispositioned properly, and for an effect of antibody on motility behavior to be observed. This would especially be true with sperm receptors that alter chemotaxis or chemokinesis. Accordingly, sperm to be agglutinated can be incubated in the presence of follicular fluid or follicular fluid extracts, and then can be tested to assess the effect of antibody on the sperm.

Ultimately, artificial insemination can be performed in the presence of antibodies. In other words, although receptor occupancy can block motility in the epididymis, it can be restored in utero. Thus, artificial insemination experiments can be performed, for example, as described in Klinefelter et al. (1994), supra; and Klinefelter et al., *J. Androl.*, 13(5), 409–421 (1992)).

Similarly, recent provocative studies suggest that mammalian spermatozoa demonstrate chemotaxis (Ralt et al., *Biol. Reprod.*, 50, 774–785 (1994); Gnessi et al., *J. Clin. Endocrinol. Metab.*, 637(4), 841–846 (1986); Ralt et al., *Proc. Natl. Acad. Sci.*, 88(7), 2840–2844 (1991); Cohen-Dayag et al., *Biol. Reprod.*, 50(4), 786–790 (1994); and Makler et al., *Fert. Ster.*, 57(5), 1066–1074 (1992)). Therefore, the effect of receptor antibodies on the ability of follicular fluids to affect motility can be assessed as described, for instance, by Ralt et al. (1991), supra.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. An enriched or isolated nucleic acid comprising a sequence selected from the group consisting of SEQ ID NO:5, SEQ ID NO:6, SEQ ID NO:7, SEQ ID NO:8, and SEQ ID NO:9.

2. A vector which comprises a nucleic acid comprising a sequence selected from the group consisting of SEQ ID NO:5, SEQ ID NO:6, SEQ ID NO:7, SEQ ID NO:8, and SEQ ID NO:9.

3. A host cell which comprises a vector of claim 2.

4. A method of producing a sperm receptor, which method comprises maintaining a host cell of claim 3 under conditions whereby said host cell produces a sperm receptor.

5. The method of claim 4, which further comprises purifying the sperm receptor from the host cell.

6. An enriched or isolated polypeptide comprising an amino acid sequence encoded by a nucleic acid comprising a sequence selected from the group consisting of SEQ ID NO:5, SEQ ID NO:6, SEQ ID NO:7, SEQ ID NO:8, and SEQ ID NO:9.

7. The enriched or isolated polypeptide of claim 6, wherein said polypeptide comprises a sequence selected from the group consisting of SEQ ID NO:10, SEQ ID NO:11, SEQ ID NO:12, SEQ ID NO:13, and SEQ ID NO:14.

8. An antigenic polypeptide comprising an antigenic fragment of about 50 amino acids in length of an enriched or isolated polypeptide of claim 6.

9. An enriched or isolated nucleic acid encoding a sperm receptor that hybridizes under highly stringent conditions to a portion of SEQ ID NO: 5, SEQ ID NO: 6, SEQ ID NO: 7 or SEQ ID NO: 8 consisting essentially of a nucleotide sequence encoding amino acids 3–13, 18–34, 36–48, 56–96, 112–128, 132–144, 163–200, 202–207, 234–260, 269–275, 280–285 or 287–301, or an enriched or isolated nucleic acid that is complementary to said enriched or isolated nucleic acid encoding a sperm receptor.

10. The nucleic acid of claim 9, wherein said sperm receptor is that which is located on the surface membrane of the tail midpiece of mature sperm.

11. A vector comprising a nucleic acid of claim 9.

12. A host cell comprising a vector of claim 11.

13. A method of producing a sperm receptor, which comprises maintaining a host cell of claim 10 under conditions whereby said host cell produces a sperm receptor.

14. The method of claim 13, which further comprises purifying the sperm receptor from the host cell.

15. An enriched or isolated polypeptide comprising an amino acid sequence encoded by a nucleic acid encoding a sperm receptor of claim 9.

16. An antigenic polypeptide comprising an antigenic fragment of about 50 amino acids in length of an enriched or isolated polypeptide of claim 15.

17. A method for screening for autoimmune infertility in a subject, which comprises detecting the presence of antibodies in said subject that bind to a polypeptide of claim 15, wherein the presence of said antibodies is indicative of autoimmune infertility.

18. A method of screening a cDNA library or a genomic DNA library for a nucleic acid encoding a sperm receptor, which method comprises hybridizing under highly stringent conditions a cDNA library or a genomic DNA library with a probe nucleic acid of SEQ ID NO:1, SEQ ID NO: 2, SEQ ID NO: 3, or SEQ ID NO: 4, or a portion of SEQ ID NO: 5, SEQ ID NO: 6, SEQ ID NO: 7 or SEQ ID NO: 8 consisting essentially of a nucleotide sequence encoding amino acids 3–13, 18–34, 36–48, 56–96, 112–128, 132–144, 163–200, 202–207, 234–260, 269–275, 280–285, or 287–301, whereupon a nucleic acid which hybridizes to said probe under highly stringent conditions encodes a sperm receptor.

19. The method of claim 18, which further comprises isolating a host or vector comprising said nucleic acid.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (other nucleic acid)

(xi) SEQUENCE DESCRIPTION: SEQ ID NO:1:

ATGGCCTATG CCRCTAYGTG GC                     22

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (other nucleic acid)

(xi) SEQUENCE DESCRIPTION: SEQ ID NO:2:

THAGRTAGAT GAAVGGRTTC AGC     23

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:3:

CTVCACACMC CCATGTAYTT BTTY     24

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:4:

AGRTGRGAAS CGRCAGGTD     19

(2) INFORMATION FOR SEQ ID NO:5:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
ATG ACT GTC AAC TGT TCT CTG TGG CAG GAG AAT AGT TTG ACT GTC AAA        48
Met Thr Val Asn Cys Ser Leu Trp Gln Glu Asn Ser Leu Thr Val Lys
 1               5                  10                  15

CAC TTT GCA TTT GCC AAG TTC TCT GAG GTC CCT GGA GAA TGC TTC CTC        96
His Phe Ala Phe Ala Lys Phe Ser Glu Val Pro Gly Glu Cys Phe Leu
             20                  25                  30

CTG TTC AAC CTC ATC CTT CTC ATG TTC TTA GTA TCA CTA ACA GGA AAT       144
Leu Phe Asn Leu Ile Leu Leu Met Phe Leu Val Ser Leu Thr Gly Asn
         35                  40                  45

ACT CTC ATA GTC CTT GCT ATT TGT ACC AGT CCA TCT CTA CAC ACC CCC       192
Thr Leu Ile Val Leu Ala Ile Cys Thr Ser Pro Ser Leu His Thr Pro
 50                  55                  60

ATG TAC TTC TTT CTG GCC AAC TTG TCT CTC CTG GAG ATT GGC TAT ACT       240
Met Tyr Phe Phe Leu Ala Asn Leu Ser Leu Leu Glu Ile Gly Tyr Thr
 65                  70                  75                  80

TGC TCT GTC ATA CCC AAG ATG CTG CAG AGC CTT GTG AGT GAG GCC AGA       288
Cys Ser Val Ile Pro Lys Met Leu Gln Ser Leu Val Ser Glu Ala Arg
                 85                  90                  95

GAG ATC TCT CGG GAG GGA TGT GCC ACA CAG ATG TTT TTT TTC GCA TTT       336
Glu Ile Ser Arg Glu Gly Cys Ala Thr Gln Met Phe Phe Phe Ala Phe
            100                 105                 110

TTT GGT ATA ACT GAG TGC TGC CTA TTG GCA GCC ATG GCC TTT GAC CGC       384
Phe Gly Ile Thr Glu Cys Cys Leu Leu Ala Ala Met Ala Phe Asp Arg
        115                 120                 125
```

```
TGC ATG GCC ATA TGC TCC CCA CTC CAC TAT GCA ACC CGA ATG AGT CGN       432
Cys Met Ala Ile Cys Ser Pro Leu His Tyr Ala Thr Arg Met Ser Arg
        130                 135                 140

GAG GTA TGT GCC CAT TTG GCA ATT GTT TCA TGG GGA ATG GGA TGC ATA       480
Glu Val Cys Ala His Leu Ala Ile Val Ser Trp Gly Met Gly Cys Ile
145                 150                 155                 160

GTA AGT CTG GGA CAA ACC AAT TTT ATT TTC TCC TTG AAC TTC TGT GGA       528
Val Ser Leu Gly Gln Thr Asn Phe Ile Phe Ser Leu Asn Phe Cys Gly
                165                 170                 175

CCC TGT GAA ATA GAC CAC TTC TTC TGT GAC CTT CCA CCT CTC CTG GCA       576
Pro Cys Glu Ile Asp His Phe Phe Cys Asp Leu Pro Pro Leu Leu Ala
            180                 185                 190

CTT GCC TGT GGA GAT ACA TCC CAA AAC GAG GCT GCC ATC TTT GTG GTA       624
Leu Ala Cys Gly Asp Thr Ser Gln Asn Glu Ala Ala Ile Phe Val Val
        195                 200                 205

GCA GTC CTC TGC ATA TCT AGC CCA TTT TTG CTG ATC ATT TAT TCT TAT       672
Ala Val Leu Cys Ile Ser Ser Pro Phe Leu Leu Ile Ile Tyr Ser Tyr
210                 215                 220

GTC AAA ATT CTC ATT GCA GTG CTN CTG ATG CCT TCA CCT GAG GGG CGC       720
Val Lys Ile Leu Ile Ala Val Leu Leu Met Pro Ser Pro Glu Gly Arg
225                 230                 235                 240

CAT AAA GCT CTT TCC ACC TGT TCG TCT CAC CTA CTT GTA GTC ACA CTT       768
His Lys Ala Leu Ser Thr Cys Ser Ser His Leu Leu Val Val Thr Leu
                245                 250                 255

TTT TAT GGC TCA GCA TGT ATT ACC TAT TTG AGG CCC AAG TCT AGC CAC       816
Phe Tyr Gly Ser Ala Cys Ile Thr Tyr Leu Arg Pro Lys Ser Ser His
            260                 265                 270

TCA CCA GGA ATG GAC AAA TTC TTG GCC CTC TTC TAC ACA GTA GTG ACA       864
Ser Pro Gly Met Asp Lys Phe Leu Ala Leu Phe Tyr Thr Val Val Thr
        275                 280                 285

TCC ATG CTG AAC CCT ATC ATC TAT AGT TTA AGG AAC AAG GAA GTC AAG       912
Ser Met Leu Asn Pro Ile Ile Tyr Ser Leu Arg Asn Lys Glu Val Lys
290                 295                 300

GCA GCA CTG AGA AGA ACT CTG GGC CTG AAA AAA ATT CTG TCA ATT AAT       960
Ala Ala Leu Arg Arg Thr Leu Gly Leu Lys Lys Ile Leu Ser Ile Asn
305                 310                 315                 320

AGG TAA                                                               966
Arg (2) INFORMATION FOR SEQ ID NO:6:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

ATG AGT GTC AAC TGT TCG CTG TGG CAG GAG AAT AGT TTG TCT GTC AAA        48
Met Ser Val Asn Cys Ser Leu Trp Gln Glu Asn Ser Leu Ser Val Lys
1               5                   10                  15

CGC TTT GCA TTT GCC AAG TTC TCT GAG GTC CCT GGA GAA TGC TTC CTC        96
Arg Phe Ala Phe Ala Lys Phe Ser Glu Val Pro Gly Glu Cys Phe Leu
                20                  25                  30

CTG TTC ACC CTC ATC CTT CTC ATG TTC TTA GTA TCA CTA ACA GGA AAT       144
Leu Phe Thr Leu Ile Leu Leu Met Phe Leu Val Ser Leu Thr Gly Asn
            35                  40                  45

GCT CTC ATA GCC CTT GCT GNT TGT ACC AGT CCA TCT CTA CAC ACC CCC       192
Ala Leu Ile Ala Leu Ala Xaa Cys Thr Ser Pro Ser Leu His Thr Pro
        50                  55                  60
```

```
ATG TAC TTC TTT CTG GCC AAC TTG TCT CTC CTG GAG ATT GGC TAT ACT       240
Met Tyr Phe Phe Leu Ala Asn Leu Ser Leu Leu Glu Ile Gly Tyr Thr
 65              70                  75                      80

TGC TCT GTC ATA CCC AAG ATG CTG CAG AGC CTT GTG AGT GAG GCC AGA       288
Cys Ser Val Ile Pro Lys Met Leu Gln Ser Leu Val Ser Glu Ala Arg
                 85                  90                  95

GAG ATC TCT AGG GAG GGA TGT GCC ACA CAG ATG TTT TTC TTC ACA TTT       336
Glu Ile Ser Arg Glu Gly Cys Ala Thr Gln Met Phe Phe Phe Thr Phe
             100                 105                 110

TTT GGC ATA ACT GAG TGC TGC CTA TTG GCA GCC ATG GCC TTT GAC CGC       384
Phe Gly Ile Thr Glu Cys Cys Leu Leu Ala Ala Met Ala Phe Asp Arg
         115                 120                 125

TGC ATG GGC ATA TGC TCC CCA CTC CAC TAT GCA ACC CGA ATG AGT CGT       432
Cys Met Gly Ile Cys Ser Pro Leu His Tyr Ala Thr Arg Met Ser Arg
     130                 135                 140

GAG GTA TGT GCC CAT TTG GCA ATT GTT TCA TGG GGA ATG GGA TGC ATA       480
Glu Val Cys Ala His Leu Ala Ile Val Ser Trp Gly Met Gly Cys Ile
145                 150                 155                 160

GTA GGT CTG GGA CAG ACC AAT TTN ATT TNC TCC TTG AAC TTC TGT GGA       528
Val Gly Leu Gly Gln Thr Asn Xaa Ile Xaa Ser Leu Asn Phe Cys Gly
                 165                 170                 175

CCT TGT GAG ATA GAC CAC TTC TTC TGT GAC CTT CCA CCT CTC CTG GCA       576
Pro Cys Glu Ile Asp His Phe Phe Cys Asp Leu Pro Pro Leu Leu Ala
             180                 185                 190

CTT GCC TGT GGT GAT ACA TCC CAA AAC GAG GCT GCC ATC TTT GTG GCA       624
Leu Ala Cys Gly Asp Thr Ser Gln Asn Glu Ala Ala Ile Phe Val Ala
         195                 200                 205

GCA ATC CTC TGT ATA TCT AGT CCA TTT TTG GTG ATC CTT TAT TCT TAT       672
Ala Ile Leu Cys Ile Ser Ser Pro Phe Leu Val Ile Leu Tyr Ser Tyr
210                 215                 220

GTC AGA ATT CTC GTT GCA GTG CTG GTG ATG CCT TCA CCT GAG GGG CGC       720
Val Arg Ile Leu Val Ala Val Leu Val Met Pro Ser Pro Glu Gly Arg
225                 230                 235                 240

CAT AAA GCT CTT TCC ACC TGT TCC TCA CAC CTA CTT GTA GTC ACA CTC       768
His Lys Ala Leu Ser Thr Cys Ser Ser His Leu Leu Val Val Thr Leu
                 245                 250                 255

TTT TAT GGC TCT GTG TCC TTT ACC TAT TTG AGG CCC AAG TCT AGC CAC       816
Phe Tyr Gly Ser Val Ser Phe Thr Tyr Leu Arg Pro Lys Ser Ser His
             260                 265                 270

TCA CCA GGA ATG GAC AAA CTC TTG GCC CTC TTC TAC ACA GCA GTG ACA       864
Ser Pro Gly Met Asp Lys Leu Leu Ala Leu Phe Tyr Thr Ala Val Thr
         275                 280                 285

TCC ATG CTG AAC CCT ATC ATC TAC AGT CTA AGG AAC AAG GAA GTC AAG       912
Ser Met Leu Asn Pro Ile Ile Tyr Ser Leu Arg Asn Lys Glu Val Lys
     290                 295                 300

GCA GCA CTG AGA AGA ACT CTC GAC CTG AAA AAA ATT ATG TCA ATT AAT       960
Ala Ala Leu Arg Arg Thr Leu Asp Leu Lys Lys Ile Met Ser Ile Asn
305                 310                 315                 320

AGG TAA                                                                966
Arg
```

(2) INFORMATION FOR SEQ ID NO:7:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
ATG AGT GTC AAC TGT TCT CTG TGG CAG GAG AAT AGT TTG TCT GTC AAA        48
Met Ser Val Asn Cys Ser Leu Trp Gln Glu Asn Ser Leu Ser Val Lys
 1               5                  10                  15

CGC TTT GCA TTT GCC AAG TTC TCT GAG GTC CCT GGA GAA TGC TTC CTC        96
Arg Phe Ala Phe Ala Lys Phe Ser Glu Val Pro Gly Glu Cys Phe Leu
             20                  25                  30

CTG TTC ACC CTC ATC CTT CTC ATG TTC TTA GTA TCA CTA ACA GGA AAT       144
Leu Phe Thr Leu Ile Leu Leu Met Phe Leu Val Ser Leu Thr Gly Asn
         35                  40                  45

ACT CTC ATA GCC CTT GCT ATT TGT ACC AGT CCA TCT CTA CAC ACC CCC       192
Thr Leu Ile Ala Leu Ala Ile Cys Thr Ser Pro Ser Leu His Thr Pro
     50                  55                  60

ATG TAC TTC TTT CTG GCC AAC TTG TCT CTC CTG GAG ATT GGC TAT ACT       240
Met Tyr Phe Phe Leu Ala Asn Leu Ser Leu Leu Glu Ile Gly Tyr Thr
 65                  70                  75                  80

TGC TCT GTC ATA CCC AAG ATG CTG CAG AGC CTT GTG AGT GAG GCC CGA       288
Cys Ser Val Ile Pro Lys Met Leu Gln Ser Leu Val Ser Glu Ala Arg
                 85                  90                  95

GGG ATC TCT TGG GAG GGT TGT GCC TCA CAG ATG TTC TTC TTC ATA TTC       336
Gly Ile Ser Trp Glu Gly Cys Ala Ser Gln Met Phe Phe Phe Ile Phe
            100                 105                 110

TTT GGT ATA ACT GAG TGC TGC CTA TTG GCA GCC ATG GCC TTT GAC CGC       384
Phe Gly Ile Thr Glu Cys Cys Leu Leu Ala Ala Met Ala Phe Asp Arg
        115                 120                 125

TAT ATG GCT ATA TGT TCC CCA CTC CAC TAT GCA ACC CGA ATG AGT CGT       432
Tyr Met Ala Ile Cys Ser Pro Leu His Tyr Ala Thr Arg Met Ser Arg
    130                 135                 140

GGG GTA TGT GCC TAT TTG GCA ATT GTC TCA TGG GTG ATG GGA TGC ATA       480
Gly Val Cys Ala Tyr Leu Ala Ile Val Ser Trp Val Met Gly Cys Ile
145                 150                 155                 160

GTA GGT CTG GGA CAG ACC AAT TTT ATT TTC TCC TTG AAC TTC TGT GGA       528
Val Gly Leu Gly Gln Thr Asn Phe Ile Phe Ser Leu Asn Phe Cys Gly
                165                 170                 175

CCC TGT GAG ATA GAC CAC TTC TTC TGT GAC CTT CCA CCT CTC CTG GCA       576
Pro Cys Glu Ile Asp His Phe Phe Cys Asp Leu Pro Pro Leu Leu Ala
            180                 185                 190

CTT GCC TGT GGT GAT ACA TCC CAA AAT GAG GCT GCC ATC TTT GTG GCA       624
Leu Ala Cys Gly Asp Thr Ser Gln Asn Glu Ala Ala Ile Phe Val Ala
        195                 200                 205

GCA GTG CTC TGC ATA TTT AGT CCA TTT TTA CTG ATC ATT TCT TCC TAT       672
Ala Val Leu Cys Ile Phe Ser Pro Phe Leu Leu Ile Ile Ser Ser Tyr
    210                 215                 220

GTC AGA ATT CTC GTT GCA GTG CTG GTG ATG CCT TCA CCT GAG GGG CGC       720
Val Arg Ile Leu Val Ala Val Leu Val Met Pro Ser Pro Glu Gly Arg
225                 230                 235                 240

CAT AAA GCT CTC TCT ACC TGT TCA TCT CAC CTA CTT GTA GTC ACA CTC       768
His Lys Ala Leu Ser Thr Cys Ser Ser His Leu Leu Val Val Thr Leu
                245                 250                 255

TTC TAT GGC TCA ACA TCT GCC ACC TAT TTG AGG TCC AAG TCT AGC CAC       816
Phe Tyr Gly Ser Thr Ser Ala Thr Tyr Leu Arg Ser Lys Ser Ser His
            260                 265                 270

TCA CCA GGA GTG GAC AAA CTC TTG GCC CTC TTC TAT ACA TCA GTG ACA       864
Ser Pro Gly Val Asp Lys Leu Leu Ala Leu Phe Tyr Thr Ser Val Thr
        275                 280                 285

TCC ATG CTG AAT CCC ATC ATC TAC AGC TTA AGG AAC AAG GAA GTA AAG       912
Ser Met Leu Asn Pro Ile Ile Tyr Ser Leu Arg Asn Lys Glu Val Lys
    290                 295                 300

GGT GCA CTG AGA AGA ACT CTG GGC CTG AAG AAA GTT CTG ACA ATG AAA       960
```

```
Gly Ala Leu Arg Arg Thr Leu Gly Leu Lys Lys Val Leu Thr Met Lys
305                 310                 315                 320

AGG TAA                                                                   966
Arg (2) INFORMATION FOR SEQ ID NO:8:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

ATG ACT GTC AAC TGT TCT CTG TGG CAG GAG AAT AGT TTG TCT GTC AAA          48
Met Thr Val Asn Cys Ser Leu Trp Gln Glu Asn Ser Leu Ser Val Lys
1               5                   10                  15

CGT TTT GCA TTT GCC AAG TTC TCT GAG GTC CCT GGA GAA TGC TTC CTC          96
Arg Phe Ala Phe Ala Lys Phe Ser Glu Val Pro Gly Glu Cys Phe Leu
                20                  25                  30

CTG TTC ACC CTC ATC CTT CTC ATG TTC TTA GTA TCA CTA ACA GGA AAT         144
Leu Phe Thr Leu Ile Leu Leu Met Phe Leu Val Ser Leu Thr Gly Asn
            35                  40                  45

GCT CTC ATA GCC CTT GCT ATT TGT ACC AGT CCA TCT CTA CAC ACC CCC         192
Ala Leu Ile Ala Leu Ala Ile Cys Thr Ser Pro Ser Leu His Thr Pro
        50                  55                  60

ATG TAC TTC TTT CTG GCC AAC TTG TCT CTC CTG GAG ATT GGC TAT ACT         240
Met Tyr Phe Phe Leu Ala Asn Leu Ser Leu Leu Glu Ile Gly Tyr Thr
65                  70                  75                  80

TGC TCT GTC ATA CCC AAG ATG CTG CAG AGT CTT GTG AGT GAG GCC CGA         288
Cys Ser Val Ile Pro Lys Met Leu Gln Ser Leu Val Ser Glu Ala Arg
                85                  90                  95

GAG ATC TTT CAG GTG GGA TGT GCC ACA CAG ATG TTT TTC TTC ATA TTC         336
Glu Ile Phe Gln Val Gly Cys Ala Thr Gln Met Phe Phe Phe Ile Phe
            100                 105                 110

TTT GGT ATA ACT GAG TGC TGC CTA TTG GCA GCC ATG GCC TTT GAC CGC         384
Phe Gly Ile Thr Glu Cys Cys Leu Leu Ala Ala Met Ala Phe Asp Arg
        115                 120                 125

TAT ATG GCT ATA TGT TCC CCA CTC CAC TAT GCA ACC CGA ATG AGT CGT         432
Tyr Met Ala Ile Cys Ser Pro Leu His Tyr Ala Thr Arg Met Ser Arg
130                 135                 140

GAG GTA TGT GCC CAC TTG GCA ATT GTT TCA TGG GTG ATG GGA TGC ATA         480
Glu Val Cys Ala His Leu Ala Ile Val Ser Trp Val Met Gly Cys Ile
145                 150                 155                 160

GTA GGT CTG GGA CAG ACC AAT TTT ATT TTC TCC TTG AAC TTC TGT GGA         528
Val Gly Leu Gly Gln Thr Asn Phe Ile Phe Ser Leu Asn Phe Cys Gly
                165                 170                 175

CCC TGT GAG ATA GAC CAC TTC TTC TGT GAT CTT CCA CCT CTC CTG GCA         576
Pro Cys Glu Ile Asp His Phe Phe Cys Asp Leu Pro Pro Leu Leu Ala
            180                 185                 190

CTT GCC TGT GGT GAT ACA TCC CAA ATT GAG GCT GCC ATC TTT GTG GTA         624
Leu Ala Cys Gly Asp Thr Ser Gln Ile Glu Ala Ala Ile Phe Val Val
        195                 200                 205

GTT GTC CTC TGC ATA TCT AGC CCT TTT TTG CTG ATC ATT TAT TCT TAT         672
Val Val Leu Cys Ile Ser Ser Pro Phe Leu Leu Ile Ile Tyr Ser Tyr
210                 215                 220

GTC AGA ATT CTC GTT GCA GTG CTG GTG ATG CCT TCA CCT GAG GGG CGC         720
Val Arg Ile Leu Val Ala Val Leu Val Met Pro Ser Pro Glu Gly Arg
225                 230                 235                 240
```

```
CAC AAA GCC CTT TCA ACC TGT TCC TCC CAC CTA CTT GTA GTC ACA CTC        768
His Lys Ala Leu Ser Thr Cys Ser Ser His Leu Leu Val Val Thr Leu
                245                 250                 255

TTT TAT GGC TCA GGA TCT GTT ACC TAT TTG AGG CCT AAG TCT AGC CAC        816
Phe Tyr Gly Ser Gly Ser Val Thr Tyr Leu Arg Pro Lys Ser Ser His
                260                 265                 270

TCA CCA GGA ATG GAC AAA CTC TTG GCC CTC TTC TAC ACA GCA GTG ACA        864
Ser Pro Gly Met Asp Lys Leu Leu Ala Leu Phe Tyr Thr Ala Val Thr
                275                 280                 285

TCC ATG TTG AAC CCT ATC ATC TAT AGT TTA AGG AAC AAG GAT GTC AAG        912
Ser Met Leu Asn Pro Ile Ile Tyr Ser Leu Arg Asn Lys Asp Val Lys
                290                 295                 300

GCA GCA CTG AGA AGA ATT CTG GCC CTG AAA AAA ATT CTG TCA ATA AAT        960
Ala Ala Leu Arg Arg Ile Leu Ala Leu Lys Lys Ile Leu Ser Ile Asn
305                 310                 315                 320

AAG TAA                                                                966
Lys (2) INFORMATION FOR SEQ ID NO:9:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

ATG GAA TGG CTA ATG ACA GAG GAG ACA AGG AAT GGG ACT TTG GTC CTG         48
Met Glu Trp Leu Met Thr Glu Glu Thr Arg Asn Gly Thr Leu Val Leu
1               5                   10                  15

GAG TTC ATC CTT GAG GGG TAC CCT GTG GCC GAG CAC CTG AAG ATC CTC         96
Glu Phe Ile Leu Glu Gly Tyr Pro Val Ala Glu His Leu Lys Ile Leu
                20                  25                  30

TTC TTC CTA CTG CAC TTG CTG GCC TAC TTG GCC TCC CTC ATG GGC AAC        144
Phe Phe Leu Leu His Leu Leu Ala Tyr Leu Ala Ser Leu Met Gly Asn
                35                  40                  45

ATG CTC ATA ATT ACC ATC ACC TGT GTG GAC CAC CGA CTG CAG ACG CCC        192
Met Leu Ile Ile Thr Ile Thr Cys Val Asp His Arg Leu Gln Thr Pro
50                  55                  60

ATG TAC TTC TTT CTC AGC ACC TTC TCT TTT GTG GAG TGT TGT TTT ATA        240
Met Tyr Phe Phe Leu Ser Thr Phe Ser Phe Val Glu Cys Cys Phe Ile
65                  70                  75                  80

ACT ACT GCT ATC CCC CAG CTC CTC ACC ATC ATT CTG TCA GGG AGG CAA        288
Thr Thr Ala Ile Pro Gln Leu Leu Thr Ile Ile Leu Ser Gly Arg Gln
                85                  90                  95

AAG ATT CCC TTT GGG GTC TGC TTC TCA CAG GCC TTC GTC TAT CTT GTC        336
Lys Ile Pro Phe Gly Val Cys Phe Ser Gln Ala Phe Val Tyr Leu Val
                100                 105                 110

GTG GGG GCA ACA GGT TTT TTC CTT TTG GCT GCG TTA TCC CTG GAC CGC        384
Val Gly Ala Thr Gly Phe Phe Leu Leu Ala Ala Leu Ser Leu Asp Arg
                115                 120                 125

TTT CTG GCC ATC TGC AAA CCT CTA CAT TAT CCA ACC ATC ATG AGC CCA        432
Phe Leu Ala Ile Cys Lys Pro Leu His Tyr Pro Thr Ile Met Ser Pro
130                 135                 140

AGG ATG TGC TTC CTT CTC GTT ACT GTC TGT TTA TTT TTG GGC TTC CTC        480
Arg Met Cys Phe Leu Leu Val Thr Val Cys Leu Phe Leu Gly Phe Leu
145                 150                 155                 160

TTC ATG GCC AGT CCA GTT GTG ATG CTT TCC AAG ACA TTT TAC TGT GGT        528
Phe Met Ala Ser Pro Val Val Met Leu Ser Lys Thr Phe Tyr Cys Gly
                165                 170                 175
```

```
CCA AAC ATT ATT CCT CAC TTT TTC TGT GAT TTT GGA CCA CTG GCA AAT        576
Pro Asn Ile Ile Pro His Phe Phe Cys Asp Phe Gly Pro Leu Ala Asn
            180                 185                 190

CTC TCC TGT TCA GAA ACC AGG TCT ATT GAG ATG CTG TTT TTT ACC CTT        624
Leu Ser Cys Ser Glu Thr Arg Ser Ile Glu Met Leu Phe Phe Thr Leu
            195                 200                 205

GCT GTA ATT GTG CTT TTT GCT TCC TTT CTT ATA GCC ATC TTT GCA TAC        672
Ala Val Ile Val Leu Phe Ala Ser Phe Leu Ile Ala Ile Phe Ala Tyr
            210                 215                 220

AGC AAT ATA GTA GTC ACC ATA GTG AGA CTC CCT TCA GCC AGG GAG CGA        720
Ser Asn Ile Val Val Thr Ile Val Arg Leu Pro Ser Ala Arg Glu Arg
225             230                 235                 240

CAG AGA GCT TTT TCC ACC TGC TCC TCT CAT CTC ATT GTC CTC TCT CTA        768
Gln Arg Ala Phe Ser Thr Cys Ser Ser His Leu Ile Val Leu Ser Leu
                245                 250                 255

ATG TAT GGC AGC TGT GCA TTT ATA TAC CTG AAG CCA AAG CAG AGA AGC        816
Met Tyr Gly Ser Cys Ala Phe Ile Tyr Leu Lys Pro Lys Gln Arg Ser
            260                 265                 270

AGA GTG GAC ACC AAC AGA GAG GCT GCT CTT GTG AAC ATG GTT GTG ACA        864
Arg Val Asp Thr Asn Arg Glu Ala Ala Leu Val Asn Met Val Val Thr
            275                 280                 285

CCC CTT CTG AAC CCT GTC ATC TAC ACC CTG CGC AAC AAG CAG GTC CAC        912
Pro Leu Leu Asn Pro Val Ile Tyr Thr Leu Arg Asn Lys Gln Val His
            290                 295                 300

CAG GCT CTC AGG GAT GCT CTG TCC AGG CTT CAA TTA CAC AGA TAT CAG        960
Gln Ala Leu Arg Asp Ala Leu Ser Arg Leu Gln Leu His Arg Tyr Gln
305             310                 315                 320

AGG AGG AAG GCT CCT TTC CTT TGA                                        984
Arg Arg Lys Ala Pro Phe Leu
            325

(2) INFORMATION FOR SEQ ID NO:10:

(i) SEQUENCE CHARACTERISTICS:
        (A) LENGTH: 321 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:10:

Met Thr Val Asn Cys Ser Leu Trp Gln Glu Asn Ser Leu Thr Val Lys
1               5                   10                  15

His Phe Ala Phe Ala Lys Phe Ser Glu Val Pro Gly Glu Cys Phe Leu
            20                  25                  30

Leu Phe Asn Leu Ile Leu Leu Met Phe Leu Val Ser Leu Thr Gly Asn
        35                  40                  45

Thr Leu Ile Val Leu Ala Ile Cys Thr Ser Pro Ser Leu His Thr Pro
    50                  55                  60

Met Tyr Phe Phe Leu Ala Asn Leu Ser Leu Leu Glu Ile Gly Tyr Thr
65              70                  75                  80

Cys Ser Val Ile Pro Lys Met Leu Gln Ser Leu Val Ser Glu Ala Arg
                85                  90                  95

Glu Ile Ser Arg Glu Gly Cys Ala Thr Gln Met Phe Phe Phe Ala Phe
            100                 105                 110

Phe Gly Ile Thr Glu Cys Cys Leu Leu Ala Ala Met Ala Phe Asp Arg
        115                 120                 125

Cys Met Ala Ile Cys Ser Pro Leu His Tyr Ala Thr Arg Met Ser Arg
```

```
          130                 135                 140
Glu Val Cys Ala His Leu Ala Ile Val Ser Trp Gly Met Gly Cys Ile
145                 150                 155                 160

Val Ser Leu Gly Gln Thr Asn Phe Ile Phe Ser Leu Asn Phe Cys Gly
                165                 170                 175

Pro Cys Glu Ile Asp His Phe Phe Cys Asp Leu Pro Pro Leu Leu Ala
            180                 185                 190

Leu Ala Cys Gly Asp Thr Ser Gln Asn Glu Ala Ala Ile Phe Val Val
        195                 200                 205

Ala Val Leu Cys Ile Ser Ser Pro Phe Leu Leu Ile Ile Tyr Ser Tyr
    210                 215                 220

Val Lys Ile Leu Ile Ala Val Leu Leu Met Pro Ser Pro Glu Gly Arg
225                 230                 235                 240

His Lys Ala Leu Ser Thr Cys Ser Ser His Leu Leu Val Val Thr Leu
                245                 250                 255

Phe Tyr Gly Ser Ala Cys Ile Thr Tyr Leu Arg Pro Lys Ser Ser His
                260                 265                 270

Ser Pro Gly Met Asp Lys Phe Leu Ala Leu Phe Tyr Thr Val Val Thr
            275                 280                 285

Ser Met Leu Asn Pro Ile Ile Tyr Ser Leu Arg Asn Lys Glu Val Lys
        290                 295                 300

Ala Ala Leu Arg Arg Thr Leu Gly Leu Lys Lys Ile Leu Ser Ile Asn
305                 310                 315                 320

Arg (2) INFORMATION FOR SEQ ID NO:11:

(i) SEQUENCE CHARACTERISTICS:
        (A) LENGTH: 321 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:11:

Met Ser Val Asn Cys Ser Leu Trp Gln Glu Asn Ser Leu Ser Val Lys
1               5                   10                  15

Arg Phe Ala Phe Ala Lys Phe Ser Glu Val Pro Gly Glu Cys Phe Leu
                20                  25                  30

Leu Phe Thr Leu Ile Leu Leu Met Phe Leu Val Ser Leu Thr Gly Asn
            35                  40                  45

Ala Leu Ile Ala Leu Ala Xaa Cys Thr Ser Pro Ser Leu His Thr Pro
        50                  55                  60

Met Tyr Phe Phe Leu Ala Asn Leu Ser Leu Leu Glu Ile Gly Tyr Thr
65                  70                  75                  80

Cys Ser Val Ile Pro Lys Met Leu Gln Ser Leu Val Ser Glu Ala Arg
                85                  90                  95

Glu Ile Ser Arg Glu Gly Cys Ala Thr Gln Met Phe Phe Phe Thr Phe
                100                 105                 110

Phe Gly Ile Thr Glu Cys Cys Leu Leu Ala Ala Met Ala Phe Asp Arg
            115                 120                 125

Cys Met Gly Ile Cys Ser Pro Leu His Tyr Ala Thr Arg Met Ser Arg
        130                 135                 140

Glu Val Cys Ala His Leu Ala Ile Val Ser Trp Gly Met Gly Cys Ile
145                 150                 155                 160
```

```
Val Gly Leu Gly Gln Thr Asn Xaa Ile Xaa Ser Leu Asn Phe Cys Gly
                165                 170                 175

Pro Cys Glu Ile Asp His Phe Phe Cys Asp Leu Pro Pro Leu Leu Ala
            180                 185                 190

Leu Ala Cys Gly Asp Thr Ser Gln Asn Glu Ala Ala Ile Phe Val Ala
        195                 200                 205

Ala Ile Leu Cys Ile Ser Ser Pro Phe Leu Val Ile Leu Tyr Ser Tyr
    210                 215                 220

Val Arg Ile Leu Val Ala Val Leu Val Met Pro Ser Pro Glu Gly Arg
225                 230                 235                 240

His Lys Ala Leu Ser Thr Cys Ser Ser His Leu Leu Val Val Thr Leu
                245                 250                 255

Phe Tyr Gly Ser Val Ser Phe Thr Tyr Leu Arg Pro Lys Ser Ser His
            260                 265                 270

Ser Pro Gly Met Asp Lys Leu Leu Ala Leu Phe Tyr Thr Ala Val Thr
        275                 280                 285

Ser Met Leu Asn Pro Ile Ile Tyr Ser Leu Arg Asn Lys Glu Val Lys
    290                 295                 300

Ala Ala Leu Arg Arg Thr Leu Asp Leu Lys Lys Ile Met Ser Ile Asn
305                 310                 315                 320

Arg
```

(2) INFORMATION FOR SEQ ID NO:12:

(i) SEQUENCE CHARACTERISTICS:
        (A) LENGTH: 321 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser Val Asn Cys Ser Leu Trp Gln Glu Asn Ser Leu Ser Val Lys
  1               5                  10                  15

Arg Phe Ala Phe Ala Lys Phe Ser Glu Val Pro Gly Glu Cys Phe Leu
                 20                  25                  30

Leu Phe Thr Leu Ile Leu Leu Met Phe Leu Val Ser Leu Thr Gly Asn
             35                  40                  45

Thr Leu Ile Ala Leu Ala Ile Cys Thr Ser Pro Ser Leu His Thr Pro
         50                  55                  60

Met Tyr Phe Phe Leu Ala Asn Leu Ser Leu Leu Glu Ile Gly Tyr Thr
 65                  70                  75                  80

Cys Ser Val Ile Pro Lys Met Leu Gln Ser Leu Val Ser Glu Ala Arg
                 85                  90                  95

Gly Ile Ser Trp Glu Gly Cys Ala Ser Gln Met Phe Phe Ile Phe
                100                 105                 110 Phe

Phe Gly Ile Thr Glu Cys Cys Leu Leu Ala Ala Met Ala Phe Asp Arg
            115                 120                 125

Tyr Met Ala Ile Cys Ser Pro Leu His Tyr Ala Thr Arg Met Ser Arg
        130                 135                 140

Gly Val Cys Ala Tyr Leu Ala Ile Val Ser Trp Val Met Gly Cys Ile
145                 150                 155                 160

Val Gly Leu Gly Gln Thr Asn Phe Ile Phe Ser Leu Asn Phe Cys Gly
                165                 170                 175

Pro Cys Glu Ile Asp His Phe Phe Cys Asp Leu Pro Pro Leu Leu Ala
```

```
                    180                 185                 190
Leu Ala Cys Gly Asp Thr Ser Gln Asn Glu Ala Ala Ile Phe Val Ala
            195                 200                 205

Ala Val Leu Cys Ile Phe Ser Pro Phe Leu Leu Ile Ile Ser Ser Tyr
    210                 215                 220

Val Arg Ile Leu Val Ala Val Leu Val Met Pro Ser Pro Glu Gly Arg
225                 230                 235                 240

His Lys Ala Leu Ser Thr Cys Ser Ser His Leu Leu Val Val Thr Leu
                245                 250                 255

Phe Tyr Gly Ser Thr Ser Ala Thr Tyr Leu Arg Ser Lys Ser Ser His
            260                 265                 270

Ser Pro Gly Val Asp Lys Leu Leu Ala Leu Phe Tyr Thr Ser Val Thr
        275                 280                 285

Ser Met Leu Asn Pro Ile Ile Tyr Ser Leu Arg Asn Lys Glu Val Lys
    290                 295                 300

Gly Ala Leu Arg Arg Thr Leu Gly Leu Lys Lys Val Leu Thr Met Lys
305                 310                 315                 320

Arg
```

(2) INFORMATION FOR SEQ ID NO:13:

(i) SEQUENCE CHARACTERISTICS:
        (A) LENGTH: 321 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:13:

```
Met Thr Val Asn Cys Ser Leu Trp Gln Glu Asn Ser Leu Ser Val Lys
1               5                   10                  15

Arg Phe Ala Phe Ala Lys Phe Ser Glu Val Pro Gly Glu Cys Phe Leu
            20                  25                  30

Leu Phe Thr Leu Ile Leu Leu Met Phe Leu Val Ser Leu Thr Gly Asn
        35                  40                  45

Ala Leu Ile Ala Leu Ala Ile Cys Thr Ser Pro Ser Leu His Thr Pro
    50                  55                  60

Met Tyr Phe Phe Leu Ala Asn Leu Ser Leu Leu Glu Ile Gly Tyr Thr
65                  70                  75                  80

Cys Ser Val Ile Pro Lys Met Leu Gln Ser Leu Val Ser Glu Ala Arg
                85                  90                  95

Glu Ile Phe Gln Val Gly Cys Ala Thr Gln Met Phe Phe Ile Phe
            100                 105                 110

Phe Gly Ile Thr Glu Cys Cys Leu Leu Ala Ala Met Ala Phe Asp Arg
        115                 120                 125

Tyr Met Ala Ile Cys Ser Pro Leu His Tyr Ala Thr Arg Met Ser Arg
    130                 135                 140

Glu Val Cys Ala His Leu Ala Ile Val Ser Trp Val Met Gly Cys Ile
145                 150                 155                 160

Val Gly Leu Gly Gln Thr Asn Phe Ile Phe Ser Leu Asn Phe Cys Gly
                165                 170                 175

Pro Cys Glu Ile Asp His Phe Phe Cys Asp Leu Pro Pro Leu Leu Ala
            180                 185                 190

Leu Ala Cys Gly Asp Thr Ser Gln Ile Glu Ala Ala Ile Phe Val Val
        195                 200                 205
```

Val Val Leu Cys Ile Ser Ser Pro Phe Leu Ile Ile Tyr Ser Tyr
    210                 215                 220

Val Arg Ile Leu Val Ala Val Leu Val Met Pro Ser Pro Glu Gly Arg
225                 230                 235                 240

His Lys Ala Leu Ser Thr Cys Ser Ser His Leu Leu Val Thr Leu
                245                 250                 255

Phe Tyr Gly Ser Gly Ser Val Thr Tyr Leu Arg Pro Lys Ser Ser His
                260                 265                 270

Ser Pro Gly Met Asp Lys Leu Leu Ala Leu Phe Tyr Thr Ala Val Thr
            275                 280                 285

Ser Met Leu Asn Pro Ile Ile Tyr Ser Leu Arg Asn Lys Asp Val Lys
        290                 295                 300

Ala Ala Leu Arg Arg Ile Leu Ala Leu Lys Lys Ile Leu Ser Ile Asn
305                 310                 315                 320

Lys (2) INFORMATION FOR SEQ ID NO:14:

(i) SEQUENCE CHARACTERISTICS:
        (A) LENGTH: 327 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:14:

Met Glu Trp Leu Met Thr Glu Glu Thr Arg Asn Gly Thr Leu Val Leu
1               5                   10                  15

Glu Phe Ile Leu Glu Gly Tyr Pro Val Ala Glu His Leu Lys Ile Leu
            20                  25                  30

Phe Phe Leu Leu His Leu Leu Ala Tyr Leu Ala Ser Leu Met Gly Asn
            35                  40                  45

Met Leu Ile Ile Thr Ile Thr Cys Val Asp His Arg Leu Gln Thr Pro
    50                  55                  60

Met Tyr Phe Phe Leu Ser Thr Phe Ser Phe Val Glu Cys Cys Phe Ile
65                  70                  75                  80

Thr Thr Ala Ile Pro Gln Leu Leu Thr Ile Ile Leu Ser Gly Arg Gln
                85                  90                  95

Lys Ile Pro Phe Gly Val Cys Ser Gln Ala Phe Val Tyr Leu Val
            100                 105                 110

Val Gly Ala Thr Gly Phe Phe Leu Leu Ala Ala Leu Ser Leu Asp Arg
            115                 120                 125

Phe Leu Ala Ile Cys Lys Pro Leu His Tyr Pro Thr Ile Met Ser Pro
    130                 135                 140

Arg Met Cys Phe Leu Leu Val Thr Val Cys Leu Phe Leu Gly Phe Leu
145                 150                 155                 160

Phe Met Ala Ser Pro Val Val Met Leu Ser Lys Thr Phe Tyr Cys Gly
                165                 170                 175

Pro Asn Ile Ile Pro His Phe Phe Cys Asp Phe Gly Pro Leu Ala Asn
            180                 185                 190

Leu Ser Cys Ser Glu Thr Arg Ser Ile Glu Met Leu Phe Phe Thr Leu
            195                 200                 205

Ala Val Ile Val Leu Phe Ala Ser Phe Leu Ile Ala Ile Phe Ala Tyr
    210                 215                 220

```
Ser Asn Ile Val Val Thr Ile Val Arg Leu Pro Ser Ala Arg Glu Arg
225                 230                 235                 240

Gln Arg Ala Phe Ser Thr Cys Ser Ser His Leu Ile Val Leu Ser Leu
            245                 250                 255

Met Tyr Gly Ser Cys Ala Phe Ile Tyr Leu Lys Pro Lys Gln Arg Ser
            260                 265                 270

Arg Val Asp Thr Asn Arg Glu Ala Ala Leu Val Asn Met Val Val Thr
            275                 280                 285

Pro Leu Leu Asn Pro Val Ile Tyr Thr Leu Arg Asn Lys Gln Val His
            290                 295                 300

Gln Ala Leu Arg Asp Ala Leu Ser Arg Leu Gln Leu His Arg Tyr Gln
305                 310                 315                 320

Arg Arg Lys Ala Pro Phe Leu
                325
```

(2) INFORMATION FOR SEQ ID NO:15:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: DNA (synthetic)

(xi) SEQUENCE DESCRIPTION: SEQ ID NO:15:

```
ATG ACT GTC AAC TGT TCT CTG TGG CAG GAG AAT AGT TTG TCT GTC AAA    48
Met Thr Val Asn Cys Ser Leu Trp Gln Glu Asn Ser Leu Ser Val Lys
 1               5                  10                  15

CGT TTT GCA TTT GCC AAG TTC TCT GAG GTC CCT GGA GAA TGC TTC CTC    96
Arg Phe Ala Phe Ala Lys Phe Ser Glu Val Pro Gly Glu Cys Phe Leu
            20                  25                  30
```

(2) INFORMATION FOR SEQ ID NO:16:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:16:

```
Met Thr Val Asn Cys Ser Leu Trp Gln Glu Asn Ser Leu Ser Val Lys
 1               5                  10                  15

Arg Phe Ala Phe Ala Lys Phe Ser Glu Val Pro Gly Glu Cys Phe Leu
            20                  25                  30
```

(2) INFORMATION FOR SEQ ID NO:17:

(i) SEQUENCE CHARACTERISTICS:
        (A) LENGTH: 178 amino acids
        (B) TYPE: amino acid
        (D) TOPOLOGY: unknown (ii) MOLECULE TYPE: protein (xi) SEQUENCE DESCRIPTION: SEQ ID NO:17:

```
Phe Leu Ala Asn Leu Ser Leu Leu Glu Ile Gly Tyr Thr Cys Ser Val
 1               5                  10                  15

Ile Pro Lys Met Leu Gln Ser Leu Val Ser Glu Ala Arg Glu Ile Ser
            20                  25                  30

Arg Glu Gly Cys Ala Thr Gln Met Phe Phe Phe Thr Phe Phe Gly Ile
```

-continued

```
            35                  40                  45
Thr Glu Cys Cys Leu Leu Ala Ala Met Ala Phe Asp Arg Cys Met Met
    50                  55                  60
Ile Cys Ser Pro Leu His Tyr Ala Thr Arg Met Ser Arg Glu Val Cys
65                  70                  75                  80
Ala His Leu Ala Ile Val Ser Trp Gly Met Gly Cys Thr Val Gly Leu
                85                  90                  95
Gly Gln Thr Asn Phe Ile Phe Ser Leu Asn Phe Cys Gly Pro Cys Glu
            100                 105                 110
Ile Asp His Phe Phe Cys Asp Leu Pro Pro Leu Leu Ala Leu Ala Cys
            115                 120                 125
Gly Asp Thr Ser Gln Asn Glu Ala Ala Ile Phe Val Ala Ala Ile Leu
            130                 135                 140
Cys Ile Ser Ser Pro Phe Leu Leu Ile Ile Tyr Ser Tyr Val Arg Ile
145                 150                 155                 160
Leu Val Ala Val Leu Val Met Pro Ser Pro Glu Gly Arg His Lys Ala
                165                 170                 175
Leu Ser
```

(2) INFORMATION FOR SEQ ID NO:18:

(i) SEQUENCE CHARACTERISTICS:
        (A) LENGTH: 321 amino acids
        (B) TYPE: amino acid
        (D) TOPOLOGY: unknown (ii) MOLECULE TYPE: protein (xi) SEQUENCE DESCRIPTION: SEQ ID NO:18:

```
Met Ile Val Asn Cys Ser Leu Trp Gln Glu Asn Ser Leu Thr Val Lys
1               5                   10                  15
His Phe Ala Phe Ala Lys Phe Ser Glu Val Pro Gly Glu Cys Phe Leu
                20                  25                  30
Leu Phe Asn Leu Ile Leu Leu Met Phe Leu Val Ser Leu Thr Gly Asn
            35                  40                  45
Ile Leu Ile Val Leu Ala Ile Cys Thr Ser Pro Ser Leu His Thr Pro
50                  55                  60
Met Tyr Phe Phe Leu Ala Asn Leu Ser Leu Leu Glu Ile Gly Tyr Thr
65                  70                  75                  80
Cys Ser Val Ile Pro Lys Met Leu Gln Ser Leu Val Ser Glu Ala Arg
                85                  90                  95
Glu Ile Ser Arg Glu Gly Cys Ala Thr Gln Met Phe Phe Phe Ala Phe
            100                 105                 110
Phe Gly Ile Thr Glu Cys Cys Leu Leu Ala Ala Met Ala Phe Asp Arg
            115                 120                 125
Cys Met Ala Ile Cys Ser Pro Leu His Tyr Ala Thr Arg Met Ser Arg
            130                 135                 140
Glu Val Cys Ala His Leu Ala Ile Val Ser Trp Gly Met Gly Cys Ile
145                 150                 155                 160
Val Ser Leu Gly Gln Thr Asn Phe Ile Phe Ser Leu Asn Phe Cys Gly
                165                 170                 175
Pro Cys Glu Ile Asp His Phe Phe Cys Asp Leu Pro Pro Leu Leu Ala
            180                 185                 190
Leu Ala Cys Gly Asp Thr Ser Gln Asn Glu Ala Ala Ile Phe Val Val
            195                 200                 205
```

Ala Val Leu Cys Ile Ser Ser Pro Phe Leu Ile Ile Tyr Ser Tyr
            210                 215                 220

Val Lys Ile Leu Ile Ala Val Leu Leu Met Pro Ser Pro Glu Gly Arg
225                 230                 235                 240

His Lys Ala Leu Ser Thr Cys Ser Ser His Leu Leu Val Val Thr Leu
                    245                 250                 255

Phe Tyr Gly Ser Ala Cys Ile Thr Tyr Leu Arg Pro Lys Ser Ser His
                260                 265                 270

Ser Pro Gly Met Asp Lys Phe Leu Ala Leu Phe Tyr Thr Val Val Thr
                275                 280                 285

Ser Met Leu Asn Pro Ile Ile Tyr Ser Leu Arg Asn Lys Glu Val Lys
290                 295                 300

Ala Ala Leu Arg Arg Thr Leu Gly Leu Lys Lys Ile Leu Ser Ile Asn
305                 310                 315                 320

Arg (2) INFORMATION FOR SEQ ID NO:19:

(i) SEQUENCE CHARACTERISTICS:
        (A) LENGTH: 321 amino acids
        (B) TYPE: amino acid
        (D) TOPOLOGY: unknown (ii) MOLECULE TYPE: protein (xi) SEQUENCE DESCRIPTION: SEQ ID NO:19:

Met Ser Val Asn Cys Ser Leu Trp Gln Glu Asn Ser Leu Ser Val Lys
1               5                   10                  15

Arg Phe Ala Phe Ala Lys Phe Ser Glu Val Pro Gly Glu Cys Phe Leu
                20                  25                  30

Leu Phe Thr Leu Ile Leu Leu Met Phe Leu Val Ser Leu Thr Gly Asn
                35                  40                  45

Ala Leu Ile Ala Leu Ala Ala Cys Thr Ser Pro Ser Leu His Thr Pro
50                  55                  60

Met Tyr Phe Phe Leu Ala Asn Leu Ser Leu Leu Glu Ile Gly Tyr Thr
65                  70                  75                  80

Cys Ser Val Ile Pro Lys Met Leu Gln Ser Leu Val Ser Glu Ala Arg
                85                  90                  95

Glu Ile Ser Arg Glu Gly Cys Ala Thr Gln Met Phe Phe Thr Phe
                100                 105                 110

Phe Gly Ile Thr Glu Cys Cys Leu Leu Ala Ala Met Ala Phe Asp Arg
                115                 120                 125

Cys Met Gly Ile Cys Ser Pro Leu His Tyr Ala Thr Arg Met Ser Arg
130                 135                 140

Glu Val Cys Ala His Leu Ala Ile Val Ser Trp Gly Met Gly Cys Ile
145                 150                 155                 160

Val Gly Leu Gly Gln Thr Asn Asn Ile Ile Ser Leu Asn Phe Cys Gly
                165                 170                 175

Pro Cys Glu Ile Asp His Phe Phe Cys Asp Leu Pro Pro Leu Leu Ala
                180                 185                 190

Leu Ala Cys Gly Asp Thr Ser Gln Asn Glu Ala Ala Ile Phe Val Ala
                195                 200                 205

Ala Ile Leu Cys Ile Ser Ser Pro Phe Leu Val Ile Leu Tyr Ser Tyr
            210                 215                 220

Val Arg Ile Leu Val Ala Val Leu Val Met Pro Ser Pro Glu Gly Arg
225                 230                 235                 240

```
His Lys Ala Leu Ser Thr Cys Ser Ser His Leu Leu Val Val Thr Leu
            245                 250                 255

Phe Tyr Gly Ser Val Ser Phe Thr Tyr Leu Arg Pro Lys Ser Ser His
            260                 265                 270

Ser Pro Gly Met Asp Lys Leu Leu Ala Leu Phe Tyr Thr Ala Val Thr
            275                 280                 285

Ser Met Leu Asn Pro Ile Ile Tyr Ser Leu Arg Asn Lys Glu Val Lys
            290                 295                 300

Ala Ala Leu Arg Arg Thr Leu Asp Leu Lys Lys Ile Met Ser Ile Asn
305                 310                 315                 320

Arg (2) INFORMATION FOR SEQ ID NO:20:

(i) SEQUENCE CHARACTERISTICS:
        (A) LENGTH: 321 amino acids
        (B) TYPE: amino acid
        (D) TOPOLOGY: unknown (ii) MOLECULE TYPE: protein (xi) SEQUENCE DESCRIPTION: SEQ ID NO:20:

Met Ser Val Asn Cys Ser Leu Trp Gln Glu Asn Ser Leu Ser Val Lys
1               5                   10                  15

Arg Phe Ala Phe Ala Lys Phe Ser Glu Val Pro Gly Glu Cys Phe Leu
            20                  25                  30

Leu Phe Thr Leu Ile Leu Leu Met Phe Leu Val Ser Leu Thr Gly Asn
            35                  40                  45

Ile Leu Ile Ala Leu Ala Ile Cys Thr Ser Pro Ser Leu His Thr Pro
50                  55                  60

Met Tyr Phe Phe Leu Ala Asn Leu Ser Leu Leu Glu Ile Gly Tyr Thr
65                  70                  75                  80

Cys Ser Val Ile Pro Lys Met Leu Gln Ser Leu Val Ser Glu Ala Arg
                85                  90                  95

Gly Ile Ser Trp Glu Gly Cys Ala Ser Gln Met Phe Phe Ile Phe
            100                 105                 110

Phe Gly Ile Thr Glu Cys Cys Leu Leu Ala Ala Met Ala Phe Asp Arg
            115                 120                 125

Tyr Met Ala Ile Cys Ser Pro Leu His Tyr Ala Thr Arg Met Ser Arg
130                 135                 140

Gly Val Cys Ala Tyr Leu Ala Ile Val Ser Trp Val Met Gly Cys Ile
145                 150                 155                 160

Val Gly Leu Gly Gln Thr Asn Phe Ile Phe Ser Leu Asn Phe Cys Gly
                165                 170                 175

Pro Cys Glu Ile Asp His Phe Phe Cys Asp Leu Pro Pro Leu Leu Ala
            180                 185                 190

Leu Ala Cys Gly Asp Thr Ser Gln Asn Glu Ala Ala Ile Phe Val Ala
            195                 200                 205

Ala Val Leu Cys Ile Phe Ser Pro Phe Leu Leu Ile Ile Ser Ser Tyr
210                 215                 220

Val Arg Ile Leu Val Ala Val Leu Val Met Pro Ser Pro Glu Gly Arg
225                 230                 235                 240

His Lys Ala Leu Ser Thr Cys Ser Ser His Leu Leu Val Val Thr Leu
                245                 250                 255

Phe Tyr Gly Ser Thr Ser Ala Thr Tyr Leu Arg Ser Lys Ser Ser His
```

-continued

```
                    260                 265                 270
Ser Pro Gly Val Asp Lys Leu Leu Ala Leu Phe Tyr Thr Ser Val Thr
        275                 280                 285

Ser Met Leu Asn Pro Ile Ile Tyr Ser Leu Arg Asn Lys Glu Val Lys
    290                 295                 300

Gly Ala Leu Arg Arg Thr Leu Gly Leu Lys Lys Val Leu Thr Met Lys
305                 310                 315                 320

Arg
```

(2) INFORMATION FOR SEQ ID NO:21:

(i) SEQUENCE CHARACTERISTICS:
        (A) LENGTH: 177 amino acids
        (B) TYPE: amino acid
        (D) TOPOLOGY: unknown (ii) MOLECULE TYPE: protein (xi) SEQUENCE DESCRIPTION: SEQ ID NO:21:

```
Phe Leu Ser Met Phe Ser Ser Val Glu Cys Cys Phe Ile Thr Thr Val
1               5                   10                  15

Ile Pro Gln Leu Leu Thr Ile Ile Leu Ser Gly Arg Gln Lys Ile Pro
                20                  25                  30

Phe Met Ala Cys Ile Ser Gln Ala Phe Val Tyr Leu Val Gly Ala
            35                  40                  45

Thr Gly Phe Phe Leu Leu Gly Val Leu Ser Leu Asp Arg Phe Leu Ala
    50                  55                  60

Ile Cys Lys Pro Leu His Tyr Pro Thr Ile Met Ser Pro Arg Met Cys
65                  70                  75                  80

Phe Leu Leu Val Thr Val Ser Leu Val Leu Gly Phe Leu Phe Met Ala
                85                  90                  95

Ser Pro Val Val Met Leu Ser Gln Ser Phe Tyr Cys Gly Pro Asn Ile
            100                 105                 110

Ile Pro His Phe Phe Cys Asp Phe Gly Pro Leu Ala Asn Leu Ser Cys
        115                 120                 125

Ser Glu Thr Arg Ser Ile Glu Met Leu Phe Phe Thr Leu Ala Ile Ile
    130                 135                 140

Val Leu Phe Ala Ser Leu Leu Ile Ala Ile Phe Ala Tyr Ser Asn Ile
145                 150                 155                 160

Val Val Thr Ile Val Arg Leu Pro Ser Ala Arg Glu Arg Gln Arg Ala
                165                 170                 175

Phe
```

(2) INFORMATION FOR SEQ ID NO:22:

(i) SEQUENCE CHARACTERISTICS:
        (A) LENGTH: 327 amino acids
        (B) TYPE: amino acid
        (D) TOPOLOGY: unknown (ii) MOLECULE TYPE: protein (xi) SEQUENCE DESCRIPTION: SEQ ID NO:22:

```
Met Glu Trp Leu Met Thr Lys Glu Ile Lys Asn Gly Thr Leu Val Leu
1               5                   10                  15

Glu Phe Ile Phe Asp Arg Phe Pro Val Ala Glu His Leu Arg Ile Leu
                20                  25                  30

Phe Phe Leu Leu His Leu Leu Ala Tyr Leu Ala Ser Leu Met Gly Asn
```

```
            35                  40                  45
Met Leu Ile Ile Thr Ile Thr Cys Val Asp His Arg Leu Gln Thr Pro
 50                  55                  60

Met Tyr Phe Phe Leu Ser Met Phe Ser Ser Val Glu Cys Cys Phe Ile
 65                  70                  75                  80

Thr Thr Val Ile Pro Gln Leu Leu Thr Ile Ile Leu Ser Gly Arg Gln
                 85                  90                  95

Lys Ile Pro Phe Met Ala Cys Ile Ser Gln Ala Phe Val Tyr Leu Val
                100                 105                 110

Val Gly Ala Thr Gly Phe Phe Leu Leu Gly Val Leu Ser Leu Asp Arg
                115                 120                 125

Phe Leu Ala Ile Cys Lys Pro Leu His Tyr Pro Thr Ile Met Ser Pro
130                 135                 140

Arg Met Cys Phe Leu Leu Val Thr Val Ser Leu Val Leu Gly Phe Leu
145                 150                 155                 160

Phe Met Ala Ser Pro Val Val Met Leu Ser Gln Ser Phe Tyr Cys Gly
                165                 170                 175

Pro Asn Ile Ile Pro His Phe Phe Cys Asp Phe Gly Pro Leu Ala Asn
                180                 185                 190

Leu Ser Cys Ser Glu Thr Arg Ser Ile Glu Met Leu Phe Phe Thr Leu
                195                 200                 205

Ala Ile Ile Val Leu Phe Ala Ser Leu Leu Ile Ala Ile Phe Ala Tyr
210                 215                 220

Ser Asn Ile Val Val Thr Ile Val Arg Leu Pro Ser Ala Arg Glu Arg
225                 230                 235                 240

Gln Arg Ala Phe Ser Thr Cys Ser Ser His Leu Ile Val Leu Ser Leu
                245                 250                 255

Met Tyr Gly Ser Cys Ala Phe Ile Tyr Leu Lys Pro Lys Gln Arg Ser
                260                 265                 270

Arg Val Asp Ile Asn Arg Glu Ala Ala Leu Val Asn Thr Val Val Thr
                275                 280                 285

Pro Leu Leu Asn Pro Val Ile Tyr Thr Leu Arg Asn Lys Gln Val His
                290                 295                 300

Gln Ala Leu Arg Asp Ala Leu Ser Arg Val Gln Leu His Arg Tyr Gln
305                 310                 315                 320

Arg Arg His Ala Pro Ser Leu
                325

(2) INFORMATION FOR SEQ ID NO:23:

(i) SEQUENCE CHARACTERISTICS:
        (A) LENGTH: 327 amino acids
        (B) TYPE: amino acid
        (D) TOPOLOGY: unknown (ii) MOLECULE TYPE: protein (xi) SEQUENCE DESCRIPTION: SEQ ID NO:23:

Met Glu Trp Leu Met Thr Lys Glu Ile Lys Asn Gly Thr Leu Val Leu
 1                   5                  10                  15

Glu Phe Ile Phe Asp Arg Phe Pro Val Ala Glu His Leu Arg Ile Leu
                 20                  25                  30

Phe Phe Leu Leu His Leu Leu Ala Tyr Leu Ala Ser Leu Met Gly Asn
                 35                  40                  45

Met Leu Ile Ile Thr Ile Thr Cys Val Asp His Arg Leu Gln Thr Pro
 50                  55                  60
```

```
Met Tyr Phe Phe Leu Ser Met Phe Ser Ser Val Glu Cys Cys Phe Ile
 65                  70                  75                  80

Thr Thr Val Ile Pro Gln Leu Leu Thr Ile Ile Leu Ser Gly Arg Gln
                 85                  90                  95

Lys Ile Pro Phe Met Ala Cys Ile Ser Gln Ala Phe Val Tyr Leu Val
                100                 105                 110

Val Gly Ala Thr Gly Phe Phe Leu Leu Gly Val Leu Ser Leu Asp Arg
                115                 120                 125

Phe Leu Ala Ile Cys Lys Pro Leu His Tyr Pro Thr Ile Met Ser Pro
    130                 135                 140

Arg Met Cys Phe Leu Leu Val Thr Val Ser Leu Val Leu Gly Phe Leu
145                 150                 155                 160

Phe Met Ala Ser Pro Val Val Met Leu Ser Gln Ser Phe Tyr Cys Gly
                165                 170                 175

Pro Asn Ile Ile Pro His Phe Phe Cys Asp Phe Gly Pro Leu Ala Asn
                180                 185                 190

Leu Ser Cys Ser Glu Thr Arg Ser Ile Glu Met Leu Phe Phe Thr Leu
    195                 200                 205

Ala Ile Ile Val Leu Phe Ala Ser Leu Leu Ile Ala Ile Phe Ala Tyr
    210                 215                 220

Ser Asn Ile Val Val Thr Ile Val Arg Leu Pro Ser Ala Arg Glu Arg
225                 230                 235                 240

Gln Arg Ala Phe Ser Thr Cys Ser Ser His Leu Ile Val Leu Ser Leu
                245                 250                 255

Met Tyr Gly Ser Cys Ala Phe Ile Tyr Leu Lys Pro Lys Gln Arg Ser
                260                 265                 270

Arg Val Asp Ile Asn Arg Glu Ala Ala Leu Val Asn Thr Val Val Thr
                275                 280                 285

Pro Leu Leu Asn Pro Val Ile Tyr Thr Leu Arg Asn Lys Gln Val His
                290                 295                 300

Gln Ala Leu Arg Asp Ala Leu Ser Arg Val Gln Leu His Arg Tyr Gln
305                 310                 315                 320

Arg Arg His Ala Pro Ser Leu
                325

(2) INFORMATION FOR SEQ ID NO:24:

(i) SEQUENCE CHARACTERISTICS:
        (A) LENGTH: 327 amino acids
        (B) TYPE: amino acid
        (D) TOPOLOGY: unknown (ii) MOLECULE TYPE: protein (xi) SEQUENCE DESCRIPTION: SEQ ID NO:24:

Met Glu Trp Leu Met Thr Asp Asp Thr Lys Asn Gly Thr Leu Val Gln
1               5                   10                  15

Glu Phe Ile Leu Glu Gly Phe Pro Val Ala Glu His Leu Arg Ile Leu
                20                  25                  30

Phe Phe Leu Leu His Met Leu Ala Tyr Leu Ala Ser Ser Met Gly Asn
                35                  40                  45

Met Leu Ile Ile Thr Tyr Thr Cys Val Asp His Arg Leu Gln Thr Pro
    50                  55                  60

Met Tyr Phe Phe Leu Ser Thr Phe Ser Phe Val Glu Cys Cys Phe Ile
 65                 70                  75                  80
```

```
Thr Thr Val Ile Pro Gln Leu Leu Thr Ile Ile Leu Ser Gly Arg Gln
                85                  90                  95

Lys Ile Pro Phe Met Ala Cys Phe Ser Gln Ala Phe Val Val Leu Phe
               100                 105                 110

Leu Gly Ala Ala Val Phe Phe Leu Met Ala Val Leu Ser Leu Asp Arg
           115                 120                 125

Phe Leu Ala Ile Cys Lys Pro Leu His Tyr Pro Thr Ile Met Ser Pro
       130                 135                 140

Arg Met Cys Phe Leu Leu Val Thr Val Ser Leu Val Leu Gly Phe Leu
145                 150                 155                 160

Phe Met Ala Ser Pro Val Val Met Leu Ser Gln Ser Phe Tyr Cys Gly
               165                 170                 175

Pro Asn Ile Ile Pro His Phe Phe Cys Asp Phe Gly Pro Leu Ala Asn
           180                 185                 190

Leu Ser Cys Ser Glu Thr Arg Ser Ile Glu Met Leu Phe Phe Thr Leu
       195                 200                 205

Ala Ile Ile Val Leu Phe Thr Ser Leu Leu Ile Ala Ile Phe Ala Tyr
   210                 215                 220

Ser Thr Ile Val Val Thr Ile Val Arg Leu Pro Ser Ala Arg Glu Arg
225                 230                 235                 240

Gln Arg Ala Phe Ser Thr Cys Ser Ser His Leu Ile Val Leu Ser Leu
               245                 250                 255

Met Tyr Gly Ser Cys Val Phe Ile Tyr Leu Lys Pro Lys Gln Arg Ser
           260                 265                 270

Arg Val Asp Thr Asn Arg Glu Ala Val Leu Val Asn Met Val Val Thr
       275                 280                 285

Pro Leu Leu Asn Pro Val Ile Tyr Thr Leu Arg Asn Lys Gln Val His
   290                 295                 300

Gln Ala Leu Arg Asp Ala Leu Ser Arg Val Gln Leu His Arg Tyr Gln
305                 310                 315                 320

Ser Arg Lys Ala Pro Leu Ser
               325
```

(2) INFORMATION FOR SEQ ID NO:25:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:25:

```
TGTTTGTAAC CATGTAAATT TATGCGTGAG CCCATTCCAC AGAGCAGACA TGTTCTAAAA    60

GAAGAGGGGA AATGCTTAGA GATGAGTGTC AACTGTTCTC TGTGGCAGGA GAATAGTTTG   120

TCTGTCAAAC GCTTTGCATT TGCCAAGTTT TCTGAGGTCC CTGGAGAATG CTTCCTC      177
```

(2) INFORMATION FOR SEQ ID NO:26:

(i) SEQUENCE CHARACTERISTICS:
        (A) LENGTH: 91 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:26:

```
TGTAATAATT TTGTCCTTTC TTTCAGGAGT ATGAGTGTCA ACTGTTCTCT GTGGCAGGAG        60

AATAGTTTGT CTGTCAAACG CTTTGCATTC C                                     91
```

(2) INFORMATION FOR SEQ ID NO:27:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: DNA (other)

(xi) SEQUENCE DESCRIPTION: SEQ ID NO:27:

```
TGTAATAATT TTGTCCTTTC TTTCAGGAGT ATGAGTGTCA ACTGTTCTCT GTGGCAGGAG        60

AATAGTTTGT CTGTCAAACG CTTTGCATTT GCCAAGTTCT CTGAGGTCCC TGGAGAATGC       120

TTCCTC                                                                 126
```

(2) INFORMATION FOR SEQ ID NO:28:

(i) SEQUENCE CHARACTERISTICS:
        (A) LENGTH: 56 amino acids
        (B) TYPE: amino acid
        (D) TOPOLOGY: unknown (ii) MOLECULE TYPE: protein (xi) SEQUENCE DESCRIPTION: SEQ ID NO:28:

```
Pro Cys Lys Phe Met Arg Glu Pro Ile Pro Gln Ser Arg His Val Leu
1               5                   10                  15

Lys Glu Glu Gly Phe Cys Leu Glu Met Ser Val Asn Cys Ser Leu Trp
            20                  25                  30

Gln Glu Asn Ser Leu Ser Val Lys Arg Phe Ala Phe Ala Lys Phe Ser
        35                  40                  45

Glu Val Pro Gly Glu Cys Phe Leu
    50                  55
```

(2) INFORMATION FOR SEQ ID NO:29:

(i) SEQUENCE CHARACTERISTICS:
        (A) LENGTH: 27 amino acids
        (B) TYPE: amino acid
        (D) TOPOLOGY: unknown (ii) MOLECULE TYPE: protein (xi) SEQUENCE DESCRIPTION: SEQ ID NO:29:

```
Phe Cys Pro Phe Phe Gln Glu Met Ser Val Asn Cys Ser Leu Trp
1               5                   10                  15

Gln Glu Asn Ser Leu Ser Val Lys Arg Phe Ala Phe
            20                  25
```

(2) INFORMATION FOR SEQ ID NO:30:

(i) SEQUENCE CHARACTERISTICS:
        (A) LENGTH: 39 amino acids
        (B) TYPE: amino acid
        (D) TOPOLOGY: unknown (ii) MOLECULE TYPE: protein (xi) SEQUENCE DESCRIPTION: SEQ ID NO:30:

Phe Cys Pro Phe Phe Gln Glu Met Ser Val Asn Cys Ser Leu Trp Gln Glu

```
                1               5                    10                   15
Asn Ser Leu Ser Val Lys Arg Phe Ala Phe Ala Lys Phe Ser Glu Val Pro
                    20                  25                  30
Gly Glu Cys Phe Leu
35
```

(2) INFORMATION FOR SEQ ID NO:31:

(i) SEQUENCE CHARACTERISTICS:
        (A) LENGTH: 16 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:31:

TGTCCTTTCT TTCAGG                  16